(12) United States Patent
Bakre et al.

(10) Patent No.: US 10,900,968 B2
(45) Date of Patent: Jan. 26, 2021

(54) METHOD OF PROGNOSING AND PREDICTING BREAST CANCER RECURRENCE, MARKERS EMPLOYED THEREIN AND KIT THEREOF

(71) Applicant: ONCOSTEM PTE. LTD., Singapore (SG)

(72) Inventors: Manjiri Bakre, Bangalore (IN); Charusheila Ramkumar, Bangalore (IN)

(73) Assignee: ONCOSTEM PTE. LTD., Singapore (SG)

(*) Notice: Subject to any disclaimer, the term of this patent is extended or adjusted under 35 U.S.C. 154(b) by 460 days.

(21) Appl. No.: 15/604,079

(22) Filed: May 24, 2017

(65) Prior Publication Data

US 2017/0343548 A1 Nov. 30, 2017

(30) Foreign Application Priority Data

May 24, 2016 (IN) .............................. 201641017874

(51) Int. Cl.
*G01N 31/00* (2006.01)
*G01N 33/53* (2006.01)
*G01N 33/574* (2006.01)

(52) U.S. Cl.
CPC . *G01N 33/57415* (2013.01); *G01N 33/57492* (2013.01); *G01N 2333/70585* (2013.01)

(58) Field of Classification Search
None
See application file for complete search history.

(56) References Cited

U.S. PATENT DOCUMENTS 8,772,455 B2 * 7/2014 Bakre ................ C07K 14/4748
530/350

FOREIGN PATENT DOCUMENTS

| WO | 2012/115885 A1 | 8/2012 | |
|---|---|---|---|
| WO | 2012/131564 A1 | 10/2012 | |
| WO | WO-2012131564 A1 * | 10/2012 | ......... C07K 14/4748 |

OTHER PUBLICATIONS

Bakre, "Development of a Novel IHC Based Test for Prediction of Risk of Recurrence for Breast Cancer Patients" Biomarkers & Clinical Research, pp. 1-10, Sep. 1, 2015.*
Tascilar et al. (Annals of Oncology 10,Suppl. 4:S107-S110, 1999).*
Tockman et al. (Cancer Research 52:2711s-2718s, 1992).*
Sosonkina et al. Exp. Oncol. 2011, vol. 33, No. 1, pp. 42-46 (Year: 2011).*
Chekhun et al. Exp. Oncol. 2013, vol. 35, No. 3, pp. 174-179 (Year: 2013).*
Van Marck et al. (Cancer Research, Oct. 1, 2005, 65(19) pp. 8774-8783). (Year: 2005).*
Geiger et al. (Journal of Cell Science, vol. 97, pp. 607-614, 1990). (Year: 1990).*
Sood et al. (Cancer Research: Cancer Chemistry, Abstract 2499, vol. 74, No. 19, Supp. Suppl.1, published Oct. 2014). (Year: 2014).*
Manjiri Bakre, "Development of a Novel IHC Based Test for Prediction of Risk of Recurrence for Breast Cancer Patients" Biomarkers & Clinical Research, pp. 1-10, Sep. 1, 2015.
Aug. 25, 2017 International Search Report issued in International Patent Application No. PCT/IB2017/053060.
Aug. 25, 2017 Written Opinion of the International Searching Authority issued in International Patent Application No. PCT/IB2017/053060.

* cited by examiner

*Primary Examiner* — Lisa V Cook
(74) *Attorney, Agent, or Firm* — Oliff PLC

(57) ABSTRACT

A method of prognosing and predicting breast cancer recurrence stratifies early stage ER+/PR+ and Her2− breast cancer patients with invasive ductal/lobular carcinoma of the breast into low risk or high risk for breast cancer recurrence by employing an IHC based assay which assesses or measures expression of a combination of 5 biomarkers and by employing a histopathological analysis which assesses 3 clinical prognostic parameters.

12 Claims, 4 Drawing Sheets

US 10,900,968 B2

METHOD OF PROGNOSING AND PREDICTING BREAST CANCER RECURRENCE, MARKERS EMPLOYED THEREIN AND KIT THEREOF

TECHNICAL FIELD

The present disclosure pertains to the field of molecular oncology/biotechnology. The present disclosure relates to a method of prognosing and predicting breast cancer recurrence in patients. More particularly, the present disclosure relates to a method of prognosing which stratifies early stage breast cancer patients with hormone receptor positive and Her2 receptor negative invasive ductal/lobular carcinoma of the breast into low risk or high risk for breast cancer recurrence by employing an IHC based assay which assesses or measures expression of a combination of 5 biomarkers and by employing a histopathological analysis which assesses 3 clinical prognostic parameters. The present disclosure also relates to a combination of 5 biological markers and 3 clinical parameters employed in the method for prognosis of breast cancer, a kit/test comprising the antibodies against said markers for said prognosis and an IHC based assay system comprising said markers.

BACKGROUND OF THE DISCLOSURE

In the field of oncology, the detection, identification and characterization of tumor cells is an important aspect for diagnosis of cancer and for detection/prognosis of cancer recurrence. Of the many challenges of medicine, none has had a more controversial beginning or has experienced more hard-fought progress than the treatment and cure of cancer and more importantly, prevention of cancer recurrence. Effective treatment for most patients is needed to reach every organ in the body to pin down the metastatic disease. More than 70% of cancer patients undergo chemo/radio therapy.

Despite the path breaking progress in oncology therapy from multiple angles, cancer cure still remains elusive. Advanced solid malignancies remain therapeutic challenges despite maximal therapy, in part, due to the development of resistance to radiation and chemotherapy. For eg. Glioblastomas are among the most lethal of cancers with current therapies offering only palliation. Standard-of-care for glioblastoma consists of surgical resection, ionizing external beam irradiation, and chemotherapy. Though radiotherapy has been the most effective nonsurgical treatment modality, but yet recurrence is essentially universal.

At present, about 95% of the patients with hormone receptor positive and Her2 negative early stage breast cancer get treated with chemotherapy, with majority of early stage cancer patients getting over-treated with Chemotherapy.

Thus, majority of patients undergoing chemo/radio therapy suffer from un-necessary severe side effects of the treatment. In addition, many patients also show resistance to the treatment resulting in treatment failure and cancer recurrence. Existing techniques for assessing risk of cancer recurrence in the abovementioned hormone receptor positive and Her2 receptor negative patients are expensive, applicable only for stage I cancer patients and not predictive in nature.

Thus, in spite of availability of many ways of standardized methods for diagnosis & prognosis of breast cancer currently, there exists a need to develop prognostic and predictive tests that can determine risk of cancer recurrence and effectiveness of the prescribed chemo/radio therapy, with accuracy and at affordable costs, which in-turn will help devise new drug therapy. Breast cancer recurrence risk in ER+ stage 1 and stage 2 patients being assessed currently by considering clinical parameters and biomarker based means (Prognostic markers: Age, tumor grade, size, nodes with metastasis (TNM) and Predictive markers: ER/PR/Her-2-neu) is insufficient, leading to over-treatment of patients with chemotherapy thereby leading to unnecessary side-effects. Over the past decade, several molecular tests have been developed to predict risk of recurrence in Breast Cancer. Treatment of early stage patients in the West today is decided based on the risk predicted by any of these tests including Oncotype Dx, Mammaprint, PAM50 and EndoPredict. These tests are primarily based on hormone receptor & proliferative pathways. These pathways are important, but insufficient to accurately predict risk of recurrence as Breast cancer is a heterogeneous disease and several pathways regulate the molecular pathogenesis of the disease. Further, Oncotype Dx, Mammaprint, Endopredict and PAM50 are used primarily for ER+/PR+/Her2-Stage 1/2 patient who are lymph node negative (LN−) and for limited patients with 1-3 lymph nodes positive. Thus, these tests are applicable for a highly-limited set of Stage 1 patients which are not common outside the western world and are largely prognostic with limited chemo-predictivity. Further all the 4 tests mentioned above are based on gene expression detection in whole FFPE blocks by microarray or q-PCR, and do not detect protein expression thus unable to prescribe new targeted drugs apart from also being very expensive and impractical for application in Asian Patient Cohort, as only ~5% of patients are diagnosed in LN−, Stage 1 cancer.

The instant disclosure therefore provides for a prognostic and predictive method which addresses all the limitations existing in the prior art for treating cancer and devising new or personalized drug therapy.

STATEMENT OF THE DISCLOSURE

Accordingly, the present disclosure relates to a method of measuring biomarker expression, comprising measuring expression of five biomarkers by assaying a biological sample with a combination of antibodies, wherein the biological sample is obtained from a subject having early stage ER+/PR+ and Her2− breast cancer or after removal of the early stage ER+/PR+ and Her2− breast cancer and the five biomarkers are CD44, ABCC11, N-cadherin, Pan-cadherin and ABCC4; a method of performing immunohistochemistry (IHC) on a tumor sample obtained from a subject having early stage ER+/PR+ and Her2-breast cancer or after removal of the early stage ER+/PR+ and Her2− breast cancer, comprising performing IHC on the tumor sample to optionally detect hormone receptor expression by detecting whether cells are expressing at least one receptor selected from the group consisting of estrogen receptor and, progesterone receptor, and ensuring tumor samples do not express Her2 receptor and performing the method as above on the tumor sample by IHC to measure the expression of the five biomarkers CD44, ABCC11, N-cadherin, Pan-cadherin and ABCC4; a method of prognosing and treating a subject having early stage ER+/PR+ and Her2− breast cancer or after removal of the early stage ER+/PR+ and Her2− breast cancer, comprising prognosing whether the subject is at high or low risk for breast-cancer recurrence by performing, and analyzing the results of, the method as above; and treating the prognosed subject with chemotherapy if prognosed as high risk for breast-cancer recurrence; a combination of antibodies, comprising antibodies specific for five biomarkers CD44, ABCC11, N-cadherin, Pan-cadherin and ABCC4; a kit comprising the combination of antibodies as above and instructions for measuring expression of the five biomarkers CD44, ABCC11, N-cadherin, Pan-cadherin and ABCC4; an IHC-based assay system, comprising the combination of antibodies as above; and a method of predicting the likelihood of recurrence of breast cancer in a subject having early stage ER+/PR+ and Her2– breast cancer or after removal of the early stage ER-F/PR+ and Her2– breast cancer, comprising: measuring expression level of five biomarkers CD44, ABCC11, N-cadherin, Pan-cadherin and ABCC4, calculating a relapse score for said subject by measuring the differential expression levels of each of the biomarkers and their contribution to breast cancer recurrence along with three clinical parameters, and using said relapse score to determine the likelihood of breast cancer recurrence.

BRIEF DESCRIPTION OF THE ACCOMPANYING FIGURES

The features of the present disclosure will become fully apparent from the following description taken in conjunction with the accompanying figures. With the understanding that the figures depict only several embodiments in accordance with the disclosure and are not to be considered limiting of its scope, the disclosure will be described further through use of the accompanying figures.

Figure 3:
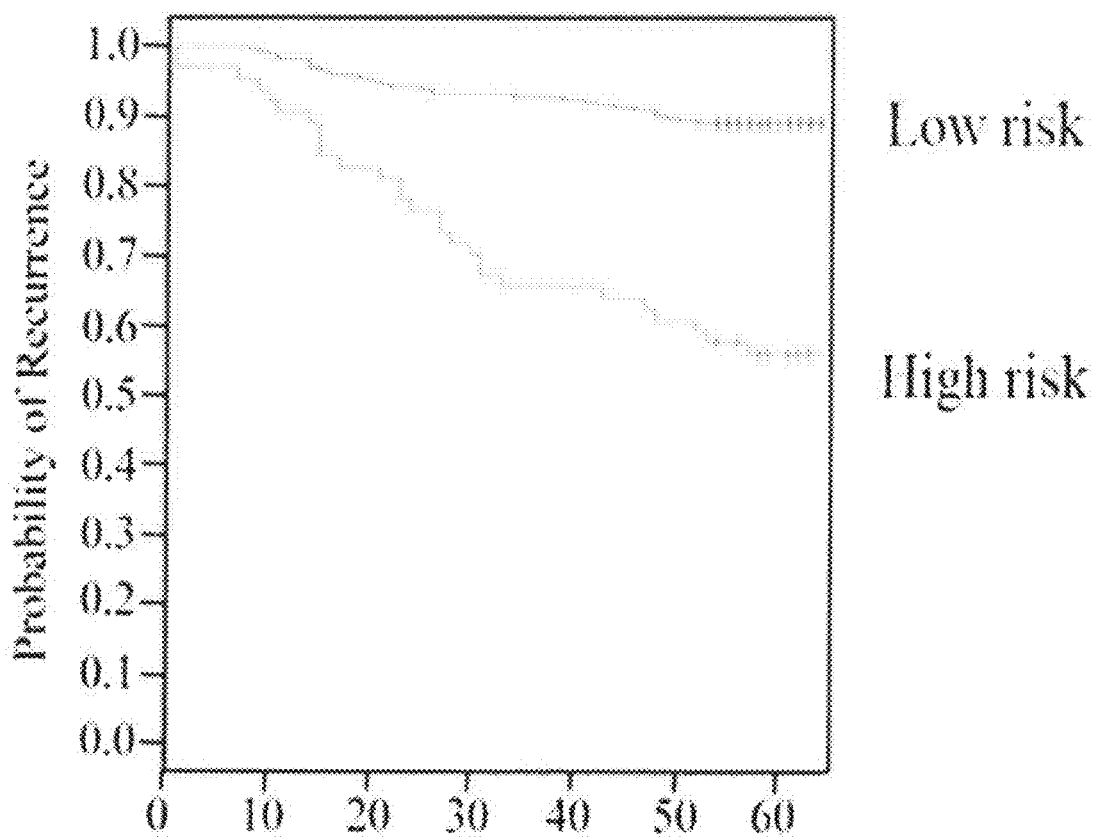

FIG. 3 illustrates Kaplan Meier (KM) curve results of risk stratification of early stage ER+/PR+ and Her2– breast cancer patients by employing the prognostic method/test of the instant disclosures. As can be observed from the KM of the instant disclosure, low and high risk patients are separated well and predicted for all cases as there is no intermediate zone in the KM curve of CanAssist-Breast test.

Figure 4:
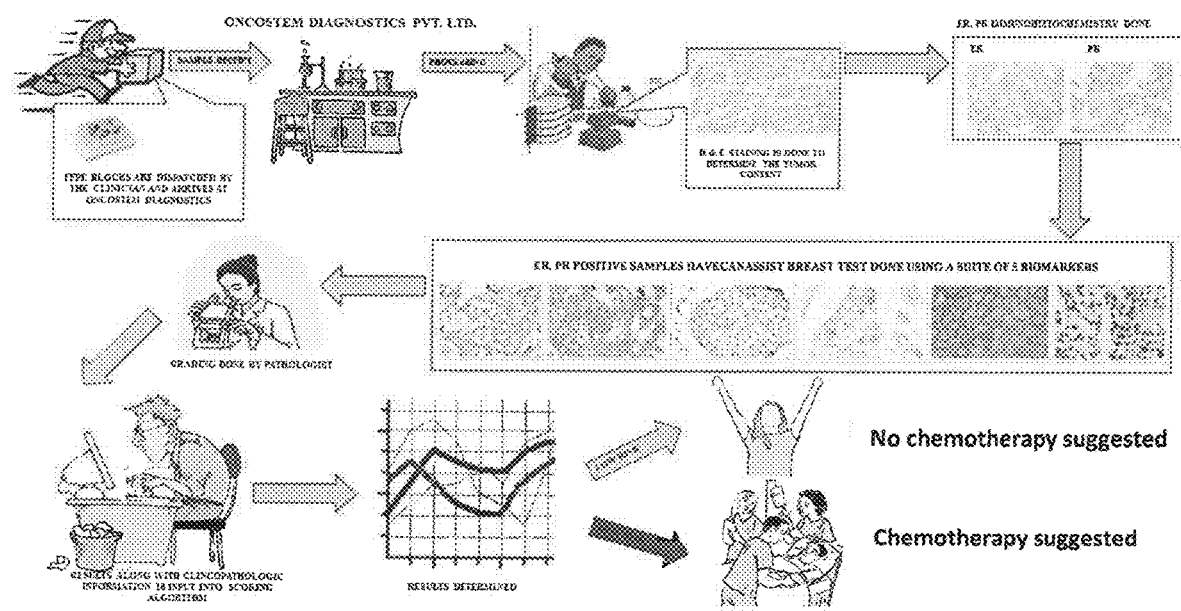

FIG. 4 illustrates a brief work-flow of the method employed in predicting risk of recurrence in early stage ER+/PR+ and Her2– breast cancer patients, from start to finish.

DETAILED DESCRIPTION OF THE DISCLOSURE

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular as is considered appropriate to the context and/or application. The various singular/plural permutations may be expressly set forth herein for the sake of clarity. Generally, nomenclatures used in connection with, and techniques of biotechnology, molecular oncology, molecular and cellular biology described herein are those well-known and commonly used in the art. Certain references and other documents cited herein are expressly incorporated herein by reference. In case of conflict, the present specification, including definitions, will control. The materials, methods, figures and examples are illustrative only and not intended to be limiting.

The present disclosure has utility in the field of oncology for stratifying early stage ER+/PR+ and Her2– breast cancer patients into high or low risk for breast cancer recurrence, prior to cancer treatment and/or post-surgery. In an embodiment, the prognostic and/or predictive test in the instant invention is preferably performed on patient samples after surgery and before chemotherapy, since the decision to give chemotherapy is based on test results. The present disclosure thus relates to a prognostic test for detecting cancer recurrence preferably in early stage ER+/PR+ and Her2– breast cancer as well as a predictive test which will enable chemotherapy decision and also devising of new drugs or personalized therapy specifically based on the prognostic outcome of the patient.

The present disclosure thus by helping in stratifying the early stage ER+/PR+ and Her2-breast cancer patients into low or high risk of breast cancer recurrence will therefore enable to intelligently chalk out a module to treat low and high risk patients, as per the optimal chemotherapy requirement; thus overcoming under treatment/over treatment of patients as applicable; and also help in devising new age effective drugs or personalized therapy for cancer treatment.

Before the method of prognosis, biomarkers, kit comprising antibodies against said markers and other embodiments of the present disclosure are disclosed and described, it is to be understood that the terminologies used herein are for the purpose of describing particular embodiments only and are not intended to be limiting. It must be noted that, as used in the specification and the appended claims, the singular forms "a," "an" and "the" include plural referents unless the context clearly dictates otherwise.

As used herein, "tumor" or "cancer" are terms as well known in the art and used interchangeably throughout the disclosure. Similarly, the terms "clinical prognostic factors" "clinical prognostic parameters" or "clinicopathological parameters/clinical parameters/clinical variables"; "algorithm" or "module" or "equation"; "IHC scoring/scoring" or "IHC grading/grading"; are one and the same and used interchangeably throughout the disclosure.

"Status" means a state of gene expression of a set of genetic markers whose expression is strongly correlated with a particular phenotype. For example, "ER status" means a state of gene expression of a set of genetic markers whose expression is strongly correlated with that of ESR1 (estrogen receptor gene), wherein the pattern of these genes' expression differs detectably between tumors expressing the receptor and tumors not expressing the receptor.

The terms "ER+" or "ER+ve" or "estrogen receptor positive" are used interchangeably throughout the disclosure and intend to convey the positive expression of the estrogen receptor. Similarly, the terms "PR+" or "PR+ve" or "progesterone receptor positive" are used interchangeably throughout the disclosure and intend to convey the positive expression of the progesterone receptor.

The term "hormone receptor positive" used throughout the disclosure intends to convey the positive expression of one of or both of estrogen receptor and progesterone receptor.

The terms "Her2-" or "Her2-ve" or "Her2 negative" or "Her-2-neu –ve" or "Her-2-neu receptor negative" or "Her-2-neu negative" or "negative for Her-2-neu receptor" are used interchangeably throughout the disclosure and intend to convey the absence of expression of the human epidermal growth factor receptor 2.

"Marker" or "Bio-marker" means an entire gene/protein, or an EST derived from that gene, the expression or level of which changes between certain conditions. Where the expression of the gene correlates with a certain condition, the gene is a marker for that condition.

The term "High" with regards to risk of breast cancer recurrence means that a patient is expected to have >9% probability of distant recurrence within five years of initial treatment of breast cancer.

The term "Low" with regards to risk of breast cancer recurrence means that a patient is expected to have 9% or lower probability of distant recurrence of breast tumor within five years of initial treatment of breast cancer.

The term "breast cancer" in the present disclosure refers to hormone receptor positive invasive ductal carcinoma of the breast or invasive lobular carcinoma of the breast. Preferably, the carcinoma is hormone receptor positive invasive ductal carcinoma of the breast.

The term "prognosis" or "prognostic marker" in the present disclosure relates to predicting disease progression without taking into consideration any reference to therapy/treatment/drug. A very qualitative way of prediction for eg: age, tumor stage, tumor grade are prognostic markers. This prognosis relates to understanding the long-term outcome of a disease.

The term "IHC grading" in the present disclosure relates to raw grading values assigned for each stained IHC slide by the Pathologist based on % staining (0-100%) and Intensity of staining (0-3).

The term IHC/immunohistochemistry in the present disclosure (devoid of reference to prior arts) relates to Morphometric immunohistochemistry. The term also intends to encompass the conventional histopathological techniques associated with the process of carrying out the IHC. The immunohistochemistry analysis carried out within the present disclosure encompasses the conventional IHC method, whereby the identification of biological markers is carried out by visualizing a colored reaction or fluorescence obtained at completion of the method due to staining of the desired biomarkers present on the cells from the sample.

The terms "CanAssist Breast score" or "CanAssist Breast test score" or "relapse score" or "prediction score" or "score" in the present disclosure are used interchangeably and relates to an algorithm generated score computed using the averages of raw grading (for percentage and/or intensity of staining) for each IHC marker as well as information regarding tumor size, node status and tumor grade.

The term "tumor grade" in the present disclosure relates to grade, ranging from 1-3 assigned to the tumor based on histopathological features according to the modified Bloom-Richardson Elston criteria.

The term "tumor stage" in the present disclosure relates to the TNM staging of Breast Cancer which is based on tumor size (T) Node status (N) and Metastasis in the body (M).

The term "predictive" or "predictive marker" in the present disclosure relates to a marker that not only gives some kind of reference to disease progression but more importantly will direct a therapy based on the presence of the markers for eg: ER, PR and Her2. Employing them is prognostic along with a direction as to what a possible therapy could be. Thus prediction is related to understanding benefit to the patient in response to certain treatment.

In the present disclosure, the prognostic and predictive test herein is also referred to as "CanAssist Breast test".

The present disclosure relates to a method of measuring biomarker expression, comprising measuring expression of five biomarkers by assaying a biological sample with a combination of antibodies, wherein the biological sample is obtained from a subject having early stage ER+/PR+ and Her2− breast cancer or after removal of the breast cancer; and the five biomarkers are CD44, ABCC11, N-cadherin, Pan-cadherin and ABCC4. The biomarker expression is measured for prognosis about whether the subject having cancer is at high or low risk for breast-cancer recurrence at a distant site.

The present disclosure also relates to a method of performing immunohistochemistry (IHC) on a tumor sample obtained from a subject having early stage ER+/PR+ and Her2-breast cancer or after removal of the breast cancer, comprising performing IHC on the tumor sample to detect receptor expression by detecting whether cells are expressing at least one receptor selected from the group consisting of estrogen receptor and progesterone receptor and not having Her2 receptor and performing the method as above on the tumor sample by IHC if receptor expression is detected to measure the expression of the five biomarkers CD44, ABCC11, N-cadherin, Pan-cadherin and ABCC4. Alternatively, the IHC is directly performed on samples known to be positive for estrogen receptor and/or progesterone receptor and negative for Her-2-neu receptor. Thus, the method of the present disclosure may comprise performing IHC to determine the status of estrogen receptor, progesterone receptor and Her-2-neu receptor; or may not comprise performing IHC to determine the status of estrogen receptor, progesterone receptor and Her-2-neu receptor, if such status is already/previously known for a sample.

Thus, preferably, the present disclosure relates to a method of performing immunohistochemistry (IHC) on a tumor sample obtained from a subject having early stage ER+/PR+ and Her2− breast cancer or after removal of the breast cancer, comprising performing IHC on the tumor sample to measure the expression of the five biomarkers CD44, ABCC11, N-cadherin, Pan-cadherin and ABCC4.

The present disclosure also relates to a method of prognosing and treating a subject having early stage ER+/PR+ and Her2− breast cancer or after removal of the breast cancer, comprising prognosing whether the subject is at high or low risk for breast-cancer recurrence by performing, and analyzing the results of, the method as above; and treating the prognosed subject with chemotherapy if prognosed with high risk for breast-cancer recurrence.

The breast cancer referred to in the present disclosure is stage I, II or IIIA hormone receptor positive, Her2 receptor negative invasive ductal carcinoma, or invasive lobular carcinoma of the breast.

In embodiments of the present disclosure, the breast-cancer recurrence is prognosed in patients having early stage ER+/PR+ and Her2− breast cancer or in patients after surgical removal of the early stage ER+/PR+ and Her2− breast cancer.

The breast cancer recurrence risk in the present disclosure is measured by analyzing the expression of the five biomarkers along with three clinical parameters only if expression of at least one of estrogen receptor or progesterone receptor is detected on the tumor cells which also do not express Her2 receptor. The expression of the five biomarkers is thereafter measured on basis of percentage of cells (0-100) stained and staining intensity of cells (0-3).

The CanAssist-Breast test further comprises assessing three clinical parameters viz node status, tumor grade, and tumor size, wherein the node status includes tumor node positive and tumor node negative, the tumor grade includes Grades 1, 2 and 3 according to the modified Bloom-Richardson-Elston criteria, and the tumor size includes T1, T2, or T3 according to the TNM classification of breast cancer.

The tumor sample obtained from the subject is collected, fixed, sectioned, and IHC is performed by adding primary antibodies and secondary antibodies conjugated with a detectable label and detecting a color or fluorescence from the detectable label.

The present disclosure also relates to a combination of antibodies specific for the five biomarkers CD44, ABCC11, N-cadherin, Pan-cadherin and ABCC4.

The present disclosure also relates to a kit comprising the combination of antibodies and instructions for measuring expression of the five biomarkers CD44, ABCC11, N-cadherin, Pan-cadherin and ABCC4.

In embodiments of the present disclosure, the kit also comprises at least one member from IHC reagents such as xylene, isopropanol, ethanol, buffer solutions, protein blocking agents, primary antibodies, secondary antibodies labeled with enzymes such as horseradish peroxidase (HRP) or alkaline phosphatase (AP) or with fluorescent tags such as fluorescein isothiocyanate (FITC) or phycoerythrin (PE) or with molecule biotin/streptavidin, and substrates such as diamino benzydene (DAB) or p-nitrophenyl phosphate (PNPP).

The present disclosure also relates to an IHC-based assay system, comprising the combination of antibodies specific for CD44, ABCC11, N-cadherin, Pan-cadherin, and ABCC4.

In embodiments of the present disclosure, the IHC-based assay system further comprises at least one member from IHC reagents such as xylene, isopropanol, ethanol, buffer solutions, protein blocking agents, primary antibodies, secondary antibodies labeled with enzymes such as horseradish peroxidase (HRP) or alkaline phosphatase (AP) or with fluorescent tags such as fluorescein isothiocyanate (FITC) or phycoerythrin (PE) or with molecule biotin/streptavidin, and substrates such as diamino benzydene (DAB) or p-nitrophenyl phosphate (PNPP).

The present disclosure also relates to a method of predicting the likelihood of recurrence of breast cancer in a subject having early stage ER+/PR+ and Her2− breast cancer or after removal of the breast cancer, comprising: measuring expression level of five biomarkers CD44, ABCC11, N-cadherin, Pan-cadherin and ABCC4; calculating a relapse score for said subject by measuring the differential expression levels of each of the biomarkers and their contribution to breast cancer recurrence along with three clinical parameters; and using said relapse score to determine the likelihood of breast cancer recurrence.

In embodiments of the present disclosure, the method further comprises assessing clinical parameters node status, tumor grade, and tumor size, wherein the node status includes tumor node positive and tumor node negative, the tumor grade includes Grades 1, 2 and 3, and the tumor size includes T1, T2, or T3.

In further embodiments of the present disclosure, the breast cancer is stage I, II or IIIA hormone receptor positive, Her-2-neu receptor negative invasive ductal carcinoma, or invasive lobular carcinoma of the breast. Accordingly, the term 'early stage' used to describe the stage of breast cancer of the present disclosure refers to breast cancer at stage I, II or IIIA.

The method of the present disclosure thus relates to a cost-effective, accurate, robust, prognostic and predictive, ISO-certified, Morphometric IHC test, which is useful for ER+/PR+ and Her2− breast cancer patients across Stages I, II and IIIA of cancer.

The method of the present disclosure is a 'New' biomarker/'New' biomarker combination leading to 'broadly distributed prognostic and predictive' test which can assess 'risk of recurrence' and can offer 'targeted' treatments to pre or post-menopausal patients, ER+ve and/or PR+ve, Her2−ve, and Lymph node −ve or +ve patients in stage I, stage II or stage IIIA cancer.

The present disclosure therefore relates to a method of prognosing early stage ER+/PR+ and Her2− breast cancer patients for risk of breast cancer recurrence. The risk of recurrence is considered high if the probability of recurrence is greater than about 9% and low if it is less than or equal to about 9%.

In a non-limiting embodiment, the method of prognosis involves employing a morphometric IHC based assay to predict the risk of breast cancer recurrence.

In a preferred embodiment, the breast cancer patients are patients, with I, II or IIIA stage hormone receptor positive, Her2 negative invasive ductal or lobular carcinoma of the breast.

In another preferred embodiment, hormone receptor positive includes $ER^+$ (Estrogen receptor positive) and/or PR+ (Progesterone receptor positive).

Figure 2:
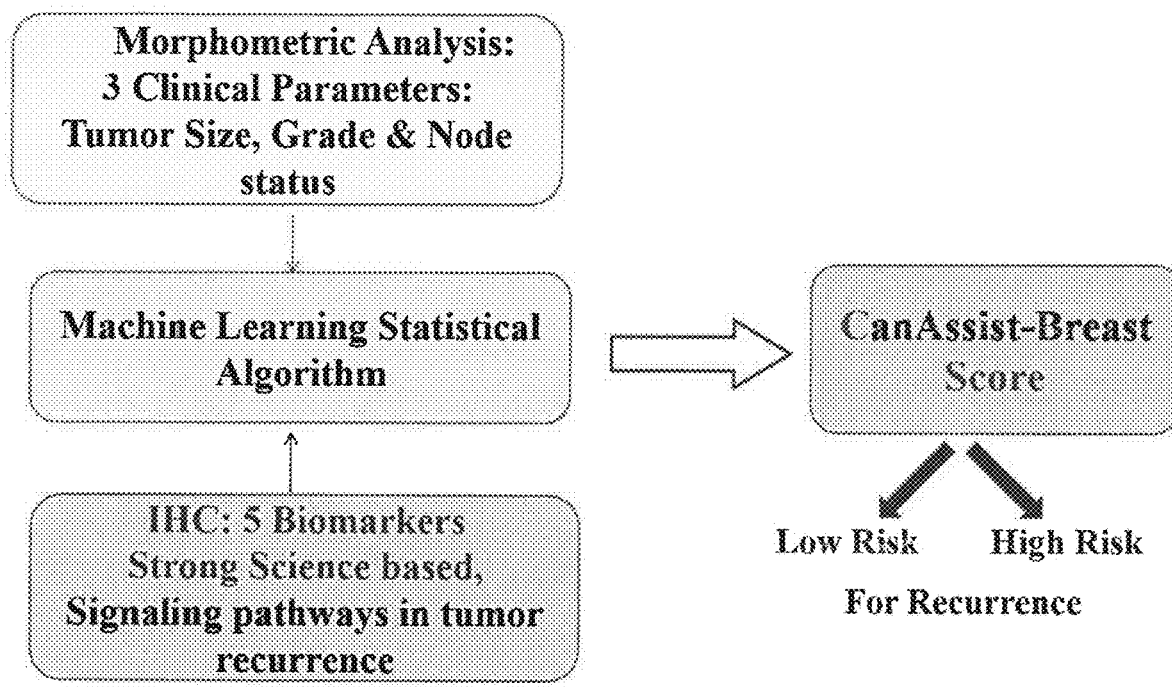
FIG. 2 illustrates description of CanAssist-Breast

In preferred embodiments of the present disclosure, the IHC based assay quantifies expression of a 5 biomarker combination in the early stage ER+/PR+ and Her2− breast cancer patient sample. Said biomarker expression is considered along with 3 specific clinical prognostic factors/clinicopathological parameters by employing histopathological analysis, to classify patients into high risk or low risk of recurrence based on a CanAssist Breast score which is devised by a statistical algorithm (FIG. 2).

In preferred embodiments of the present disclosure, the clinical prognostic factors are selected from a group comprising, but not limiting to tumor size, node status and tumor grade, which are conventionally known and well understood by a person skilled in the art.

In an exemplary embodiment, the node status includes tumor node positive and tumor node negative including N0 and N1, and tumor grade includes Grades 1, 2 and 3 according to the Bloom-Richardson-Elston criteria and tumor size as T1, T2, or T3 according to the TNM classification of Breast Cancer.

In further preferred embodiments of the present disclosure, the CanAssist Breast score or relapse score is an estimate of the patient's risk of recurrence that is based on combined expression of the marker combination along with the clinical factors, which is computed based on a machine-learning statistical algorithm or module. The algorithm or composite module of the present disclosure relates to a machine learning based risk classifier which stratifies patients as low or high risk of recurrence within 5 years from diagnosis. The relapse score is computed on a scale of 1-100 and scores of 15.5 and below are classified as low risk, and above 15.5 are classified as high risk.

The CanAssist-Breast algorithm/algorithm of the present disclosure is constructed/developed in a series of steps which are defined as follows:
1) Formulation of the problem,
2) Pre-processing of raw data,
3) Classifier selection and assessment, and
4) Selection of the final 5 biomarkers and 3 clinical parameters.

In embodiments of the present disclosure, the algorithm development includes:

Formulation of the Problem—

The problem of predicting breast cancer recurrence within five years (prognostic problem) is formulated as a binary classification problem with two outcomes, Recurrence and No Recurrence. The goal is to develop a classifier which computes a relapse score (also called CanAssist-Breast score) (a number between 0 and 100) which corresponds to five-year probability of recurrence for the given patient. State-of-the-art machine learning methodology is used to solve this problem.

Pre-Processing of Raw Data:

The raw training set data consists of about 298 samples which are represented by 57 IHC measurements or features (where each feature corresponds to a marker, and its staining pattern which is evaluated based on location, intensity and % of staining) and clinical variables/parameters/clinical prognostic factors (grade, age and TNM status). The dataset contains about 68 recurred samples (breast cancer recurrence within five years) and about 230 non-recurred samples (breast cancer recurrence-free within five years). The raw data is pre-processed as follows:

- TNM codes are converted into three discrete variables (size, number of nodes, metastasis status)
- the discrete variables (TNM and grade) are one-hot encoded
- all variables are centered-scaled to zero mean and unit standard deviation Subsequently, classifier assessment proceeds as per the well-defined statistical learning paradigm involving cross-validation for the assessment of statistical predictions.

A representative set of the complete training set is provided herewith by way of table no. 3 (cumulative of tables 3A, 3B, 3C and 3D), wherein IHC measurements are provided for 160 data samples.

Classifier Selection and Assessment: The classifier selection considers two types of parameters: internal ("weights") and external ("hyperparameters"). The external hyperparameters that are selected include cost, number of variables used in the classifier, and decision threshold. The internal parameters are selected using core classifier algorithms such as Support Vector Machine, Random Forest and Deep Learning. External hyperparameter selection is more complex, and includes an extensive grid search over a plausible set of values of the hyperparameters. For each fixed hyperparameter n-tuple, the performance of the classifier is computed using repeated cross-validation.

The following classifiers are evaluated: 1) Support Vector Machine (SVM) with linear and Radial Basis Function (RBF) kernel 2) Random Forest 3) ElasticNet [ESL] 4) multi-layer perceptron 5) normal mixture modeling.

Model selection is performed using Receiver Operator Graph (ROG) whereby each classifier is represented by its sensitivity and specificity. The principal model selection criterion is maximum sensitivity among classifiers with greater than 90% specificity. The ROG displays a potentially large family of classifiers which cover the full grid of external parameters, and the statistics are computed using cross-validation. The RBF SVM proved superior by the selected criteria (sensitivity and specificity) and is therefore selected for model assessment. This problem is also evaluated as a survival problem, whereby the goal is to estimate actual probability of survival at various time points for a given patient. A regularized Cox model is used in this approach. However, as this approach proved inferior to the performance achieved by the classifiers, it is not carried forward.

Selection of the Final 5 Biomarkers:

The training set is evaluated for a total of 41 biomarkers (listed in table 1 below) most commonly associated in the literature with the type of breast cancer provided by the present disclosure. However, no meaningful relevance was observed for 24 biomarkers with respect to their ability in being prognostic in nature. The data for the remaining 17 markers was analyzed more closely for the training set, and based on the interplay of markers, and their relevance in correlation with the prognosis of breast cancer, five distinct IHC markers are chosen to be part of the algorithm along with 3 clinical parameters/clinical prognostic factors. To select the markers, the markers are ranked by the absolute value of Pearson correlation coefficient between the marker value and the outcome (Recurrence/No Recurrence). This method is chosen, as no other marker selection algorithm matches or surpasses its performance. Each IHC marker corresponds to multiple IHC features (numeric values), since the protein levels are evaluated in the cell nucleus, cytoplasm and/or membrane. The marker selection process is integrated inside the cross-validation loop to avoid selection bias. The top 5 markers chosen from this list are as follows: CD44, Pan-Cadherin, N-Cadherin, ABCC11 and ABCC4.

TABLE 1

| Marker Code | Biomarkers |
|---|---|
| A | CD44 |
| B | CD24 |
| C | ABCG2 |
| D | ALDH1A1 |
| E | ESA |
| F | ABCC4 |
| G | CD133 |
| H | NANOG |
| I | Oct3/4 |
| J | SOX2 |
| K | APC |
| L | P-CADHERIN |
| M | HIF2A |
| N | THY1 |
| O | p-B-CATENIN |
| P | FOXA1 |
| Q | CD15 |
| R | ABCC11 |
| S1 | NESTIN |
| T | Ki67 |
| U | N-CADHERIN |
| V | E-CADHERIN |
| W | Pan-CADHERIN |
| X | Klf4 |
| Y | Alpha v beta 3 |
| Z | Klk6 |
| ZA | Total b-cat |
| ZB | MAGE-A9 |
| ZC | MAGE-A11 |
| ZD | CxCR4 |
| ZE | IFITM1 |
| ZF | Nrf2 |
| ZF | p-Nrf2 |
| ZG | CD147 |
| ZH | XBP1 |
| ZI | Notch 1 |
| ZJ | DLL-3 |
| ZK | GATA3 |
| ZL | HSP 70 |
| ZM | Integrin beta 6 |
| ZN | MDR1 |

Accurate risk stratification using the method of the present disclosure enables a physician to design an optimal therapeutic strategy for patients, i.e., patients who are stratified as low risk can be spared of chemotherapy and patients who are stratified as high risk to require adjuvant chemotherapy. The method of the present disclosure when compared to prior art prognostic tests is capable of separating high and low risk patients well, without having any intermediate risk category of patients, thus being accurate and capable of predicting all patients into either high/low risk of recurrence (FIG. 3).

The markers employed in the IHC based assay of the present disclosure function in molecular pathways other than hormone receptor regulation and proliferation. Said molecular pathways are involved in initiation and progression of breast cancer including apoptosis, self-renewal, angiogenesis, hypoxia, and drug resistance etc. Therefore, antigens towards these markers in the instant disclosure are from said molecular pathways and which are localized to different parts of a cell, not limiting to cell membrane. However, these markers have not been used in the art till date for breast cancer disease prognosis and recurrence prediction.

The IHC based assay of the present disclosure is developed and validated on both tumor node negative and tumor node positive patients from tumor stage ranging from Stage I to Stage IIIA and hence is a broad spectrum assay. The IHC based assay of the present disclosure is developed and validated on Hormone receptor positive (ER$^+$ and/or PR$^+$) and Her2 −ve samples. In other words, the IHC based assay of the present disclosure is applicable for patient samples where at least one of or both of ER and PR are +ve; and Her2 is −ve.

The method of identifying unique biomarker combination and employing the same for possible prognosis of breast cancer recurrence has been devised through rigorous experimentation and research and carefully studying the data sets over a period of more than 5 years, which involved biomarker selection and analysis in training samples set by employing IHC assay for biomarker combination shortlisting; testing for presence of shortlisted biomarker combination and clinicopathological parameters; followed by clinical validation of test-samples for predicting breast cancer recurrence.

The training sample set of the present disclosure relates to patient tumor samples of 298 patients, which satisfied the inclusion criteria of the present disclosure and includes samples of women having invasive ductal or lobular carcinoma of the breast; tumor stage I, II and III, and Age of the patient being preferably below 74 years; Positive for expression of hormone receptor ER and/or PR; Negative for expression of Her2 status; having minimum of 5 years follow-up and known clinical outcome data. This training sample set in the present disclosure is analyzed by IHC for ~41 gene-biomarker expression, most commonly associated with breast cancer in the literature. Based on the relevance of the markers in prognosis of breast cancer vis-à-vis the patient outcome, 17 markers were shortlisted for final screening and analysis. Each biomarker is graded quantitatively and this data along with three clinical parameters/clinical prognostic factors viz tumor size, tumor grade and node status is analyzed by the Statistician using Support Vector Machine based model. 5 biomarkers are shortlisted for their consistent prognostic ability and an algorithm is developed using staining intensity (0-3) and percentage of staining (0-100) of said 5 biomarkers in conjunction with three clinical prognostic parameters. The algorithm developed gives a certain score ranging from 1-100 to each patient's tumor sample, and if the score is under the cutoff point then the patient has a low probability of distant recurrence in the first 5 years and if the score is higher than the cut-off point, then the patient has a higher probability of distant recurrence.

The predictive ability of the 5 biomarker plus 3 clinical parameter combination arrived at from the training sample is further validated with a validation sample set. The validation sample set comprises patient tumor samples of around 700 patients, which again satisfy the inclusion criteria as aforementioned except that tumor stage was restricted until Stage 3A. The validation sample of the present disclosure is analyzed by IHC for the shortlisted 5 biomarker combination and information on percentage staining and biomarker staining intensity in conjunction with 3 clinical prognostic parameters is assessed with the statistical algorithm, for risk stratification. Results from the said analysis are compared with the known outcomes for each sample (from the patient history provided for each of the patients in validation set) to determine the accuracy of the 5 biomarker plus 3 clinical parameter combination. A representative set of the complete validation set is provided herewith by way of table no. 4, wherein IHC measurements are provided for 299 data samples.

In some embodiments of the present disclosure, the biomarker selection and analysis by IHC assay involves shortlisting about 17 proteins belonging to different molecular pathways involved in initiation and progression of breast cancer including apoptosis, self-renewal, angiogenesis, hypoxia and drug-resistance. Analyzing expression of these 17 genes in patients samples (Training set for 298 patient samples: having minimum 5 year follow-up data and known clinical outcome) is done by employing IHC, wherein the IHC assay involves analysis by observing the patient sample slides and scoring/grading of the samples based on percentage tumor stained and staining intensity for all the about 17 genes and further analyzing the scoring/grading data using known statistical tools and shortlisting most significant biomarker combination of 5 genes of the present disclosure. The 5 biomarkers analyzed by the IHC based assay of the present disclosure are CD44, ABCC11, N-cadherin, Pan-cadherin and ABCC4.

In a preferred embodiment, the selection/inclusion criteria for the training patient set samples involve selection of samples which are positive for hormone receptor status ER and/or PR; negative for Her2 status; and positive or negative for tumor node status; and tumor stage ranging from stage I, II, or IIIA.

In exemplary embodiments of the present disclosure, the statistical tools involve, multivariate analysis, Cox regression, Lasso and SVM models.

The present disclosure thus relates to a prognostic test which analyses the expression of a combination of five markers CD44, ABCC11, N-cadherin, Pan-cadherin and ABCC4 for detecting cancer recurrence in early stage ER+/PR+ and Her2− breast cancer as well as a predictive test which will enable devising of new drugs or personalized therapy specifically based on the prognostic outcome of the patient.

The present disclosure thus provides a tool for analyzing expression of 5 markers, i.e., CD44, ABCC11, N-cadherin, Pan-cadherin and ABCC4 and three clinical parameters thereby helping in stratifying the early stage ER+/PR+ and Her2− breast cancer patients into low or high risk of breast cancer recurrence.

In a non-limiting embodiment, the risk of recurrence is high if the CanAssist Breast score is higher than designated cut off point or low if the CanAssist Breast score is less than the designated cut off point.

In a preferred embodiments of the present disclosure, the testing of validation samples is done by employing the composite module or algorithm which takes into consideration and computes the expression of 5 most relevant biomarker combination data (which is based on the IHC analysis data of the training-set) in combination with the 3 clinicopathological parameters/clinical prognostic factors, for risk stratification of samples. The clinical validation of samples for breast cancer prognosis involves employing about 700 test samples of breast cancer in a retrospective study with the same inclusion criteria as for the training set and analyzing the test samples by the composite algorithm/module of the instant disclosure, which enables predicting the risk of distant recurrence in patients with early stage ER+/PR+ and Her2− stage breast cancer and thereby validating by comparing the same with actual outcomes of the respective patient history data.

In preferred embodiments of the present disclosure, manual grading is carried out before inputting the data in the statistical algorithm or module and the grading comprises of assessing the percentage of staining along with the intensity of staining of each of the biomarkers. The statistical algorithm or module employed in the present disclosure considers the grading values of % of staining and intensity of staining and clinical prognostic parameters of a sample and arrives at a predictive score.

In preferred embodiments of the present disclosure, the method of prognosis of the instant disclosure provides significant prognosis of breast cancer risk recurrence in terms of providing NPV (negative predictive value) of about 95%, when compared with the patient history data available.

In an exemplary embodiment, the validation study module of the instant disclosure is set forth in order below:
1. Conducting model retrospective validation study on additional 700 breast cancer patients (Stages I-IIIA).
2. IHC is performed on the tumor blocks for selected 5 markers.
3. 'CanAssist Breast relapse score' is calculated based on the IHC results and 3 clinical parameters using the composite algorithm/Breast model equation.
4. Predicted 'risk of recurrence'/results are compared with actual outcomes confirming the prediction.

The present disclosure, further relates to a method of identifying expression of biological marker combination on cells in a biological sample being or suspected of being a early stage tumor/cancer, said method comprising acts of:
 a) collecting, fixing, sectioning and treating the biological sample (which fulfills all the inclusion criteria as provided by the instant invention) with IHC reagents, followed by antigen retrieval using predetermined buffer solution and heat and adding primary antibody against ER/PR and/or Her-2-neu receptor (in case the ER/PR/Her-2-neu status is not previously known) followed by antibodies against biological marker combination of CD44, ABCC11, N-cadherin, Pan-cadherin and ABCC4; and
 b) adding secondary antibody conjugated with an enzyme and reagents for obtaining a colored reaction (i.e: substrate specific to the enzyme) or fluorescence for identifying positive expression of the hormonal receptors ER and/or PR; and biological marker combination.

Preferably, the present disclosure relates to a method of identifying expression of biological marker combination on cells in a biological sample, having one or both of ER and PR positive, and Her-2-neu negative, being or suspected of being a tumor/cancer, said method comprising acts of:
 a) collecting, fixing, sectioning and treating the biological sample (which fulfills all the inclusion criteria as provided by the instant invention) with IHC reagents, followed by antigen retrieval using predetermined buffer solution and heat and adding antibodies against biological marker combination of CD44, ABCC11, N-cadherin, Pan-cadherin and ABCC4; and
 b) adding secondary antibody conjugated with an enzyme and reagents for obtaining a colored reaction (i.e: substrate specific to the enzyme) or fluorescence for identifying expression of the biological marker combination.

The biological samples are first checked for presence of ER and/or PR receptors and for absence of Her-2-neu receptors by IHC assay and only if the samples match the inclusion criteria of the instant invention and presence of ER$^+$ and/or PR$^+$ receptor status is confirmed (along with absence of Her-2-neu), said samples are considered for biomarker combination expression using IHC assay. The samples are not tested for the 5 biomarker combination of the instant invention, if the hormone receptor status is found negative for both ER and PR expression. Alternatively, if the status of ER/PR/Her-2-neu receptors on the samples are already/previously known, the samples can directly be tested for the 5 biomarker combination of the present disclosure.

In another non-limiting embodiment of the present disclosure, the collecting, fixing, sectioning and treating is carried out under predetermined conditions by conventional immunohistochemistry technique. All possible ways and means to carry out immunohistochemistry known to a person skilled in the art is envisaged by the method and assay of the present disclosure.

In another non-limiting embodiment of the present disclosure, the samples are subjected to H&E (Haemotoxylin and Eosin) staining to measure the tumor content before the IHC assay of the present disclosure is performed.

In exemplary embodiments of the present disclosure, the process of identifying the biomarker in patient samples is carried out by collecting the tumor sample from the patients having inclusion criteria mentioned above. The sample is processed using formalin and other organic solvents and then embedded in paraffin to make a block; and the block is sectioned on a slide. The slide is then passed through a series of organic solvents to rehydrate the tumor. Thereafter, antigen retrieval is carried out under controlled experimental conditions, using specific buffer solutions and heat by Multiple Epitope Retrieval System (MERS) or water bath at 90° C. This is followed by cooling the section on the slide to room temperature (RT), followed by adding a blocking agent. This is followed by adding of primary antibody against the antigen of interest; which is in turn followed by addition of secondary antibody conjugated with an enzyme. Finally, appropriate reagents are added for obtaining a coloured reaction. The staining of the section is observed for identification of percentage of staining and intensity of staining, optionally along with location of staining for biomarker expression in patient tumor/cancer samples. Thus, IHC reagents employed in the present disclosure include at least one of xylene, isopropanol, ethanol, buffer solutions, protein blocking agents, primary antibodies, secondary antibodies labeled with enzymes such as horseradish peroxidase (HRP) or alkaline phosphatase (AP) or with fluorescent tags such as fluorescein isothiocyanate (FITC) or phycoerythrin (PE) or with molecule biotin/streptavidin, and substrates such as diamino benzydene (DAB) or p-nitrophenyl phosphate (PNPP).

Once the biological sample was identified for the ER/PR and/or Her-2-neu and found positive for ER and/or PR and negative for Her-2-neu by employing IHC assay, such samples were identified for 5 biomarker combination expression and scored for percentage of tumors stained (0-100) and staining intensity (0-3) again by using IHC assay. Alternatively, if the biological sample is already known to be ER+ and/or PR+ and Her-2-neu −ve, IHC assay is directly performed to identify expression of 5 biomarker combination of the present disclosure. Manual grading is carried out before inputting the data in the statistical algorithm or module and the grading comprises computing the percentage of staining along with the intensity of staining of each of the biomarkers. This IHC based data was analyzed using various statistical tools and information obtained therefrom was fed into a statistical algorithm along with 3 clinicopathological parameters data, for breast cancer risk stratification.

The present disclosure further relates to a method of prognosis of a subject having cancer or suspected of having early stage ER+/PR+ and Her2− breast cancer for cancer recurrence, said method comprising acts of:
a) collecting biological sample from the subject having positive expression of at least one receptor selected from a group comprising estrogen receptor and progesterone receptor and absence of Her-2-neu receptor in cells of the sample;
b) carrying out IHC analysis on the cells of step (a) with antibody against biological marker combination of CD44, ABCC11, N-cadherin, Pan-cadherin and ABCC4;
c) identifying expression of the biological marker combination along with clinical prognostic parameters; and
d) inputting this information in a statistical algorithm or module for predicting the prognosis of the subject (FIG. 4).

In embodiments of the present disclosure, the immunohistochemistry analysis is carried out by conventional method and wherein the identification of markers is carried out by visualizing a colored reaction or fluorescence obtained at completion of the method due to staining of the cells from the sample.

In further embodiments of the present disclosure, parameters employed for analyzing expression of biomarkers are selected from a group comprising percentage of staining, intensity of staining and optionally location of staining or any combination thereof; and wherein the location of the staining is selected from a group comprising cell membrane, cytoplasm and nucleus or any combination thereof.

In further embodiments of the present disclosure, manual grading is carried out before inputting the data in a statistical algorithm or module and the grading comprises computing the percentage of staining along with the intensity of staining of each of the biomarkers. The statistical algorithm or module employed in the present disclosure considers the grading scores and clinical prognostic parameters of a sample and arrives at a predictive score, in order to predict the prognosis as being high risk or low risk for breast cancer recurrence. The statistical algorithm or module computes the prediction score by taking into account the expression data of the 5 biomarker combination and clinical prognostic parameters (which is devised from the retrospective study on training set and respective patient history data).

Thus, the present disclosure provides an assay or a tool for prognosis of breast cancer recurrence by studying and analyzing expression of a specific combination of biomarkers along with clinical prognostic parameters. The assay is performed by carrying out an immunohistochemistry based method which helps in studying and analyzing said expression of biomarkers. Initially, as an optional step, the assay or method provides for identification of estrogen receptor and/or progesterone receptor, and proceeds to the next step only if one or both of the receptors are present. However, if the information on status of estrogen receptor and/or progesterone receptor is already known for a sample/patient, this step is not performed. In the next step, the assay provides for identification of expression of biomarkers CD44, ABCC11, N-cadherin, Pan-cadherin and ABCC4; preferably 5 biomarker combination of CD44, ABCC11, N-cadherin, Pan-cadherin and ABCC4, followed by grading the expression on the basis of parameters including percentage of staining and intensity of staining. The data from said grading along with status of clinical prognostic parameters is inputted into a proprietary statistical algorithm or module for obtaining a prediction score. The proprietary statistical algorithm or module is built on the basis of data obtained by retrospective study of 298 patient samples (training set) and comprises of expression data pertaining to each of the 5 biomarkers and clinical prognostic parameters. Since the retrospective study takes into consideration the patient history of all the samples, the expression data is calculated by the algorithm or module accordingly and a relapse score is computed. The relapse score is computed on a scale of 1-100 and scores of 15.5 and below are classified as low risk, and above 15.5 are classified as high risk. Lastly, the prediction score stratifies the respective patient into low risk or high risk category, based on the prediction of the prognosis of the subject. The patients are classified as high risk if the patient is expected to have >9% probability of distant recurrence within five years of initial treatment of breast cancer. Similarly, the patients are classified as low risk if the patient is expected to have 9% or lower probability of distant recurrence of breast tumor within five years of initial treatment of breast cancer. The cutoff of 9% risk of recurrence for 'low risk' patients is line with population recurrence rate of 10% and is lower than what similar prognostic tests offer for their low risk categories. As it can be understood lower the cutoff for the low risk category, higher would be usefulness of the same.

The present disclosure also relates to marker(s) employed in the method of prognosis of the instant disclosure, which are CD44, ABCC11, N-cadherin, Pan-cadherin and ABCC4.

In preferred embodiments of the present disclosure, the marker acts as a bio-marker for prognosis of cancer recurrence in patients having breast cancer or suspected of having breast cancer.

In preferred embodiments of the present disclosure, the marker(s) of the instant disclosure are employed in combination for breast cancer prognosis.

The present disclosure also relates to method of using the markers of the present disclosure for prognosis of breast cancer in samples of patients having breast cancer or suspected of having breast cancer.

The present disclosure also relates to a kit for prognosis of a subject having early stage ER+/PR+ and Her2− breast cancer or suspected of having early stage ER+/PR+ and Her2-breast cancer, said kit comprising antibody against biological markers CD44, ABCC11, N-cadherin, Pan-cadherin and ABCC4, optionally along with at least one member from IHC reagents such as xylene, isopropanol, ethanol, buffer solutions, protein blocking agents, primary antibodies, secondary antibodies labeled with enzymes such as horseradish peroxidase (HRP) or alkaline phosphatase (AP) or with fluorescent tags such as fluorescein isothiocyanate (FITC) or phycoerythrin (PE) or with molecule biotin/streptavidin, and substrates such as diamino benzydene (DAB) or p-nitrophenyl phosphate (PNPP), for performing immunohistochemistry and instruction manual.

A more complete understanding can be obtained by reference to the following specific examples, which are provided for purposes of illustration only and are not intended to limit the scope of the disclosure.

EXAMPLES

Biomarkers & Antibodies

The biomarkers and antibodies against said biomarker being used in the instant disclosure are selected from one or more of the following:

CD44; ABCC11; N-cadherin; Pan-cadherin; ABCC4. These antibodies are purchased from reputed Antibody manufacturers including Thermo Scientific, Novus, Abnova Spring, and AbCam.

The organic solvents, reagents (buffer, detergent etc), secondary antibody and enzymes (substrate specific to the enzyme), mentioned in the detailed protocol below are only for the purposes of illustration and should not be construed to be limiting in nature. The instant disclosure envisages and encompasses all possible combinations and alternatives of such solvents, reagents/substrates, secondary antibody and enzymes known and commonly used by a person skilled in the art.

Furthermore, the abbreviations referred in the instant disclosure have the following meaning (table no. 2):

TABLE 2

| Column Name | Description |
| --- | --- |
| Outcome | 1—Good Outcome/No recurrence |
|  | 0—Bad Outcome/Recurrence |
| Sample No. | Unique patient code |
|  | T—Tumor size (0-n) |
| TNM | N—Node status (0-n) |
|  | M—Metastases |
|  | (present—1, absent—0, unknown—x) |
| Stage | Stage of disease based on TNM at the time of diagnosis |
| Age | Age of patient at the time of diagnosis |
| ER | Percentage expression of Estrogen Receptor in Nucleus of tumor cells |
| ER-I | Intensity of marker Estrogen Receptor expression in Nucleus of tumor cells |
| PR | Percentage expression of Progesterone Receptor in Nucleus of tumor cells |
| PR-I | Intensity of marker Progesterone Receptor expression in Nucleus of tumor cells |
| Her-2 | Her-2-neu Status |
|  | 0—Negative |
|  | 1—Positive |
| A %-M | Percentage expression of marker A on Membrane of tumor cells |
| AI-M | Intensity of marker A expression on Membrane of tumor cells |
| C %-C | Percentage expression of marker C in Cytoplasm of tumor cells |
| CI-C | Intensity of marker C expression in Cytoplasm of tumor cells |
| C %-N | Percentage expression of marker C in Nucleus of tumor cells |
| CI-N | Intensity of marker C expression Nucleus of tumor cells |
| F %-M | Percentage expression of marker F on Membrane of tumor cells |
| FI-M | Intensity of marker F expression on Membrane of tumor cells |
| F %-C | Percentage expression of marker F in Cytoplasm of tumor cells |
| FI-C | Intensity of marker F expression in Cytoplasm of tumor cells |
| K %-M | Percentage expression of marker K on Membrane of tumor cells |
| KI-M | Intensity of marker K expression on Membrane of tumor cells |
| K %-C | Percentage expression of marker K in Cytoplasm of tumor cells |
| KI-C | Intensity of marker K expression in Cytoplasm of tumor cells |
| M %-C | Percentage expression of marker M in Cytoplasm of tumor cells |
| MI-C | Intensity of marker M expression in Cytoplasm of tumor cells |
| N %-C | Percentage expression of marker N in Cytoplasm of tumor cells |
| NI-C | Intensity of marker N expression in Cytoplasm of tumor cells |
| O %-M | Percentage expression of marker O on Membrane of tumor cells |
| OI-M | Intensity of marker O expression on Membrane of tumor cells |
| P %-N | Percentage expression of marker P in Nucleus of tumor cells |
| PI-N | Intensity of marker P expression Nucleus of tumor cells |
| R %-M | Percentage expression of marker R on Membrane of tumor cells |
| RI-M | Intensity of marker R expression on Membrane of tumor cells |
| R %-C | Percentage expression of marker R in Cytoplasm of tumor cells |
| RI-C | Intensity of marker R expression in Cytoplasm of tumor cells |
| U %-M | Percentage expression of marker U on Membrane of tumor cells |
| UI-M | Intensity of marker U expression on Membrane of tumor cells |
| U %-C | Percentage expression of marker U in Cytoplasm of tumor cells |
| UI-C | Intensity of marker U expression in Cytoplasm of tumor cells |
| V %-M | Percentage expression of marker V on Membrane of tumor cells |
| VI-M | Intensity of marker V expression on Membrane of tumor cells |
| V %-C | Percentage expression of marker V in Cytoplasm of tumor cells |
| VI-C | Intensity of marker V expression in Cytoplasm of tumor cells |
| W %-M | Percentage expression of marker W on Membrane of tumor cells |
| WI-M | Intensity of marker W expression on Membrane of tumor cells |
| W %-C | Percentage expression of marker W in Cytoplasm of tumor cells |
| WI-C | Intensity of marker W expression in Cytoplasm of tumor cells |
| ZA1 %-M | Percentage expression of marker ZA1 on Membrane of tumor cells |
| ZA1I-M | Intensity of marker ZA1 expression on Membrane of tumor cells |
| ZA1 %-C | Percentage expression of marker ZA1 in Cytoplasm of tumor cells |
| ZA1I-C | Intensity of marker ZA1 expression in Cytoplasm of tumor cells |
| ZB %-C | Percentage expression of marker ZB in Cytoplasm of tumor cells |
| ZBI-C | Intensity of marker ZB expression in Cytoplasm of tumor cells |
| ZC %-M | Percentage expression of marker ZC on Membrane of tumor cells |

TABLE 2-continued

| Column Name | Description |
|---|---|
| ZCI-M | Intensity of marker ZC expression on Membrane of tumor cells |
| ZC %-C | Percentage expression of marker ZC in Cytoplasm of tumor cells |
| ZCI-C | Intensity of marker ZC expression in Cytoplasm of tumor cells |
| ZD %-C | Percentage expression of marker ZD in Cytoplasm of tumor cells |
| ZDI-C | Intensity of marker ZD expression in Cytoplasm of tumor cells |
| ZF2 %-N | Percentage expression of marker ZF2 in Nucleus of tumor cells |
| ZF2I-N | Intensity of marker ZF2 expression Nucleus of tumor cells |
| Date of Diagnosis | Date of diagnosis of breast cancer |
| Date of Last follow up | Date of latest visit of patient at the hospital |
| Date of Death | Date of Death of patient due to disease |
| Current Status | Current Status<br>0—Dead<br>1—Alive |
| Status Unknown | Current status is unknown |
| DFS (in months) | DFS: Disease Free Survival (in months) |
| TTP 1st Recurrence (in months) | TTP: Time to Tumor Progression 1st Recurrence (in months) |
| Date of 1st Recurrence | Date of diagnosis of 1st recurrence |
| Location of 1st Recurrence | Site of 1st recurrence Eg: Lung, Liver, brain |
| TTP 2nd Recurrence (in months) | TIP: Time to Tumor Progression 2nd Recurrence (in months) |
| Date of 2nd Recurrence | Date of diagnosis of 2nd recurrence |
| Location of 2nd Recurrence | Site of 2nd recurrence Eg; Lung, Liver, brain |
| TTP 3rd Recurrence (in mouths) | TIP: Time to Tumor Progression 3rd Recurrence in months) |
| Date of 3rd Recurrence | Date of diagnosis of 3rd recurrence |
| Location of 3rd Recurrence | Site of 3rd recurrence Eg: Lung, Liver, brain |
| TTP 4th Recurrence (in months) | TTP: Time to Tumor Progression 4th Recurrence (in months) |
| Date of 4th Recurrence | Date of diagnosis of 4th recurrence |
| Location of 4th Recurrence | Site of 4th recurrence Eg: Lung, Liver, brain |

Examples 1: Identification and Development of 5 Biomarker Combination of the Present Disclosure Sample Selection and H&E Staining All studies are performed with approval of the Institutional Review Board and Ethics Committees of the Hospitals participating in the study. Informed consent is waived according to Indian Council of Medical Research (ICMR) guidelines since the study is retrospective, observational, non-interventional and anonymized. For the present study, women with Stage I, II and III Invasive Ductal Carcinoma (IDC) of the Breast, Aged <74, ER+ve and/or PR+ve, Her2−ve, with minimum 5-year follow up and known clinical outcome are considered. Majority of the patients are in Stage II. All patient samples are stripped of personal identifiers, information is collected on age and calendar year of diagnosis, surgery, tumor (size, grade, histologic type, and ER status), nodal status, radiation treatment, hormonal therapy and chemotherapy, and clinical follow-up, including local, loco-regional, or distant recurrences, second primary malignancies, and death or date of last visit. Primary breast tumor surgical samples less than 15 years old (from either Modified Radical Mastectomy or Breast Conserving Surgery) are used.

H&E staining was carried out to ensure that samples mandatorily have a major component of IDC, and have at least 30% tumor content. Samples with extensive necrosis, crush artifacts, poorly processed tissue, only DCIS component and singly scattered cells are excluded.

ER/PR staining is carried out for all samples, and only those samples that are ER+ and/or PR+ are included.

IHC Assay in the Prognostic Test of the Instant Disclosure and Development of the CanAssist Breast Algorithm A total of 298 tumor samples having the inclusion criteria mentioned above are considered for the IHC assay. The technique used for the identification of markers in a patient sample in the present disclosure involves Immunohistochemistry (IHC).

The process of identifying the biomarker in patient samples is carried out using the technique as below:

1. Tumor sample is collected from the patients identified above. The sample is processed using formalin and other organic solvents and then embedded in paraffin to make a block;

2. The block is sectioned on a slide;

3. The slide is passed through a series of organic solvents to rehydrate the tumor;

4. Antigen retrieval is carried out under controlled experimental conditions, using specific buffer solution and heat, using Multiple Epitope Retrieval System (MERS) or Water Bath at 90° C.;

5. This is followed by cooling the section on the slide to room temperature (RT);

6. Followed by adding blocking agent;

7. Followed by adding of primary antibody against the antigen of interest;

8. Followed by adding of secondary antibody conjugated with an enzyme;

9. Followed by adding of reagents for obtaining a coloured reaction; and

10. Observing staining for grading of % of staining and intensity of staining, optionally along with location of staining for biomarker expression in patient tumor/cancer samples.

The above process is carried out and then repeated for identifying expression of each of the biomarkers in each sample. Initially, a total of 41 biomarkers most commonly associated in the literature with breast cancer are considered for screening each sample. However, no meaningful relevance was observed for 24 biomarkers with respect to their ability of being prognostic in nature. The data from the remaining 17 markers was analyzed in detail and used for the training set for determining critical biomarkers to be used for the Statistical algorithm development.

The stained slides (slides containing tumor section from training set samples stained with antibodies against each of the 17 markers) are thereafter analyzed manually by a Pathologist for scoring/grading Each sample is scored for percentage of tumors stained (0-100) and the staining intensity (0-3) for each of the markers. A representative set of the complete training set is provided herewith by way of table no. 3 (cumulative of tables 3A, 3B, 3C and 3D) wherein IHC measurements for each of the 17 markers are provided for 160 data samples, along with consideration of clinical prognostic parameters (tumor size, node status and tumor grade).

To select the most relevant prognostic markers, the markers are ranked by the absolute value of Pearson correlation coefficient between the marker value and the outcome (Recurrence/No Recurrence from the corresponding patient history). This method is chosen, as no other marker selection algorithm matches or surpasses its performance. Each IHC marker corresponds to multiple IHC features (numeric values), since the protein and intensity levels are evaluated in the cell nucleus, cytoplasm and/or membrane. The marker selection process is integrated inside the cross-validation loop to avoid selection bias. Based on comparison of scoring against the patient history available for each of the samples, a set of 5 most relevant biomarkers is selected for its ability of being prognostic in nature. These markers are CD44, ABCC11, N-cadherin, Pan-cadherin and ABCC4.

TABLE 3A

| SI. No. | Outcome | TNM | Grade | Stage | Age | ER | ER-I | PR | PR-I | Her-2 | A %-M | AI-M | C %-C | CI-C | C %-N | CI-N |
|---|---|---|---|---|---|---|---|---|---|---|---|---|---|---|---|---|
| 1 | 1 | T1N0M0 | 2 | 1 | 43 | 80 | 2 | 60 | 3 | 0 | 22.5 | 2 | 52.5 | 1.5 | 52.5 | 1.75 |
| 2 | 1 | T1N0M0 | 3 | 1 | 38 | 95 | 3 | 60 | 3 | 1 | 20 | 2 | 27.5 | 1.25 | 47.5 | 2 |
| 3 | 1 | T1N0M0 | 2 | 1 | 53 | 90 | 3 | 60 | 2 | 0 | 12.5 | 0.5 | 27.5 | 1 | 12.5 | 0.5 |
| 4 | 1 | T1N0M0 | 2 | 1 | 57 | 80 | 3 | 90 | 3 | 0 | 55 | 2 | 42.5 | 1.25 | 50 | 2 |
| 5 | 1 | T1N0M0 | 3 | 1 | 47 | 70 | 3 | 25 | 3 | 0 | 12.5 | 0.5 | 47.5 | 1.5 | 12.5 | 0.5 |
| 6 | 1 | T1N0M0 | 3 | 1 | 56 | 0 | 0 | 35 | 1 | 1 | 50 | 2 | 12.5 | 0.25 | 22.5 | 1 |
| 7 | 1 | T1N0M0 | 2 | 1 | 43 | 95 | 3 | 80 | 3 | 1 | 57.5 | 2 | 22.5 | 0.75 | 50 | 2 |
| 8 | 1 | T1N0M0 | 2 | 1 | 56 | 50 | 2 | 50 | 3 | 0 | 47.5 | 2 | 25 | 1 | 32.5 | 1.75 |
| 9 | 1 | T1N0M0 | 2 | 1 | 73 | 80 | 3 | 90 | 3 | 0 | 25 | 1.25 | 35 | 1.25 | 35 | 1.5 |
| 10 | 1 | T1N0M0 | 2 | 1 | 54 | 80 | 3 | 90 | 3 | 0 | 57.5 | 1.5 | 12.5 | 0.25 | 57.5 | 1.5 |
| 11 | 1 | T1N0M0 | 1 | 1 | 53 | 80 | 2 | 90 | 3 | 0 | 50 | 2 | 37.5 | 0.75 | 22.5 | 1 |
| 12 | 1 | T1cN0M0 | 2 | 1 | 49 | 90 | 3 | 90 | 3 | 0 | 52.5 | 1.5 | 12.5 | 0.25 | 47.5 | 1.5 |
| 13 | 1 | T1cN0M0 | 1 | 1 | 41 | 83 | 3 | 80 | 3 | 0 | 47.5 | 1.75 | 12.5 | 0.25 | 25 | 1.25 |
| 14 | 1 | T1N0M0 | 3 | 1 | 59 | 70 | 3 | 0 | 0 | 0 | 27.5 | 1.25 | 45 | 0.75 | 30 | 1.25 |
| 15 | 1 | T1N0M0 | 2 | 1 | 51 | 80 | 2 | 50 | 2 | 0 | 12.5 | 0.5 | 52.5 | 1.75 | 12.5 | 0.5 |
| 16 | 1 | T1N0M0 | 2 | 1 | 60 | 35 | 1.5 | 0 | 0 | 0 | 27.5 | 1.5 | 45 | 1.25 | 12.5 | 0.5 |
| 17 | 1 | T1N0M0 | 3 | 1 | 57 | 75 | 2 | 50 | 2 | 0 | 12.5 | 0.5 | 37.5 | 1.5 | 12.5 | 0.5 |
| 18 | 1 | T1N0M0 | 2 | 1 | 33 | 40 | 2 | 5 | 2 | 0 | 17.5 | 0.75 | 50 | 1.25 | 12.5 | 0.5 |
| 19 | 1 | T1N0M0 | 1 | 1 | 47 | 75 | 2.5 | 90 | 3 | 0 | 22.5 | 1.5 | 52.5 | 1.5 | 12.5 | 0.5 |
| 20 | 1 | T1N0M0 | 2 | 1 | 65 | 80 | 2 | 0 | 0 | 1 | 52.5 | 1.5 | 52.5 | 1.5 | 12.5 | 0.5 |
| 21 | 1 | T1N0M0 | 2 | 1 | 37 | 20 | 1.5 | 70 | 2.5 | 0 | 17.5 | 1.5 | 25 | 1.25 | 12.5 | 0.5 |
| 22 | 1 | T1N0M0 | 2 | 1 | 37 | 80 | 2 | 25 | 2 | 0 | 17.5 | 1.5 | 45 | 1.5 | 12.5 | 0.5 |
| 23 | 1 | T1N0M0 | 2 | 1 | 35 | 75 | 2 | 70 | 2 | 0 | 27.5 | 1.5 | 50 | 1.25 | 12.5 | 0.5 |
| 24 | 1 | T1N0M0 | 2 | 1 | 47 | 90 | 3 | 90 | 3 | 0 | 50 | 1.5 | 52.5 | 1.5 | 12.5 | 0.5 |
| 25 | 1 | T2N0M0 | 2 | 2A | 58 | 60 | 3 | 30 | 3 | 0 | 27.5 | 2 | 12.5 | 0.25 | 42.5 | 1.75 |
| 26 | 1 | T2N0M0 | 2 | 2A | 26 | 75 | 3 | 100 | 3 | 0 | 22.5 | 1.75 | 12.5 | 0.25 | 50 | 2 |
| 27 | 1 | T2N0M0 | 3 | 2A | 54 | 95 | 3 | 95 | 3 | 1 | 32.5 | 1.75 | 52.5 | 1.5 | 12.5 | 0.5 |
| 28 | 1 | T2N0M0 | 3 | 2A | 61 | 75 | 3 | 0 | 0 | 1 | 22.5 | 1 | 47.5 | 1.5 | 12.5 | 0.5 |
| 29 | 1 | T2N0M0 | 3 | 2A | 54 | 90 | 3 | 20 | 3 | 0 | 30 | 1.75 | 47.5 | 1 | 55 | 1.5 |
| 30 | 1 | T2N0M0 | 2 | 2A | 48 | 75 | 2 | 90 | 3 | 1 | 30 | 1.5 | 57.5 | 1.5 | 12.5 | 0.5 |
| 31 | 1 | T2N0M0 | 2 | 2A | 54 | 100 | 3 | 100 | 3 | 0 | 12.5 | 0.5 | 57.5 | 1 | 57.5 | 2 |
| 32 | 1 | T2N0M0 | 2 | 2A | 23 | 65 | 3 | 10 | 3 | 1 | 12.5 | 0.5 | 52.5 | 1 | 37.5 | 1.5 |
| 33 | 1 | T2N0M0 | 3 | 2A | 62 | 70 | 3 | 0 | 0 | 0 | 17.5 | 1.25 | 47.5 | 1.25 | 57.5 | 2 |
| 34 | 1 | T2N0M0 | 3 | 2A | 46 | 30 | 2 | 0 | 0 | 0 | 32.5 | 2 | 22.5 | 1 | 17.5 | 2 |
| 35 | 1 | T2N0M0 | 3 | 2A | 64 | 80 | 3 | 10 | 3 | 1 | 17.5 | 1 | 47.5 | 1.25 | 42.5 | 1.5 |
| 36 | 1 | T2N0M0 | 2 | 2A | 63 | 90 | 3 | 90 | 3 | 1 | 12.5 | 0.5 | 60 | 1.25 | 42.5 | 1.5 |
| 37 | 1 | T2N0M0 | 3 | 2A | 49 | 5 | 3 | 0 | 0 | 1 | 20 | 1.25 | 37.5 | 1.25 | 42.5 | 1.5 |
| 38 | 1 | T2N0M0 | 3 | 2A | 54 | 90 | 3 | 70 | 3 | 0 | 12.5 | 0.5 | 32.5 | 1.25 | 22.5 | 1 |
| 39 | 1 | T2N0M0 | 2 | 2A | 66 | 10 | 1.5 | 40 | 2 | 0 | 30 | 2 | 27.5 | 1 | 27.5 | 1.5 |

TABLE 3A-continued

| SI. No. | Outcome | TNM | Grade | Stage | Age | ER | ER-I | PR | PR-I | Her-2 | A %-M | AI-M | C %-C | CI-C | C %-N | CI-N |
|---|---|---|---|---|---|---|---|---|---|---|---|---|---|---|---|---|
| 40 | 1 | T2N0M0 | 2 | 2A | 45 | 40 | 2 | 90 | 3 | 0 | 17.5 | 1.25 | 47.5 | 1.25 | 17.5 | 1.5 |
| 41 | 1 | T2N0M0 | 3 | 2A | 80 | 80 | 3 | 75 | 3 | 1 | 57.5 | 2 | 37.5 | 0.75 | 57.5 | 2 |
| 42 | 1 | T2N0M0 | 3 | 2A | 53 | 75 | 3 | 75 | 3 | 1 | 50 | 2 | 22.5 | 0.75 | 47.5 | 1.75 |
| 43 | 1 | T2N0M0 | 2 | 2A | 43 | 10 | 2 | 50 | 2 | 0 | 17.5 | 1.25 | 37.5 | 1.25 | 12.5 | 0.5 |
| 44 | 1 | T2N0M0 | 2 | 2A | 66 | 75 | 2 | 20 | 2 | 0 | 32.5 | 1.25 | 47.5 | 1.25 | 22.5 | 1.25 |
| 45 | 1 | T2N0M0 | 1 | 2A | 77 | 90 | 3 | 30 | 2.5 | 0 | 32.5 | 1.5 | 12.5 | 0.25 | 27.5 | 1.25 |
| 46 | 1 | T2N0M0 | 1 | 2A | 48 | 60 | 2.5 | 70 | 3 | 0 | 50 | 1.5 | 12.5 | 0.25 | 12.5 | 0.5 |
| 47 | 1 | T2N0M0 | 2 | 2A | 50 | 60 | 3 | 25 | 2 | 0 | 12.5 | 0.5 | 12.5 | 0.25 | 12.5 | 0.5 |
| 48 | 1 | T2N0M0 | 2 | 2A | 53 | 30 | 2 | 50 | 2 | 0 | 47.5 | 1.5 | 27.5 | 1 | 27.5 | 0.75 |
| 49 | 1 | T2N0M0 | 2 | 2A | 53 | 80 | 2.5 | 80 | 3 | 1 | 42.5 | 2 | 37.5 | 0.75 | 37.5 | 1 |
| 50 | 1 | T2N0M0 | 2 | 2A | 65 | 90 | 3 | 90 | 3 | 0 | 42.5 | 1 | 42.5 | 1.25 | 32.5 | 1.5 |
| 51 | 1 | T2N0M0 | 2 | 2A | 52 | 80 | 3 | 35 | 2 | 0 | 25 | 1 | 52.5 | 1.5 | 27.5 | 1 |
| 52 | 1 | T2N0M0 | 2 | 2A | 38 | 70 | 2 | 0 | 0 | 0 | 12.5 | 0.5 | 17.5 | 0.75 | 32.5 | 1.5 |
| 53 | 1 | T2N0M0 | 2 | 2A | 63 | 70 | 2.5 | 50 | 2 | 0 | 22.5 | 1.25 | 32.5 | 0.75 | 47.5 | 1.5 |
| 54 | 1 | T2N0M0 | 1 | 2A | 56 | 80 | 2.5 | 50 | 2 | 1 | 30 | 1.25 | 52.5 | 1.5 | 12.5 | 0.5 |
| 55 | 1 | T2N0M0 | 1 | 2A | 62 | 90 | 3 | 65 | 2.5 | 1 | 20 | 1.5 | 52.5 | 1.5 | 12.5 | 0.5 |
| 56 | 1 | T2N0M0 | 3 | 2A | 41 | 30 | 2 | 40 | 2.5 | 0 | 47.5 | 2 | 32.5 | 1 | 27.5 | 1.5 |
| 57 | 1 | T2N0M0 | 2 | 2A | 42 | 30 | 2 | 30 | 2 | 1 | 22.5 | 2 | 52.5 | 1.5 | 12.5 | 0.5 |
| 58 | 1 | T2N0M0 | 3 | 2A | 55 | 10 | 2 | 50 | 2 | 1 | 22.5 | 1.5 | 52.5 | 1.5 | 12.5 | 0.5 |
| 59 | 1 | T2N0M0 | 3 | 2A | 45 | 60 | 2 | 40 | 2 | 0 | 57.5 | 2 | 52.5 | 1.5 | 12.5 | 0.5 |
| 60 | 1 | T2N0M0 | 2 | 2A | 65 | 70 | 2 | 0 | 0 | 0 | 22.5 | 1 | 47.5 | 1.25 | 12.5 | 0.5 |
| 61 | 1 | T2N0M0 | 3 | 2A | 49 | 60 | 3 | 30 | 2 | 0 | 20 | 1.25 | 42.5 | 1.25 | 12.5 | 0.5 |
| 62 | 1 | T2N0M0 | 2 | 2A | 67 | 70 | 2.5 | 30 | 2.5 | 0 | 42.5 | 1.25 | 52.5 | 1.5 | 17.5 | 1.5 |
| 63 | 1 | T2N0M0 | 3 | 2A | 56 | 20 | 3 | 20 | 3 | 0 | 42.5 | 1.5 | 12.5 | 0.25 | 12.5 | 0.5 |
| 64 | 1 | T2N0M0 | 2 | 2A | 57 | 0 | 0 | 25 | 1.5 | 0 | 25 | 1.5 | 42.5 | 1.5 | 20 | 1.25 |
| 65 | 1 | T2N0M0 | 2 | 2A | 49 | 20 | 1.5 | 35 | 1.5 | 0 | 27.5 | 1.5 | 52.5 | 1.5 | 17.5 | 1.5 |
| 66 | 1 | T2N0M0 | 2 | 2A | 54 | 60 | 2 | 10 | 2 | 0 | 12.5 | 0.5 | 52.5 | 1.5 | 12.5 | 0.5 |
| 67 | 1 | T2N0M0 | 2 | 2A | 57 | 10 | 2 | 0 | 0 | 1 | 22.5 | 1 | 52.5 | 1 | 12.5 | 0.5 |
| 68 | 1 | T2N0M0 | 2 | 2A | 43 | 40 | 2.5 | 40 | 3 | 0 | 12.5 | 0.5 | 47.5 | 1.5 | 12.5 | 0.5 |
| 69 | 1 | T2N0M0 | 2 | 2A | 41 | 60 | 2.5 | 20 | 2.5 | 0 | 20 | 1.5 | 47.5 | 1.5 | 12.5 | 0.5 |
| 70 | 1 | T2N0M0 | 2 | 2A | 40 | 60 | 2.5 | 70 | 2.5 | 0 | 37.5 | 1.5 | 47.5 | 1 | 12.5 | 0.5 |
| 71 | 1 | T2N0M0 | 3 | 2A | 50 | 0 | 0 | 20 | 2 | 1 | 17.5 | 1.25 | 42.5 | 1.25 | 12.5 | 0.5 |
| 72 | 1 | T2N0M0 | 3 | 2A | 43 | 90 | 3 | 60 | 3 | 0 | 20 | 1 | 12.5 | 0.25 | 42.5 | 1.5 |
| 73 | 1 | T2N0M0 | 2 | 2A | 42 | 80 | 3 | 50 | 3 | 0 | 22.5 | 2 | 42.5 | 1.25 | 12.5 | 0.5 |
| 74 | 1 | T2NxM0 | 3 | 2A | 46 | 0 | 0 | 25 | 2.5 | 0 | 37.5 | 1.5 | 12.5 | 0.25 | 27.5 | 1.25 |
| 75 | 1 | T2N0M0 | 2 | 2A | 38 | 70 | 2 | 45 | 2 | 1 | 27.5 | 1.5 | 45 | 1.25 | 12.5 | 0.5 |
| 76 | 1 | T2N0M0 | 2 | 2A | 69 | 60 | 1.5 | 10 | 2 | 1 | 30 | 1.5 | 42.5 | 1.25 | 27.5 | 1.5 |
| 77 | 1 | T2N0M0 | 2 | 2A | 38 | 75 | 2 | 0 | 0 | 0 | 47.5 | 1.75 | 22.5 | 1 | 12.5 | 0.5 |
| 78 | 1 | T2N0M0 | 2 | 2A | 64 | 90 | 3 | 80 | 2 | 0 | 45 | 1.5 | 42.5 | 1.25 | 12.5 | 0.5 |
| 79 | 1 | T2N0M0 | 3 | 2A | 54 | 65 | 2.5 | 45 | 2 | 0 | 12.5 | 0.5 | 52.5 | 1.5 | 12.5 | 0.5 |
| 80 | 1 | T2N0M0 | 3 | 2A | 73 | 0 | 0 | 30 | 2 | 0 | 50 | 2 | 52.5 | 1.5 | 12.5 | 0.5 |
| 81 | 1 | T2N0M0 | 3 | 2A | 35 | 80 | 2.5 | 45 | 2.5 | 0 | 27.5 | 1 | 50 | 1.25 | 12.5 | 0.5 |
| 82 | 1 | T2N0M0 | 3 | 2A | 60 | 35 | 2 | 5 | 2 | 1 | 12.5 | 0.5 | 47.5 | 1 | 12.5 | 0.5 |
| 83 | 1 | T2N0M0 | 2 | 2A | 52 | 80 | 2 | 55 | 2 | 1 | 22.5 | 1.5 | 47.5 | 1.5 | 12.5 | 0.5 |
| 84 | 1 | T2N0M0 | 2 | 2A | 49 | 25 | 2 | 0 | 0 | 1 | 47.5 | 1.5 | 17.5 | 1.25 | 12.5 | 0.5 |
| 85 | 1 | T2N0M0 | 2 | 2A | 53 | 90 | 2.5 | 40 | 2 | 0 | 22.5 | 1.5 | 52.5 | 1.5 | 12.5 | 0.5 |
| 86 | 1 | T2N0M0 | 2 | 2A | 59 | 65 | 2.5 | 80 | 2.5 | 0 | 12.5 | 0.5 | 52.5 | 1.5 | 12.5 | 0.5 |
| 87 | 1 | T2N0M0 | 2 | 2A | 51 | 90 | 2.5 | 70 | 2 | 0 | 35 | 1.5 | 25 | 1 | 12.5 | 0.5 |
| 88 | 1 | T2N0M0 | 3 | 2A | 53 | 70 | 2.5 | 35 | 2 | 0 | 15 | 1.5 | 40 | 1.25 | 12.5 | 0.5 |
| 89 | 1 | T2N0M0 | 3 | 2A | 60 | 0 | 0 | 35 | 2 | 1 | 40 | 1.5 | 35 | 1.5 | 12.5 | 0.5 |
| 90 | 1 | T1N1M0 | 2 | 2A | 52 | 0 | 0 | 15 | 2 | 1 | 32.5 | 1.75 | 12.5 | 0.25 | 42.5 | 2 |
| 91 | 1 | T1N1M0 | 2 | 2A | 45 | 35 | 2 | 0 | 0 | 0 | 32.5 | 1.5 | 22.5 | 0.75 | 42.5 | 1.5 |
| 92 | 1 | T1N1M0 | 2 | 2A | 33 | 40 | 2 | 90 | 2.5 | 1 | 12.5 | 0.5 | 52.5 | 1.5 | 37.5 | 1.25 |
| 93 | 1 | T1N1M0 | 3 | 2A | 51 | 60 | 2.5 | 40 | 2 | 1 | 12.5 | 0.5 | 52.5 | 1.5 | 12.5 | 0.5 |
| 94 | 1 | T1N1M0 | 3 | 2A | 52 | 80 | 3 | 30 | 3 | 0 | 55 | 2 | 17.5 | 0.75 | 12.5 | 0.5 |
| 95 | 1 | T1N1M0 | 3 | 2A | 53 | 65 | 3 | 70 | 3 | 0 | 55 | 2 | 17.5 | 0.75 | 47.5 | 1.5 |
| 96 | 1 | T1N1M0 | 2 | 2A | 51 | 60 | 2 | 50 | 2 | 0 | 42.5 | 1.5 | 52.5 | 1.25 | 12.5 | 0.5 |
| 97 | 1 | T1N1M0 | 2 | 2A | 37 | 70 | 3 | 70 | 3 | 0 | 42.5 | 1.5 | 37.5 | 1 | 12.5 | 0.5 |
| 98 | 1 | T1N1M0 | 1 | 2A | 41 | 70 | 2.5 | 90 | 3 | 0 | 30 | 1.5 | 52.5 | 1.5 | 12.5 | 0.5 |
| 99 | 1 | T1N1M0 | 3 | 2A | 37 | 0 | 0 | 20 | 2 | 0 | 50 | 1.75 | 52.5 | 1.5 | 17.5 | 1.5 |
| 100 | 1 | T1N1M0 | 3 | 2A | 50 | 50 | 2 | 25 | 2.5 | 0 | 12.5 | 0.5 | 47.5 | 1.25 | 12.5 | 0.5 |
| 101 | 1 | T1N1M0 | 2 | 2A | 55 | 75 | 2 | 65 | 2 | 0 | 32.5 | 1.75 | 47.5 | 1.25 | 12.5 | 0.5 |
| 102 | 1 | T1N1M0 | 3 | 2A | 51 | 70 | 2.5 | 30 | 2.5 | 1 | 17.5 | 1.5 | 37.5 | 1.25 | 12.5 | 0.5 |
| 103 | 1 | T2N1M0 | 2 | 2A | 62 | 80 | 2.5 | 0 | 0 | 0 | 12.5 | 0.5 | 47.5 | 1.5 | 12.5 | 0.5 |
| 104 | 1 | T2N1M0 | 2 | 2A | 45 | 80 | 2.5 | 90 | 2 | 0 | 12.5 | 0.5 | 47.5 | 1 | 12.5 | 0.5 |
| 105 | 1 | T2N1M0 | 2 | 2A | 54 | 30 | 1.5 | 0 | 0 | 0 | 17.5 | 1.5 | 50 | 1.25 | 12.5 | 0.5 |
| 106 | 1 | T2N1M0 | 1 | 2A | 60 | 90 | 2.5 | 75 | 2.5 | 0 | 30 | 1.5 | 52.5 | 1.25 | 12.5 | 0.5 |
| 107 | 1 | T2N1M0 | 1 | 2A | 35 | 80 | 2.5 | 70 | 2 | 0 | 22.5 | 1.5 | 47.5 | 1.5 | 12.5 | 0.5 |
| 108 | 1 | T2N1M0 | 2 | 2A | 56 | 90 | 3 | 5 | 2.5 | 0 | 30 | 1.5 | 52.5 | 1.25 | 12.5 | 0.5 |
| 109 | 1 | T2N0M0 | 2 | 2A | 69 | 60 | 1.5 | 90 | 2.5 | 0 | 42.5 | 1.5 | 50 | 1.5 | 12.5 | 0.5 |
| 110 | 1 | T2N0M0 | 2 | 2A | 52 | 65 | 2 | 80 | 2.5 | 0 | 12.5 | 0.5 | 42.5 | 0.75 | 12.5 | 0.5 |
| 111 | 1 | T2N0M0 | 2 | 2A | 42 | 85 | 3 | 90 | 2.5 | 0 | 37.5 | 1.5 | 47.5 | 1.5 | 50 | 1.5 |
| 112 | 1 | T2N0M0 | 3 | 2A | 50 | 60 | 2 | 0 | 0 | 1 | 15 | 1.5 | 52.5 | 1.5 | 12.5 | 0.5 |
| 113 | 1 | T2N0M0 | 3 | 2A | 40 | 50 | 2 | 50 | 2 | 1 | 15 | 1.5 | 52.5 | 1.25 | 12.5 | 0.5 |
| 114 | 1 | T2N0M0 | 3 | 2A | 42 | 80 | 3 | 70 | 3 | 0 | 20 | 1.5 | 52.5 | 1.5 | 12.5 | 0.5 |
| 115 | 1 | T2N1M0 | 2 | 2B | 58 | 90 | 2.5 | 30 | 2 | 1 | 30 | 1.5 | 52.5 | 1.5 | 12.5 | 0.5 |
| 116 | 1 | T2N1M0 | 2 | 2B | 55 | 80 | 3 | 0 | 0 | 0 | 17.5 | 2 | 12.5 | 0.25 | 42.5 | 2 |

TABLE 3A-continued

| SI. No. | Outcome | TNM | Grade | Stage | Age | ER | ER-I | PR | PR-I | Her-2 | A %-M | AI-M | C %-C | CI-C | C %-N | CI-N |
|---|---|---|---|---|---|---|---|---|---|---|---|---|---|---|---|---|
| 117 | 1 | T2N1M0 | 3 | 2B | 36 | 70 | 1.5 | 90 | 3 | 0 | 22.5 | 1 | 52.5 | 1.75 | 12.5 | 0.5 |
| 118 | 1 | T2N1M0 | 3 | 2B | 40 | 60 | 3 | 20 | 3 | 0 | 22.5 | 2 | 12.5 | 0.25 | 35 | 2 |
| 119 | 1 | T2N1M0 | 3 | 2B | 40 | 0 | 0 | 20 | 1 | 0 | 12.5 | 0.5 | 37.5 | 1 | 32.5 | 1.25 |
| 120 | 1 | T2N1M0 | 2 | 2B | 44 | 100 | 3 | 100 | 3 | 0 | 30 | 2 | 57.5 | 1.5 | 32.5 | 1.5 |
| 121 | 1 | T2N1M0 | 3 | 2B | 51 | 50 | 3 | 90 | 3 | 1 | 12.5 | 0.5 | 37.5 | 1 | 52.5 | 2 |
| 122 | 1 | T2N1M0 | 3 | 2B | 61 | 100 | 3 | 25 | 3 | 0 | 30 | 2 | 22.5 | 1.25 | 17.5 | 1 |
| 123 | 1 | T2N1M0 | 3 | 2B | 41 | 100 | 3 | 100 | 3 | 1 | 22.5 | 2 | 30 | 1 | 42.5 | 1.5 |
| 124 | 1 | T2N1M0 | 2 | 2B | 50 | 20 | 2 | 0 | 0 | 1 | 25 | 1.25 | 52.5 | 1.25 | 22.5 | 1 |
| 125 | 1 | T2N1M0 | 2 | 2B | 64 | 80 | 3 | 80 | 3 | 0 | 22.5 | 1.5 | 47.5 | 1.5 | 12.5 | 0.5 |
| 126 | 1 | T2N1M0 | 2 | 2B | 55 | 80 | 3 | 80 | 3 | 0 | 12.5 | 0.5 | 32.5 | 1 | 37.5 | 1.5 |
| 127 | 1 | T2N1M0 | 2 | 2B | 62 | 30 | 1 | 0 | 0 | 0 | 20 | 1.25 | 12.5 | 0.25 | 12.5 | 1.5 |
| 128 | 1 | T2N1M0 | 3 | 2B | 35 | 70 | 3 | 90 | 3 | 0 | 55 | 1.75 | 20 | 1.25 | 60 | 2 |
| 129 | 1 | T2N1M0 | 3 | 2B | 46 | 85 | 3 | 90 | 3 | 0 | 52.5 | 2 | 52.5 | 1 | 32.5 | 1.5 |
| 130 | 1 | T2N1M0 | 2 | 2B | 62 | 50 | 3 | 50 | 3 | 0 | 57.5 | 2 | 32.5 | 1.25 | 17.5 | 1 |
| 131 | 1 | T2N1M0 | 2 | 2B | 67 | 10 | 1.5 | 15 | 2 | 0 | 22.5 | 1.25 | 12.5 | 0.25 | 12.5 | 0.5 |
| 132 | 1 | T2N1M0 | 2 | 2B | 47 | 80 | 3 | 60 | 2 | 0 | 12.5 | 0.5 | 47.5 | 1.25 | 27.5 | 1 |
| 133 | 1 | T2N1M0 | 2 | 2B | 61 | 50 | 2.5 | 0 | 0 | 0 | 32.5 | 1 | 52.5 | 1.5 | 12.5 | 0.5 |
| 134 | 1 | T2N1M0 | 3 | 2B | 61 | 50 | 3 | 70 | 2 | 1 | 57.5 | 2 | 52.5 | 1.5 | 12.5 | 0.5 |
| 135 | 1 | T2N1M0 | 2 | 2B | 54 | 65 | 3 | 20 | 2 | 0 | 25 | 1.75 | 50 | 1.5 | 12.5 | 0.5 |
| 136 | 1 | T2N1M0 | 1 | 2B | 52 | 60 | 2.5 | 60 | 2 | 0 | 45 | 1.5 | 47.5 | 1.25 | 12.5 | 0.5 |
| 137 | 1 | T2N1M0 | 3 | 2B | 53 | 30 | 2 | 20 | 2 | 0 | 12.5 | 0.5 | 42.5 | 1 | 20 | 0.5 |
| 138 | 1 | T2N1M0 | 3 | 2B | 37 | 75 | 2.5 | 35 | 2.5 | 0 | 50 | 1.75 | 50 | 1.5 | 12.5 | 0.5 |
| 139 | 1 | T2N1M0 | 2 | 2B | 30 | 50 | 2 | 60 | 2 | 0 | 12.5 | 0.5 | 52.5 | 1.25 | 12.5 | 0.5 |
| 140 | 1 | T2N1M0 | 3 | 2B | 48 | 35 | 1.5 | 10 | 2 | 0 | 52.5 | 1.75 | 52.5 | 1.5 | 12.5 | 0.5 |
| 141 | 1 | T2N1M0 | 2 | 2B | 42 | 90 | 3 | 90 | 3 | 0 | 15 | 1.5 | 47.5 | 1.25 | 42.5 | 1.25 |
| 142 | 1 | T2N1M0 | 2 | 2B | 53 | 65 | 2.5 | 0 | 0 | 0 | 12.5 | 0.5 | 42.5 | 1 | 12.5 | 0.5 |
| 143 | 1 | T2N1M0 | 2 | 2B | 36 | 40 | 2 | 15 | 2 | 0 | 27.5 | 1.75 | 52.5 | 1.5 | 12.5 | 0.5 |
| 144 | 1 | T2N1M0 | 2 | 2B | 48 | 80 | 2 | 90 | 2.5 | 0 | 12.5 | 0.5 | 42.5 | 1 | 12.5 | 0.5 |
| 145 | 1 | T2N1M0 | 2 | 2B | 45 | 20 | 2 | 20 | 2.5 | 0 | 30 | 1.5 | 45 | 1.25 | 12.5 | 0.5 |
| 146 | 1 | T2N1M0 | 1 | 2B | 66 | 65 | 2 | 10 | 2 | 0 | 15 | 1 | 45 | 1 | 12.5 | 0.5 |
| 147 | 1 | T2N1M0 | 2 | 2B | 61 | 90 | 3 | 70 | 2 | 0 | 17.5 | 1.25 | 42.5 | 1.25 | 20 | 1 |
| 148 | 1 | T2N1M0 | 1 | 2B | 53 | 75 | 3 | 70 | 3 | 1 | 47.5 | 1.5 | 32.5 | 1 | 42.5 | 1.5 |
| 149 | 1 | T2N1M0 | 2 | 2B | 57 | 80 | 2.5 | 30 | 1.5 | 0 | 20 | 1 | 47.5 | 1 | 52.5 | 1.5 |
| 150 | 1 | T2N1M0 | 3 | 2B | 37 | 60 | 3 | 80 | 3 | 1 | 55 | 2 | 37.5 | 0.75 | 35 | 1 |
| 151 | 0 | T1N0M0 | 3 | 1 | 61 | 10 | 3 | 100 | 3 | 0 | 57.5 | 2 | 52.5 | 1 | 57.5 | 2 |
| 152 | 0 | T2N0M0 | 3 | 2A | 54 | 100 | 3 | 100 | 3 | 0 | 60 | 2 | 42.5 | 1 | 12.5 | 0.5 |
| 153 | 0 | T2N0M0 | 3 | 2A | 51 | 0 | 0 | 20 | 1.5 | 1 | 55 | 2 | 47.5 | 1.25 | 37.5 | 1.5 |
| 154 | 0 | T2N0M0 | 2 | 2A | 41 | 40 | 2 | 100 | 3 | 0 | 22.5 | 1.25 | 60 | 1 | 35 | 1.25 |
| 155 | 0 | T2N0M0 | 3 | 2A | 27 | 0 | 0 | 25 | 1.5 | 1 | 57.5 | 2 | 12.5 | 0.5 | 55 | 1.5 |
| 156 | 0 | T2N0M0 | 3 | 2A | 33 | 0 | 0 | 30 | 3 | 1 | 57.5 | 2 | 57.5 | 1.75 | 60 | 2 |
| 157 | 0 | T2N0M0 | 2 | 2A | 82 | 35 | 2 | 0 | 0 | 1 | 52.5 | 2 | 57.5 | 1.75 | 37.5 | 1.5 |
| 158 | 0 | T2N0M0 | 2 | 2A | 47 | 80 | 2.5 | 60 | 2.5 | 0 | 20 | 1.5 | 52.5 | 1.5 | 12.5 | 0.5 |
| 159 | 0 | T2N0M0 | 3 | 2A | 51 | 100 | 3 | 10 | 1 | 1 | 52.5 | 2 | 12.5 | 0.25 | 42.5 | 1.25 |
| 160 | 0 | T2N0M0 | 3 | 2A | 49 | 80 | 2 | 100 | 3 | 0 | 47.5 | 2 | 32.5 | 1 | 25 | 1.25 |

TABLE 3B

| Sl. No | Outcome | Sample No. | F %-M | FI-M | F %-C | FI-C | K %-M | KI-M | K %-C | KI-C | M %-C | MI-C | N %-C | NI-C | O %-M | OI-M | P %-N | PI-N | R %-M | RI-M | R %-C | RI-C |
|---|---|---|---|---|---|---|---|---|---|---|---|---|---|---|---|---|---|---|---|---|---|---|
| 1 | 1 | MMBVSSSSMMKPR/AAJH/0467/06 | 22.85714286 | 1.25 | 22.5 | 1.25 | 22.5 | 1.75 | 57.5 | 2 | 60 | 2 | 45 | 1.75 | 12.5 | 0.5 | 22.5 | 1 | 24 | 1.25 | 25 | 1.5 |
| 2 | 1 | MMBVSSSSMMKPR/ABMH/4734/07 | 25.71428571 | 0.5 | 30 | 0.5 | 30 | 1.5 | 57.5 | 1.75 | 52.5 | 1.5 | 37.5 | 1.25 | 17.5 | 1 | 45 | 2 | 20 | 0.5 | 27.5 | 1.5 |
| 3 | 1 | MMBVSSSSMMKPR/HLRG/1219/03 | 18.57142857 | 1.25 | 12.5 | 1 | 12.5 | 0.5 | 17.5 | 1 | 42.5 | 1.5 | 47.5 | 1.25 | 32.5 | 1.25 | 27.5 | 1.5 | 26 | 0.5 | 37.5 | 1.25 |
| 4 | 1 | MMBVSSSSMMKPR/ACRG/2834/03 | 32.85714286 | 1 | 57.5 | 0.5 | 32.5 | 1.5 | 55 | 2 | 27.5 | 1.25 | 52.5 | 2 | 12.5 | 0.5 | 20 | 1.5 | 20 | 0.5 | 20 | 1.25 |
| 5 | 1 | MMBVSSSSMMKPR/AVRG/1397/04 | 27.14285714 | 1.75 | 12.5 | 0.5 | 25 | 1 | 55 | 2 | 47.5 | 1.75 | 50 | 1.5 | 12.5 | 0.5 | 12.5 | 0.5 | 20 | 0.5 | 22.5 | 1 |
| 6 | 1 | MMBVSSSSMMKPR/AEMH/6521/06 | 27.14285714 | 1 | 12.5 | 1 | 17.5 | 1.25 | 47.5 | 1.5 | 42.5 | 1.5 | 22.5 | 1.25 | 12.5 | 0.5 | 32.5 | 1.5 | 40 | 0.5 | 17.5 | 1 |
| 7 | 1 | MMBVSSSSMMKPR/AFJH/0478/06 | 15.71428571 | 1 | 22.5 | 0.5 | 12.5 | 1 | 52.5 | 1.5 | 52.5 | 1.25 | 47.5 | 1.5 | 37.5 | 1 | 35 | 2 | 30 | 1 | 32.5 | 1 |
| 8 | 1 | MMBVSSSSMMKPR/HTMX/0675/08 | 12.85714286 | 0.5 | 32.5 | 1.25 | 12.5 | 0.5 | 55 | 1.5 | 30 | 1.25 | 57.5 | 1.25 | 12.5 | 1 | 27.5 | 1.5 | 48 | 1.5 | 37.5 | 1.25 |
| 9 | 1 | MMBVSSSSMMKPR/IRRG/5724/08 | 30 | 1.25 | 20 | 1.25 | 35 | 1.5 | 47.5 | 1.25 | 52.5 | 1.5 | 37.5 | 1.25 | 37.5 | 1 | 45 | 1 | 24 | 1 | 32.5 | 1.25 |
| 10 | 1 | MMBVSSSSMMKPR/JMRG/1480/08 | 18.57142857 | 1.25 | 20 | 1.5 | 17.5 | 1 | 37.5 | 1 | 52.5 | 1.5 | 52.5 | 1.75 | 12.5 | 1.5 | 22.5 | 1.5 | 20 | 1.5 | 20 | 1 |
| 11 | 1 | MMBVSSSSMMKPR/HCGA1/222/10 | 12.85714286 | 1.5 | 50 | 2 | 32.5 | 1.5 | 42.5 | 1.5 | 30 | 1.25 | 42.5 | 1.25 | 12.5 | 0.5 | 50 | 2 | 20 | 0.5 | 12.5 | 1.25 |
| 12 | 1 | MMBVSSSSMMKPR/KIDC/0164/06 | 25.71428571 | 1.25 | 42.5 | 1.5 | 25 | 1.5 | 47.5 | 1.5 | 27.5 | 1.25 | 47.5 | 1.5 | 27.5 | 1 | 42.5 | 1.75 | 28 | 1 | 30 | 0.5 |
| 13 | 1 | MMBVSSSSMMKPR/KJDC/0167/06 | 12.85714286 | 1.25 | 45 | 1.5 | 50 | 1.5 | 47.5 | 1.5 | 52.5 | 1.5 | 47.5 | 1.75 | 12.5 | 0.5 | 57.5 | 2 | 28 | 1 | 47.5 | 1 |
| 14 | 1 | MMBVSSSSMMKPR/KNDC/0176/05 | 27.14285714 | 1.5 | 50 | 0.5 | 12.5 | 1.5 | 42.5 | 1.5 | 47.5 | 1.5 | 52.5 | 1.75 | 27.5 | 0.5 | 12.5 | 0.5 | 30 | 0.5 | 12.5 | 0.5 |
| 15 | 1 | MMBVSSSSMMKPR/MH11/3187/09 | 12.85714286 | 0.5 | 12.5 | 1.75 | 12.5 | 1.25 | 42.5 | 1.5 | 37.5 | 1.5 | 52.5 | 1.75 | 60 | 2 | 57.5 | 2 | 20 | 1 | 52.5 | 0.5 |
| 16 | 1 | MMBVSSSSMMKPR/HCGA4/5535/06 | 12.85714286 | 0.5 | 52.5 | 0.5 | 17.5 | 1.25 | 47.5 | 1.25 | 47.5 | 1.5 | 52.5 | 1.5 | 12.5 | 1.25 | 12.5 | 0.5 | 20 | 0.5 | 50 | 1.5 |
| 17 | 1 | MMBVSSSSMMKPR/SP5/6544/08 | 12.85714286 | 0.5 | 50 | 1.5 | 17.5 | 1.25 | 37.5 | 1.5 | 47.5 | 1.5 | 52.5 | 1.5 | 37.5 | 1.25 | 22.5 | 1.5 | 24 | 1.25 | 47.5 | 1.5 |
| 18 | 1 | MMBVSSSSMMKPR/SP6/5298/06 | 34.28571429 | 1.5 | 50 | 1.5 | 40 | 1.25 | 47.5 | 1 | 47.5 | 1 | 47.5 | 1.75 | 12.5 | 0.5 | 12.5 | 0.5 | 46 | 1.5 | 52.5 | 1.5 |
| 19 | 1 | MMBVSSSSMMKPR/SP6/6116/06 | 12.85714286 | 0.5 | 52.5 | 1.75 | 20 | 0.75 | 47.5 | 1.5 | 52.5 | 1.25 | 52.5 | 1.5 | 37.5 | 1.25 | 40 | 1.25 | 20 | 1 | 52.5 | 1.75 |
| 20 | 1 | MMBVSSSSMMKPR/SP8/6543/06 | 34.28571429 | 1.5 | 52.5 | 1.75 | 50 | 1.25 | 52.5 | 1.25 | 52.5 | 1.5 | 52.5 | 1.5 | 12.5 | 0.5 | 12.5 | 1.25 | 36 | 1.25 | 52.5 | 1.75 |
| 21 | 1 | MMBVSSSSMMKPR/SP9/1761/97 | 15.71428571 | 0.5 | 52.5 | 1.75 | 20 | 1.25 | 47.5 | 1.5 | 50 | 1.5 | 52.5 | 1.75 | 50 | 1.25 | 12.5 | 0.5 | 52 | 0.5 | 52.5 | 1.5 |
| 22 | 1 | MMBVSSSSMMKPR/SP9/2006/02 | 20 | 1 | 52.5 | 1.75 | 27.5 | 1.25 | 52.5 | 1.5 | 50 | 1.5 | 50 | 1.5 | 22.5 | 1.25 | 12.5 | 0.5 | 20 | 1.25 | 52.5 | 1.75 |
| 23 | 1 | MMBVSSSSMMKPR/SP10/4338/05 | 15.71428571 | 1.25 | 52.5 | 0.5 | 27.5 | 1.25 | 52.5 | 1.5 | 47.5 | 1.25 | 47.5 | 1.5 | 20 | 1.25 | 12.5 | 0.5 | 28 | 0.5 | 47.5 | 1.75 |
| 24 | 1 | MMBVSSSSMMKPR/SP13/0242/10 | 12.85714286 | 0.5 | 12.5 | 0.5 | 42.5 | 1.5 | 50 | 1.5 | 47.5 | 1.25 | 52.5 | 1.75 | 30 | 1.75 | 42.5 | 1.25 | 24 | 1 | 17.5 | 1.75 |
| 25 | 1 | MMBVSSSSMMKPR/ADRG/1440/02 | 24.28571429 | 1 | 52.5 | 0.5 | 32.5 | 1.75 | 37.5 | 2 | 52.5 | 2 | 27.5 | 1.25 | 22.5 | 1 | 32.5 | 2 | 30 | 1 | 27.5 | 1 |
| 26 | 1 | MMBVSSSSMMKPR/AGMH/2268/04 | 21.42857143 | 1.25 | 12.5 | 0.5 | 12.5 | 0.5 | 47.5 | 1.5 | 50 | 1.5 | 20 | 1.25 | 12.5 | 0.5 | 50 | 2 | 26 | 1.25 | 47.5 | 1.25 |
| 27 | 1 | MMBVSSSSMMKPR/AHMH/2180/05 | 18.57142857 | 1.5 | 22.5 | 0.5 | 12.5 | 1.25 | 57.5 | 2 | 60 | 2 | 55 | 1.25 | 27.5 | 0.5 | 27.5 | 1.5 | 26 | 0.5 | 47.5 | 1.5 |
| 28 | 1 | MMBVSSSSMMKPR/AJMH/1975/03 | 38.57142857 | 1.75 | 32.5 | 0.5 | 32.5 | 0.5 | 52.5 | 1.5 | 47.5 | 1.5 | 12.5 | 0.5 | 47.5 | 1.25 | 57.5 | 2 | 32 | 1.25 | 52.5 | 1.5 |
| 29 | 1 | MMBVSSSSMMKPR/AKMH/1186/03 | 22.85714286 | 0.5 | 12.5 | 1 | 12.5 | 0.5 | 55 | 2 | 57.5 | 1.25 | 60 | 1.5 | 12.5 | 0.5 | 45 | 1.75 | 44 | 1.25 | 12.5 | 1.5 |
| 30 | 1 | MMBVSSSSMMKPR/ALMH/4227/05 | 22.85714286 | 1.25 | 42.5 | 0.5 | 27.5 | 1.25 | 55 | 1.5 | 47.5 | 1.75 | 52.5 | 1.5 | 25 | 1 | 17.5 | 1.25 | 36 | 1 | 47.5 | 0.5 |
| 31 | 1 | MMBVSSSSMMKPR/AMMH/2138/05 | 12.85714286 | 0.5 | 12.5 | 0.5 | 52.5 | 1.25 | 37.5 | 1.5 | 50 | 1.25 | 42.5 | 1.5 | 32.5 | 1.25 | 47.5 | 1.5 | 36 | 1 | 42.5 | 1.5 |
| 32 | 1 | MMBVSSSSMMKPR/ANMH/6528/05 | 12.85714286 | 0.5 | 12.5 | 0.5 | 52.5 | 1.25 | 55 | 1.5 | 47.5 | 1.5 | 37.5 | 1.25 | 12.5 | 1 | 50 | 1.75 | 24 | 1.5 | 22.5 | 0.5 |
| 33 | 1 | MMBVSSSSMMKPR/AOMH/1621/05 | 24.28571429 | 1 | 52.5 | 1 | 12.5 | 0.5 | 57.5 | 1.5 | 47.5 | 1.25 | 25 | 1 | 12.5 | 0.5 | 12.5 | 0.5 | 24 | 1 | 27.5 | 1 |
| 34 | 1 | MMBVSSSSMMKPR/APMH/6408/05 | 22.85714286 | 0.5 | 20 | 0.5 | 35 | 1 | 47.5 | 2 | 50 | 2 | 30 | 1.5 | 45 | 0.75 | 20 | 1.25 | 26 | 0.5 | 17.5 | 1 |
| 35 | 1 | MMBVSSSSMMKPR/AQMH/1408/06 | 22.85714286 | 1.25 | 12.5 | 1 | 12.5 | 1.25 | 52.5 | 1.5 | 47.5 | 1.25 | 47.5 | 1.25 | 25 | 1.25 | 12.5 | 1.5 | 36 | 1 | 12.5 | 1.25 |
| 36 | 1 | MMBVSSSSMMKPR/ARMH/4622/06 | 12.85714286 | 0.5 | 12.5 | 0.5 | 32.5 | 1.25 | 45 | 1.5 | 47.5 | 1.25 | 37.5 | 1.75 | 45 | 1.5 | 37.5 | 0.5 | 32 | 0.5 | 42.5 | 1.5 |
| 37 | 1 | MMBVSSSSMMKPR/ASRG/5174/03 | 20 | 1 | 32.5 | 1 | 12.5 | 1 | 55 | 2 | 50 | 2 | 47.5 | 1 | 52.5 | 1.5 | 50 | 1.75 | 40 | 1.5 | 25 | 0.5 |
| 38 | 1 | MMBVSSSSMMKPR/ATMH/4074/01 | 12.85714286 | 0.5 | 17.5 | 1.25 | 12.5 | 0.5 | 37.5 | 1.5 | 32.5 | 1.25 | 47.5 | 1.25 | 17.5 | 0.5 | 12.5 | 1.25 | 20 | 1 | 27.5 | 1 |
| 39 | 1 | MMBVSSSSMMKPR/AYRG/3670/02 | 12.85714286 | 0.5 | 30 | 1 | 12.5 | 0.5 | 60 | 1.75 | 50 | 1.75 | 30 | 1 | 27.5 | 1.25 | 20 | 0.5 | 36 | 0.5 | 22.5 | 1.5 |
| 40 | 1 | MMBVSSSSMMKPR/AZRG/1472/02 | 32.85714286 | 1 | 47.5 | 1 | 22.5 | 1.5 | 50 | 2 | 47.5 | 1.5 | 47.5 | 1.5 | 12.5 | 0.5 | 12.5 | 1.25 | 20 | 0.5 | 45 | 1.5 |
| 41 | 1 | MMBVSSSSMMKPR/BAJH/0102/07 | 28.57142857 | 1 | 37.5 | 0.5 | 12.5 | 0.5 | 27.5 | 1 | 47.5 | 1.25 | 37.5 | 1.25 | 52.5 | 1.75 | 42.5 | 2 | 36 | 1 | 42.5 | 1.5 |
| 42 | 1 | MMBVSSSSMMKPR/HSMH/4789/07 | 12.85714286 | 0.5 | 12.5 | 1 | 12.5 | 1 | 50 | 2 | 32.5 | 1.25 | 47.5 | 1.5 | 22.5 | 0.5 | 47.5 | 1.5 | 38 | 0.5 | 17.5 | 1 |
| 43 | 1 | MMBVSSSSMMKPR/HKRG/3754/03 | 12.85714286 | 0.5 | 12.5 | 1.75 | 52.5 | 1.5 | 45 | 1.5 | 57.5 | 1.25 | 45 | 1.5 | 22.5 | 0.5 | 12.5 | 1.5 | 24 | 1 | 12.5 | 1.25 |
| 44 | 1 | MMBVSSSSMMKPR/IMRG/5141/08 | 12.85714286 | 1 | 42.5 | 1.5 | 20 | 1.5 | 60 | 2 | 37.5 | 1.25 | 57.5 | 2 | 17.5 | 1 | 27.5 | 1.25 | 32 | 1 | 52.5 | 1 |
| 45 | 1 | MMBVSSSSMMKPR/IQRG/5751/08 | 37.14285714 | 2 | 42.5 | 1.5 | 12.5 | 1.5 | 27.5 | 1.25 | 47.5 | 1.25 | 42.5 | 2 | 27.5 | 1 | 50 | 1.25 | 20 | 1.5 | 57.5 | 2 |
| 46 | 1 | MMBVSSSSMMKPR/JNRG/6963/08 | 18.57142857 | 1.25 | 42.5 | 1.25 | 25 | 1.25 | 52.5 | 2 | 45 | 1.25 | 57.5 | 2 | 30 | 0.75 | 42.5 | 1.25 | 32 | 1.25 | 32.5 | 2 |
| 47 | 1 | MMBVSSSSMMKPR/JORG/620/08 | 17.14285714 | 1.5 | 47.5 | 1.5 | 27.5 | 1.25 | 52.5 | 1.25 | 40 | 1.75 | 55 | 1.25 | 12.5 | 0.5 | 42.5 | 1.25 | 32 | 1.25 | 52.5 | 1.5 |

TABLE 3B-continued

| Sl. No | Outcome | Sample No. | F %-M | FI-M | F %-C | FI-C | K %-M | KI-M | K %-C | KI-C | M %-C | MI-C | N %-C | NI-C | O %-M | OI-M | P %-N | PI-N | R %-M | RI-M | R %-C | RI-C |
|---|---|---|---|---|---|---|---|---|---|---|---|---|---|---|---|---|---|---|---|---|---|---|
| 48 | 1 | MMBYSSSSMMKPR/IXRG/1912/08 | 17.14285714 | 1 | 47.5 | 2 | 37.5 | 1.25 | 25 | 1.5 | 47.5 | 1.5 | 47.5 | 1.75 | 12.5 | 0.5 | 27.5 | 1 | 30 | 1.5 | 37.5 | 1.75 |
| 49 | 1 | MMBYSSSSMMKPR/IHRG/1461/07 | 18.57142857 | 1 | 52.5 | 1.25 | 32.5 | 1.25 | 47.5 | 2 | 60 | 1.5 | 45 | 1.5 | 12.5 | 0.5 | 42.5 | 1 | 40 | 1.5 | 47.5 | 1.75 |
| 50 | 1 | MMBYSSSSMMKPR/INRG/6074/08 | 15.71428571 | 1 | 27.5 | 1.75 | 12.5 | 0.5 | 55 | 2 | 52.5 | 1.5 | 47.5 | 1.5 | 12.5 | 0.5 | 25 | 1.25 | 26 | 1.5 | 27.5 | 1.5 |
| 51 | 1 | MMBYSSSSMMKPR/JPRG/7119/08 | 18.57142857 |  | 47.5 | 1.5 | 35 | 1.5 | 52.5 | 2 | 45 | 1.5 | 50 | 1.75 | 45 | 1.25 | 37.5 | 0.5 | 28 | 1.25 | 37.5 | 1.5 |
| 52 | 1 | MMBYSSSSMMKPR/IARG/1209/01 | 12.85714286 | 0.5 | 32.5 | 1.5 | 37.5 | 1.25 | 42.5 | 2 | 47.5 | 2 | 20 | 1 | 12.5 | 0.5 | 12.5 | 1.5 | 20 | 0.5 | 37.5 | 1.5 |
| 53 | 1 | MMBYSSSSMMKPR/JQRG/6998/08 | 18.57142857 | 1 | 47.5 | 1.75 | 22.5 | 1 | 52.5 | 1.75 | 52.5 | 1.5 | 57.5 | 1 | 27.5 | 0.75 | 55 | 1.5 | 32 | 1 | 30 | 1.25 |
| 54 | 1 | MMBYSSSSMMKPR/HCGA1/5042/08 | 18.57142857 | 1.25 | 47.5 | 1.75 | 22.5 | 1.25 | 52.5 | 1.75 | 52.5 | 1.5 | 52.5 | 1.75 | 20 | 1 | 17.5 | 0.5 | 30 | 1.5 | 42.5 | 1 |
| 55 | 1 | MMBYSSSSMMKPR/RG20/7272/08 | 18.57142857 |  | 47.5 | 0.5 | 12.5 | 0.5 | 52.5 | 1.75 | 42.5 | 1.25 | 52.5 | 1.5 | 37.5 | 1 | 57.5 | 1.25 | 20 | 1 | 17.5 | 1.5 |
| 56 | 1 | MMBYSSSSMMKPR/MH10/826/06 | 12.85714286 | 0.5 | 12.5 | 1.25 | 42.5 | 0.5 | 50 | 1.75 | 52.5 | 1.75 | 42.5 | 1.5 | 50 | 2 | 47.5 | 1.5 | 28 | 0.5 | 42.5 | 1 |
| 57 | 1 | MMBYSSSSMMKPR/MH12/6907/09 | 15.71428571 | 1.25 | 47.5 | 1.75 | 12.5 | 1 | 52.5 | 1.5 | 42.5 | 1.5 | 52.5 | 1.75 | 40 | 1 | 45 | 2 | 28 | 1.25 | 42.5 | 1.5 |
| 58 | 1 | MMBYSSSSMMKPR/MH13/5276/09 | 21.42857143 | 1.25 | 22.5 | 1.5 | 50 | 1.75 | 52.5 | 1.5 | 50 | 1.75 | 37.5 | 1.75 | 22.5 | 1.5 | 45 | 2 | 20 | 0.5 | 52.5 | 1.25 |
| 59 | 1 | MMBYSSSSMMKPR/MH13/2852/02 | 20 | 1.5 | 52.5 | 1.75 | 25 | 1.25 | 55 | 1.5 | 45 | 1.5 | 45 | 1.5 | 12.5 | 0.5 | 52.5 | 2 | 24 | 1 | 52.5 | 1.5 |
| 60 | 1 | MMBYSSSSMMKPR/RG24/2672/09 | 17.14285714 |  | 55 | 1.5 | 22.5 | 1.25 | 55 | 1.75 | 47.5 | 1.5 | 50 | 1.75 | 22.5 | 0.5 | 12.5 | 0.5 | 28 | 1.5 | 47.5 | 1.75 |
| 61 | 1 | MMBYSSSSMMKPR/RG24/786/09 | 27.14285714 | 1.25 | 50 | 1.5 | 27.5 | 1.5 | 55 | 1.75 | 50 | 1.75 | 52.5 | 1.75 | 32.5 | 1.25 | 12.5 | 0.5 | 40 | 1.25 | 52.5 | 1.5 |
| 62 | 1 | MMBYSSSSMMKPR/RG24/3773/09 | 17.14285714 | 1.25 | 50 | 1.5 | 40 | 1.75 | 47.5 | 1.5 | 32.5 | 1.5 | 37.5 | 1.75 | 12.5 | 1 | 15 | 1.5 | 24 | 1 | 45 | 1.75 |
| 63 | 1 | MMBYSSSSMMKPR/RG24/3821/09 | 18.57142857 | 1 | 52.5 | 1.75 | 25 | 1.75 | 55 | 1.5 | 50 | 1.75 | 45 | 1.5 | 32.5 | 1.25 | 12.5 | 0.5 | 24 | 0.5 | 47.5 | 1.25 |
| 64 | 1 | MMBYSSSSMMKPR/RG25/1072/09 | 17.14285714 | 1.5 | 52.5 | 1.75 | 17.5 | 1.5 | 52.5 | 1.5 | 22.5 | 1.25 | 50 | 1.75 | 47.5 | 1.75 | 12.5 | 0.5 | 20 | 1.25 | 47.5 | 1.75 |
| 65 | 1 | MMBYSSSSMMKPR/HCGA5/7545/07 | 30 |  | 52.5 | 1.75 | 52.5 | 1.25 | 52.5 | 1.75 | 42.5 | 1.25 | 50 | 1.75 | 17.5 | 1 | 20 | 1.25 | 48 | 0.5 | 12.5 | 0.5 |
| 66 | 1 | MMBYSSSSMMKPR/SP2/2851/03 | 17.14285714 | 1 | 47.5 | 1.75 | 22.5 | 1 | 47.5 | 2 | 52.5 | 1.25 | 52.5 | 1.5 | 47.5 | 1 | 12.5 | 0.5 | 24 | 1.25 | 27.5 | 1.25 |
| 67 | 1 | MMBYSSSSMMKPR/SP2/06011/08 | 15.71428571 | 1.5 | 55 | 1.75 | 47.5 | 1.25 | 52.5 | 1.75 | 52.5 | 1.25 | 52.5 | 1.5 | 25 | 1.5 | 12.5 | 0.5 | 26 | 1.5 | 50 | 1.75 |
| 68 | 1 | MMBYSSSSMMKPR/SP2/5595E/04 | 32.85714286 | 1.5 | 50 | 1.75 | 50 | 1.5 | 50 | 1.5 | 47.5 | 1.5 | 42.5 | 1.5 | 32.5 | 1.5 | 12.5 | 0.5 | 40 | 1.5 | 50 | 1.5 |
| 69 | 1 | MMBYSSSSMMKPR/SP3/12267/07 | 31.42857143 | 1.75 | 50 | 1.5 | 50 | 1.75 | 50 | 1.5 | 50 | 1.25 | 50 | 1.75 | 47.5 | 1.75 | 15 | 1.5 | 44 | 1.5 | 45 | 1.5 |
| 70 | 1 | MMBYSSSSMMKPR/SP3/09935/08 | 34.28571429 | 1.5 | 50 | 1.5 | 25 | 1 | 55 | 1.75 | 32.5 | 1 | 50 | 1.75 | 47.5 | 1.5 | 12.5 | 0.5 | 24 | 1.5 | 47.5 | 1.25 |
| 71 | 1 | MMBYSSSSMMKPR/SP4/04418/08 | 18.57142857 | 1.5 | 52.5 | 1.25 | 32.5 | 1.25 | 52.5 | 1.75 | 22.5 | 1.5 | 37.5 | 1.75 | 17.5 | 1 | 12.5 | 1.25 | 20 | 1 | 52.5 | 1.75 |
| 72 | 1 | MMBYSSSSMMKPR/KFDC/0149/07 | 24.28571429 | 1.25 | 50 | 1.25 | 27.5 | 1.25 | 47.5 | 1.75 | 42.5 | 1.5 | 47.5 | 1.25 | 47.5 | 1.25 | 20 | 0.5 | 48 | 1 | 12.5 | 0.5 |
| 73 | 1 | MMBYSSSSMMKPR/BDRG/5248/04 | 12.85714286 | 0.5 | 37.5 | 1.5 | 25 | 1.25 | 52.5 | 2 | 32.5 | 1.5 | 47.5 | 1.25 | 25 | 1.25 | 50 | 0.5 | 24 | 1.5 | 27.5 | 1.25 |
| 74 | 1 | MMBYSSSSMMKPR/KODC/0178/05 | 12.85714286 | 1 | 37.5 | 1.25 | 27.5 | 1.75 | 47.5 | 2 | 17.5 | 1 | 12.5 | 0.5 | 12.5 | 0.5 | 12.5 | 0.5 | 26 | 0.5 | 52.5 | 0.5 |
| 75 | 1 | MMBYSSSSMMKPR/SP5/2503/08 | 30 | 1.5 | 55 | 1.75 | 47.5 | 1.75 | 50 | 1.75 | 37.5 | 1.5 | 42.5 | 1.5 | 27.5 | 1 | 17.5 | 1.25 | 38 | 1.5 | 47.5 | 1.75 |
| 76 | 1 | MMBYSSSSMMKPR/SP5/2049/09 | 34.28571429 | 1.75 | 50 | 1.25 | 52.5 | 1.75 | 52.5 | 1.5 | 45 | 1.75 | 50 | 1.75 | 30 | 1.25 | 12.5 | 0.5 | 40 | 1.5 | 45 | 1.75 |
| 77 | 1 | MMBYSSSSMMKPR/SP5/2933/09 | 35.71428571 | 1.75 | 52.5 | 1.75 | 55 | 1.75 | 30 | 1.5 | 45 | 1.75 | 47.5 | 1.25 | 50 | 1.5 | 12.5 | 0.5 | 48 | 1.5 | 50 | 1.5 |
| 78 | 1 | MMBYSSSSMMKPR/SP5/5414/09 | 28.57142857 | 1.5 | 52.5 | 1 | 12.5 | 0.5 | 40 | 1.5 | 50 | 1.5 | 45 | 1.75 | 17.5 | 1.25 | 22.5 | 1.25 | 30 | 1 | 50 | 1.5 |
| 79 | 1 | MMBYSSSSMMKPR/SP5/6317/09 | 12.85714286 | 0.5 | 42.5 | 1.75 | 55 | 0.5 | 30 | 0.75 | 52.5 | 0.5 | 52.5 | 1.75 | 40 | 1.25 | 25 | 1.75 | 28 | 1.25 | 52.5 | 1.5 |
| 80 | 1 | MMBYSSSSMMKPR/SP5/5630/07 | 35.71428571 | 1.5 | 52.5 | 1.75 | 32.5 | 1.25 | 55 | 1 | 52.5 | 1.75 | 50 | 1.75 | 47.5 | 1.25 | 27.5 | 1.5 | 50 | 1.5 | 52.5 | 1.5 |
| 81 | 1 | MMBYSSSSMMKPR/SP6/4628/02 | 12.85714286 | 1.5 | 52.5 | 1.5 | 52.5 | 1.75 | 42.5 | 1.25 | 50 | 1.75 | 52.5 | 1.75 | 42.5 | 1.25 | 12.5 | 0.5 | 42 | 1.5 | 52.5 | 1.5 |
| 82 | 1 | MMBYSSSSMMKPR/SP6/215/05 | 27.14285714 | 0.5 | 47.5 | 0.5 | 17.5 | 1 | 52.5 | 1.5 | 52.5 | 1.25 | 52.5 | 1.75 | 42.5 | 1.25 | 12.5 | 0.5 | 20 | 1.5 | 52.5 | 1.5 |
| 83 | 1 | MMBYSSSSMMKPR/SP6/4283/08 | 27.14285714 | 1 | 52.5 | 1 | 52.5 | 1.25 | 52.5 | 1.5 | 52.5 | 1.5 | 52.5 | 1.75 | 42.5 | 1.25 | 40 | 1.25 | 44 | 1.5 | 52.5 | 1.5 |
| 84 | 1 | MMBYSSSSMMKPR/SP6/3004/09 | 32.85714286 | 1.5 | 52.5 | 1.25 | 47.5 | 1.25 | 50 | 1.5 | 52.5 | 1.75 | 50 | 1.75 | 42.5 | 1.25 | 12.5 | 0.5 | 48 | 1.5 | 52.5 | 1.5 |
| 85 | 1 | MMBYSSSSMMKPR/SP7/6675/07 | 32.85714286 | 1.25 | 52.5 | 1.25 | 27.5 | 1.25 | 52.5 | 1.5 | 45 | 1.5 | 52.5 | 1.75 | 47.5 | 1.25 | 17.5 | 1.5 | 28 | 1 | 52.5 | 1.5 |
| 86 | 1 | MMBYSSSSMMKPR/SP7/4924/06 | 15.71428571 | 1.25 | 52.5 | 1.5 | 25 | 1.75 | 47.5 | 2 | 37.5 | 1.5 | 37.5 | 1.5 | 17.5 | 1.25 | 40 | 1.5 | 28 | 1 | 47.5 | 1.5 |
| 87 | 1 | MMBYSSSSMMKPR/SP8/7537/09 | 17.14285714 | 1.25 | 50 | 1.5 | 27.5 | 1.25 | 50 | 1 | 52.5 | 1.5 | 37.5 | 1.75 | 17.5 | 1.25 | 27.5 | 1 | 42 | 1 | 47.5 | 1.75 |
| 88 | 1 | MMBYSSSSMMKPR/SP8/3347/09 | 28.57142857 | 1.5 | 55 | 1.25 | 42.5 | 1.25 | 52.5 | 1.75 | 52.5 | 1.5 | 50 | 1.75 | 40 | 1.25 | 17.5 | 1.5 | 28 | 1 | 52.5 | 1.75 |
| 89 | 1 | MMBYSSSSMMKPR/SP8/7252/08 | 20 | 1.5 | 50 | 1.75 | 47.5 | 1.75 | 30 | 1.5 | 12.5 | 0.5 | 42.5 | 1.75 | 42.5 | 1.25 | 22.5 | 1.5 | 42 | 1.25 | 17.5 | 1.25 |
| 90 | 1 | MMBYSSSSMMKPR/AURG/1691/04 | 27.14285714 | 2 | 12.5 | 0.5 | 25 | 1.25 | 20 | 0.75 | 32.5 | 1 | 27.5 | 1.5 | 32.5 | 0.5 | 32.5 | 1.5 | 28 | 1.25 | 12.5 | 0.5 |
| 91 | 1 | MMBYSSSSMMKPR/AWRG/3418/04 | 12.85714286 | 0.5 | 12.5 | 1.5 | 42.5 | 1 | 55 | 1 | 47.5 | 1.5 | 37.5 | 1.75 | 12.5 | 0.5 | 17.5 | 1.5 | 34 | 1 | 27.5 | 1.25 |
| 92 | 1 | MMBYSSSSMMKPR/HCGA1/6737/09 | 12.85714286 | 0.5 | 47.5 | 0.5 | 17.5 | 1.25 | 20 | 1 | 45 | 2 | 52.5 | 1.75 | 12.5 | 1.5 | 22.5 | 0.5 | 20 | 0.5 | 17.5 | 1.25 |
| 93 | 1 | MMBYSSSSMMKPR/HCGA3/5860/09 | 12.85714286 | 1 | 47.5 | 1 | 27.5 | 1.75 | 47.5 | 1.5 | 45 | 1.5 | 37.5 | 1.5 | 30 | 1.5 | 42.5 | 1.5 | 24 | 1.25 | 52.5 | 1.5 |
| 94 | 1 | MMBYSSSSMMKPR/BBMH/6814/07 | 24.28571429 | 1.5 | 37.5 | 0.5 | 25 | 1 | 35 | 2 | 17.5 | 2 | 52.5 | 1.5 | 12.5 | 1 | 37.5 | 1 | 26 | 0.5 | 22.5 | 0.5 |
| 95 | 1 | MMBYSSSSMMKPR/BEMH/3166/01 | 27.14285714 | 1 | 12.5 | 0.5 | 27.5 | 1.5 | 15 | 1 | 52.5 | 1 | 37.5 | 0.5 | 30 | 1.5 | 12.5 | 1 | 20 | 0.5 | 47.5 | 1.25 |
| 96 | 1 | MMBYSSSSMMKPR/RG25/2941/09 | 27.14285714 | 1 | 47.5 | 1.75 | 42.5 | 1.5 | 42.5 | 1.75 | 47.5 | 1.5 | 47.5 | 1.25 | 42.5 | 1.5 | 12.5 | 0.5 | 40 | 1 | 52.5 | 1.5 |

TABLE 3B-continued

| Sl. No | Outcome | Sample No. | F %-M | FI-M | F %-C | FI-C | K %-M | KI-M | K %-C | KI-C | M %-M | MI-M | N %-C | NI-C | O %-M | OI-M | P %-N | PI-N | R %-M | RI-M | R %-C | RI-C |
|---|---|---|---|---|---|---|---|---|---|---|---|---|---|---|---|---|---|---|---|---|---|---|
| 97 | 1 | MMBYSSSMMKPR/SP1/1287/98 | 27.14285714 | 1.25 | 52.5 | 1.75 | 37.5 | 1.25 | 50 | 1.5 | 42.5 | 1.5 | 47.5 | 1.25 | 12.5 | 0.5 | 12.5 | 0.5 | 40 | 1.25 | 55 | 1.5 |
| 98 | 1 | MMBYSSSMMKPR/SP2/00396/06 | 21.42857143 | 1.5 | 55 | 1.75 | 25 | 1.25 | 52.5 | 1.5 | 47.5 | 1.5 | 52.5 | 1.75 | 22.5 | 1 | 20 | 1.5 | 30 | 1.5 | 52.5 | 1.75 |
| 99 | 1 | MMBYSSSMMKPR/SP2/5090/03 | 12.85714286 | 0.5 | 55 | 1.75 | 32.5 | 1.5 | 50 | 1.5 | 52.5 | 1.5 | 52.5 | 1.75 | 22.5 | 1 | 12.5 | 0.5 | 26 | 1.5 | 55 | 1.75 |
| 100 | 1 | MMBYSSSMMKPR/SP3/00076/06 | 17.14285714 | 1.5 | 52.5 | 1.75 | 37.5 | 1.5 | 52.5 | 1.5 | 52.5 | 1.5 | 47.5 | 1.25 | 20 | 1.5 | 12.5 | 0.5 | 32 | 0.5 | 42.5 | 1.75 |
| 101 | 1 | MMBYSSSMMKPR/SP5/5658/09 | 17.14285714 | 1.5 | 55 | 1.75 | 12.5 | 0.5 | 47.5 | 1.5 | 47.5 | 1.5 | 45 | 1.25 | 32.5 | 1.5 | 12.5 | 0.5 | 20 | 1.5 | 52.5 | 1.75 |
| 102 | 1 | MMBYSSSMMKPR/SP9/1431/07 | 18.57142857 | 1.25 | 52.5 | 1.75 | 37.5 | 1.25 | 52.5 | 1.25 | 52.5 | 1.5 | 52.5 | 1.75 | 20 | 1.25 | 32.5 | 1.25 | 24 | 1.5 | 52.5 | 1.75 |
| 103 | 1 | MMBYSSSMMKPR/SP9/00521/07 | 15.71428571 | 1 | 52.5 | 1.75 | 32.5 | 1 | 42.5 | 1.25 | 47.5 | 1.5 | 52.5 | 1.5 | 20 | 1.5 | 15 | 1.5 | 32 | 1.25 | 47.5 | 1.75 |
| 104 | 1 | MMBYSSSMMKPR/SP9/919/99 | 18.57142857 | 1.5 | 52.5 | 1.75 | 25 | 1 | 47.5 | 1.25 | 42.5 | 1.5 | 50 | 1.75 | 12.5 | 0.5 | 40 | 1.5 | 32 | 0.5 | 52.5 | 1.25 |
| 105 | 1 | MMBYSSSMMKPR/SP10/1693/03 | 15.71428571 | 1.5 | 47.5 | 1.5 | 22.5 | 1.25 | 47.5 | 1.25 | 52.5 | 1.5 | 52.5 | 1.5 | 40 | 1.5 | 52.5 | 0.5 | 50 | 1.5 | 50 | 1.5 |
| 106 | 1 | MMBYSSSMMKPR/SP11/2802/01 | 32.85714286 | 1.25 | 47.5 | 1.5 | 45 | 1.5 | 50 | 1.25 | 42.5 | 1.5 | 52.5 | 1.5 | 22.5 | 1.25 | 40 | 1.5 | 48 | 1.25 | 50 | 1.5 |
| 107 | 1 | MMBYSSSMMKPR/SP11/1002/05 | 24.28571429 | 1.25 | 47.5 | 1.25 | 45 | 1.5 | 42.5 | 1.25 | 52.5 | 1.5 | 15 | 1.5 | 42.5 | 1.25 | 52.5 | 1.5 | 32 | 1.25 | 47.5 | 1.5 |
| 108 | 1 | MMBYSSSMMKPR/SP11/4945/09 | 18.57142857 | 1 | 47.5 | 1.25 | 37.5 | 1.25 | 50 | 1.25 | 50 | 1.5 | 52.5 | 1.75 | 37.5 | 1.5 | 55 | 1.5 | 36 | 1.5 | 47.5 | 1.5 |
| 109 | 1 | MMBYSSSMMKPR/RG32/47/10 | 17.14285714 | 1.5 | 47.5 | 1.5 | 50 | 1.5 | 42.5 | 1.25 | 42.5 | 1.5 | 42.5 | 1.5 | 35 | 1.25 | 20 | 1.5 | 40 | 1.5 | 50 | 1.5 |
| 110 | 1 | MMBYSSSMMKPR/RG32/7449/09 | 31.42857143 | 1.5 | 47.5 | 0.75 | 50 | 1.5 | 42.5 | 1.5 | 50 | 1.5 | 52.5 | 1.75 | 42.5 | 1.25 | 22.5 | 0.5 | 40 | 0.5 | 40 | 1.5 |
| 111 | 1 | MMBYSSSMMKPR/SP12/0353/09 | 12.85714286 | 0.5 | 47.5 | 0.75 | 37.5 | 1.5 | 42.5 | 1.25 | 50 | 1.5 | 52.5 | 1.5 | 37.5 | 1.25 | 47.5 | 1.5 | 50 | 1.25 | 50 | 1.5 |
| 112 | 1 | MMBYSSSMMKPR/SP12/2027/09 | 17.14285714 | 1 | 47.5 | 1 | 50 | 1.25 | 42.5 | 1.25 | 50 | 1.5 | 52.5 | 1.5 | 35 | 1.25 | 55 | 1.5 | 32 | 1.25 | 47.5 | 1.5 |
| 113 | 1 | MMBYSSSMMKPR/SP12/1631/09 | 15.71428571 | 1.5 | 47.5 | 1.5 | 37.5 | 1 | 52.5 | 1.25 | 42.5 | 1.5 | 47.5 | 1.5 | 27.5 | 1.25 | 20 | 1.5 | 24 | 1.5 | 52.5 | 1.75 |
| 114 | 1 | MMBYSSSMMKPR/RG34/1091/10 | 24.28571429 | 1.25 | 40 | 1.25 | 40 | 1.5 | 52.5 | 1.5 | 52.5 | 1.25 | 52.5 | 1.75 | 40 | 1.25 | 52.5 | 1.5 | 36 | 1.25 | 50 | 1.5 |
| 115 | 1 | MMBYSSSMMKPR/SP13/6097/08 | 20 | 1.25 | 47.5 | 1.5 | 35 | 1.5 | 47.5 | 1.5 | 50 | 1.5 | 52.5 | 1.75 | 30 | 1.25 | 27.5 | 1.25 | 32 | 1.25 | 52.5 | 1.5 |
| 116 | 1 | MMBYSSSMMKPR/BFMH/2540/04 | 12.85714286 | 0.5 | 12.5 | 1.5 | 32.5 | 1.5 | 52.5 | 1.5 | 57.5 | 1.5 | 25 | 1 | 12.5 | 0.5 | 15 | 1.25 | 26 | 1.25 | 47.5 | 1.5 |
| 117 | 1 | MMBYSSSMMKPR/BGMH/3558/03 | 30 | 1.25 | 32.5 | 0.5 | 30 | 1 | 52.5 | 1.25 | 55 | 1.75 | 47.5 | 1.25 | 12.5 | 0.5 | 20 | 0.5 | 30 | 0.5 | 25 | 0.5 |
| 118 | 1 | MMBYSSSMMKPR/BIMH/4596/05 | 17.14285714 | 1.5 | 27.5 | 0.5 | 50 | 1.5 | 27.5 | 1.25 | 37.5 | 1.5 | 20 | 1 | 30 | 2 | 57.5 | 2 | 24 | 1 | 37.5 | 0.5 |
| 119 | 1 | MMBYSSSMMKPR/BJMH/1942/07 | 30 | 1.5 | 12.5 | 0.5 | 12.5 | 0.5 | 52.5 | 1.5 | 52.5 | 2 | 37.5 | 1.5 | 12.5 | 1.5 | 12.5 | 0.5 | 20 | 0.5 | 37.5 | 1.25 |
| 120 | 1 | MMBYSSSMMKPR/BKMH/3435/06 | 17.14285714 | 1.25 | 32.5 | 1 | 32.5 | 1.5 | 12.5 | 1.5 | 12.5 | 0.5 | 47.5 | 0.5 | 12.5 | 0.5 | 22.5 | 1 | 20 | 0.5 | 20 | 0.5 |
| 121 | 1 | MMBYSSSMMKPR/BLJH/2584/05 | 24.28571429 | 1.25 | 22.5 | 1 | 37.5 | 1.75 | 47.5 | 1.75 | 17.5 | 1.5 | 12.5 | 0.5 | 27.5 | 1.5 | 22.5 | 1.5 | 20 | 0.5 | 25 | 1.25 |
| 122 | 1 | MMBYSSSMMKPR/BMMH/3591/08 | 12.85714286 | 0.5 | 52.5 | 1.25 | 25 | 1.25 | 52.5 | 1.25 | 32.5 | 1.5 | 30 | 1 | 50 | 2 | 47.5 | 1.5 | 20 | 0.5 | 42.5 | 1.5 |
| 123 | 1 | MMBYSSSMMKPR/BNMH/3242/06 | 18.57142857 | 1.25 | 52.5 | 0.5 | 27.5 | 0.5 | 27.5 | 0.5 | 22.5 | 1.25 | 47.5 | 1 | 12.5 | 0.5 | 47.5 | 1.75 | 20 | 0.5 | 27.5 | 1.25 |
| 124 | 1 | MMBYSSSMMKPR/BORG/0945/03 | 32.85714286 | 1 | 12.5 | 1.5 | 22.5 | 1.25 | 22.5 | 1.25 | 50 | 1.25 | 47.5 | 2 | 47.5 | 0.5 | 20 | 1.25 | 30 | 1 | 22.5 | 1 |
| 125 | 1 | MMBYSSSMMKPR/BPRG/3398/03 | 18.57142857 | 1 | 40 | 0.5 | 12.5 | 0.5 | 12.5 | 0.5 | 52.5 | 1.25 | 12.5 | 1.5 | 20 | 1.25 | 12.5 | 0.5 | 20 | 0.5 | 27.5 | 1.5 |
| 126 | 1 | MMBYSSSMMKPR/BQRG/4390/03 | 15.71428571 | 1.25 | 32.5 | 0.5 | 25 | 1.25 | 50 | 1.5 | 40 | 1.25 | 32.5 | 1.25 | 32.5 | 0.5 | 17.5 | 1.25 | 44 | 1.25 | 22.5 | 1 |
| 127 | 1 | MMBYSSSMMKPR/BTRG/3606/03 | 35.71428571 | 2 | 12.5 | 0.5 | 12.5 | 0.5 | 52.5 | 0.5 | 12.5 | 0.5 | 42.5 | 1.25 | 37.5 | 0.5 | 12.5 | 0.5 | 28 | 0.5 | 12.5 | 1.25 |
| 128 | 1 | MMBYSSSMMKPR/BUMH/6186/04 | 12.85714286 | 0.5 | 12.5 | 0.5 | 25 | 0.5 | 40 | 1.25 | 12.5 | 1.5 | 20 | 1.5 | 20 | 1.25 | 50 | 1.75 | 34 | 1.5 | 12.5 | 0.5 |
| 129 | 1 | MMBYSSSMMKPR/BVMH/6080/07 | 12.85714286 | 0.5 | 12.5 | 0.5 | 40 | 1.5 | 55 | 1.5 | 47.5 | 1.25 | 47.5 | 1.25 | 30 | 0.5 | 17.5 | 1.25 | 20 | 0.5 | 42.5 | 0.5 |
| 130 | 1 | MMBYSSSMMKPR/DMMX/3990/07 | 22.85714286 | 1.25 | 40 | 1.75 | 42.5 | 1.75 | 47.5 | 1.5 | 42.5 | 1.5 | 45 | 1.75 | 52.5 | 2 | 50 | 1.25 | 26 | 1.25 | 47.5 | 1.75 |
| 131 | 1 | MMBYSSSMMKPR/SP1/2238/01 | 15.71428571 | 1.25 | 52.5 | 1.5 | 25 | 1.25 | 52.5 | 1.25 | 42.5 | 1.25 | 47.5 | 1.25 | 42.5 | 1 | 12.5 | 1.5 | 30 | 1 | 42.5 | 1.25 |
| 132 | 1 | MMBYSSSMMKPR/RG15/1464/08 | 12.85714286 | 0.5 | 47.5 | 1.5 | 22.5 | 1 | 52.5 | 1.5 | 52.5 | 1.75 | 52.5 | 1.75 | 12.5 | 0.5 | 47.5 | 1.5 | 20 | 0.5 | 52.5 | 1.5 |
| 133 | 1 | MMBYSSSMMKPR/RG22/1931/09 | 17.14285714 | 1 | 52.5 | 1.75 | 22.5 | 1 | 47.5 | 1.5 | 52.5 | 1.5 | 52.5 | 1.75 | 12.5 | 1.25 | 12.5 | 0.5 | 20 | 1.5 | 37.5 | 1.5 |
| 134 | 1 | MMBYSSSMMKPR/MH14/6324/08 | 17.14285714 | 1.25 | 47.5 | 1 | 52.5 | 1 | 52.5 | 1.75 | 52.5 | 1.25 | 52.5 | 1.75 | 50 | 1.25 | 50 | 2 | 38 | 1.5 | 52.5 | 1.5 |
| 135 | 1 | MMBYSSSMMKPR/RG24/805/09 | 21.42857143 | 1 | 47.5 | 1.25 | 45 | 1.5 | 52.5 | 1.25 | 47.5 | 1.5 | 50 | 1.5 | 17.5 | 0.5 | 12.5 | 0.5 | 24 | 0.5 | 45 | 1.5 |
| 136 | 1 | MMBYSSSMMKPR/HCGA4/6374/08 | 21.42857143 | 1 | 47.5 | 1.5 | 47.5 | 1.25 | 47.5 | 1.25 | 45 | 1.5 | 42.5 | 1.5 | 25 | 1 | 12.5 | 1.25 | 24 | 1 | 50 | 1.5 |
| 137 | 1 | MMBYSSSMMKPR/SP1/3187/99 | 15.71428571 | 1 | 47.5 | 1.75 | 17.5 | 0.5 | 50 | 1.75 | 47.5 | 1.5 | 27.5 | 1.25 | 37.5 | 0.5 | 12.5 | 0.5 | 44 | 1 | 50 | 1.5 |
| 138 | 1 | MMBYSSSMMKPR/SP1/1543/00 | 27.14285714 | 1.25 | 47.5 | 1.5 | 47.5 | 1.5 | 52.5 | 1.5 | 52.5 | 1.5 | 52.5 | 1.5 | 17.5 | 1.25 | 17.5 | 1.25 | 36 | 1.5 | 55 | 1.5 |
| 139 | 1 | MMBYSSSMMKPR/SP2/10817/07 | 17.14285714 | 1.5 | 55 | 1.5 | 37.5 | 1.25 | 45 | 1.25 | 50 | 1 | 52.5 | 1.25 | 12.5 | 0.5 | 12.5 | 0.5 | 34 | 1.25 | 47.5 | 1.5 |
| 140 | 1 | MMBYSSSMMKPR/SP2/3424/03 | 24.28571429 | 1.25 | 45 | 1.25 | 27.5 | 1.25 | 40 | 1.25 | 52.5 | 1.25 | 42.5 | 0.5 | 12.5 | 0.5 | 35 | 1.25 | 26 | 1.5 | 42.5 | 1.5 |
| 141 | 1 | MMBYSSSMMKPR/SP2/489/02 | 15.71428571 | 1.25 | 47.5 | 1.75 | 52.5 | 1.75 | 55 | 1.5 | 42.5 | 1 | 50 | 1.5 | 45 | 0.5 | 12.5 | 1.5 | 38 | 1.5 | 55 | 1.75 |
| 142 | 1 | MMBYSSSMMKPR/SP3/5454/05 | 27.14285714 | 1 | 55 | 1.75 | 47.5 | 1.5 | 52.5 | 1.75 | 47.5 | 1.5 | 47.5 | 1.5 | 12.5 | 0.5 | 12.5 | 0.5 | 24 | 1.5 | 55 | 1.5 |
| 143 | 1 | MMBYSSSMMKPR/SP3/00070/06 | 15.71428571 | 1.25 | 52.5 | 1.75 | 17.5 | 1.25 | 42.5 | 1.75 | 52.5 | 1.75 | 52.5 | 1.75 | 17.5 | 0.5 | 12.5 | 0.5 | 28 | 1.5 | 50 | 2 |
| 144 | 1 | MMBYSSSMMKPR/SP4/11639/06 | 18.57142857 | 1 | 50 | 1.5 | 42.5 | 1.75 | 47.5 | 1.75 | 52.5 | 1 | 52.5 | 1 | 12.5 | 0.5 | 12.5 | 0.5 | 28 | 1.25 | 47.5 | 1.5 |
| 145 | 1 | MMBYSSSMMKPR/SP4/12823/07 | 12.85714286 | 0.5 | 47.5 | 1.75 | 17.5 | 1.25 | 47.5 | 1.5 | 50 | 1.5 | 52.5 | 1.75 | 12.5 | 0.5 | 12.5 | 0.5 | 24 | 1.25 | 55 | 1.5 |

TABLE 3B-continued

| Sl. No | Outcome | Sample No. | F %-M | FI-M | F %-C | FI-C | K %-M | KI-M | K %-C | KI-C | M %-C | MI-C | N %-C | NI-C | O %-M | OI-M | P %-N | PI-N | R %-M | RI-M | R %-C | RI-C |
|---|---|---|---|---|---|---|---|---|---|---|---|---|---|---|---|---|---|---|---|---|---|---|
| 146 | 1 | MMBVSSSSMMKPR/SP4/14511/07 | 24.28571429 | 1.5 | 52.5 | 0.5 | 35 | 1.5 | 47.5 | 1.75 | 50 | 1.5 | 50 | 1.5 | 17.5 | 1 | 12.5 | 0.5 | 30 | 1.5 | 12.5 | 1.75 |
| 147 | 1 | MMBVSSSSMMKPR/IIRG/4358/08 | 12.85714286 | 0.5 | 12.5 | 1.5 | 32.5 | 1.5 | 47.5 | 1.75 | 42.5 | 1.75 | 37.5 | 1.5 | 42.5 | 1.75 | 12.5 | 0.5 | 26 | 1 | 42.5 | 0.5 |
| 148 | 1 | MMBVSSSSMMKPR/IVRG/1658/08 | 25.71428571 | 1.5 | 47.5 | 1.25 | 12.5 | 0.5 | 37.5 | 1.5 | 25 | 1 | 30 | 1 | 12.5 | 0.5 | 22.5 | 1 | 34 | 1.25 | 47.5 | 1.5 |
| 149 | 1 | MMBVSSSSMMKPR/JRRG/6716/08 | 15.71428571 | 1 | 47.5 | 1.25 | 27.5 | 1.25 | 50 | 2 | 50 | 1.25 | 50 | 1.75 | 12.5 | 0.5 | 52.5 | 1.25 | 30 | 1 | 20 | 1.25 |
| 150 | 1 | MMBVSSSSMMKPR/JSMH/7129/07 | 12.85714286 | 0.5 | 37.5 | 1.75 | 40 | 2 | 47.5 | 2 | 32.5 | 1.25 | 37.5 | 1.5 | 37.5 | 1.5 | 45 | 2 | 20 | 0.5 | 50 | 1.25 |
| 151 | 0 | MMBVSSSSMMKPR/CPMH/1187/05 | 22.85714 | 1.25 | 47.5 | 0.5 | 45 | 1.5 | 57.5 | 2 | 42.5 | 1.75 | 12.5 | 0.5 | 45 | 1.75 | 47.5 | 1.5 | 48 | 1.25 | 17.5 | 1.5 |
| 152 | 0 | MMBVSSSSMMKPR/CSMH/3038/04 | 35.71429 | 1.25 | 12.5 | 0.5 | 32.5 | 1.25 | 52.5 | 2 | 50 | 1.75 | 47.5 | 1.75 | 52.5 | 1.25 | 12.5 | 0.5 | 20 | 0.5 | 27.5 | 1.5 |
| 153 | 0 | MMBVSSSSMMKPR/CTMH/2852/04 | 12.85714 | 0.5 | 12.5 | 1.5 | 37.5 | 1.75 | 55 | 1.75 | 52.5 | 1.75 | 52.5 | 1.75 | 27.5 | 1.25 | 57.5 | 2 | 52 | 1.25 | 50 | 1 |
| 154 | 0 | MMBVSSSSMMKPR/CUMH/1591/03 | 17.14286 | 1.25 | 55 | 1.75 | 12.5 | 0.5 | 52.5 | 2 | 32.5 | 2 | 52.5 | 1 | 20 | 1.25 | 12.5 | 0.5 | 30 | 1 | 17.5 | 1.25 |
| 155 | 0 | MMBVSSSSMMKPR/CWMH/3473/06 | 20 | 1.25 | 47.5 | 1.5 | 27.5 | 1.75 | 32.5 | 0.5 | 12.5 | 0.5 | 27.5 | 2 | 45 | 1.75 | 12.5 | 2 | 20 | 0.5 | 27.5 | 1 |
| 156 | 0 | MMBVSSSSMMKPR/CXJH/3121/05 | 35.71429 | 1.25 | 47.5 | 1.5 | 32.5 | 1.5 | 55 | 2 | 47.5 | 1.75 | 50 | 1.25 | 12.5 | 0.5 | 45 | 0.5 | 34 | 1.25 | 42.5 | 1.5 |
| 157 | 0 | MMBVSSSSMMKPR/CYJH/0878/06 | 18.57143 | 1.25 | 52.5 | 1.5 | 55 | 1.75 | 52.5 | 2 | 12.5 | 0.5 | 37.5 | 1.75 | 20 | 1.25 | 12.5 | 1.25 | 24 | 1.75 | 52.5 | 1.5 |
| 158 | 0 | MMBVSSSSMMKPR/RG26/5002/09 | 34.28571 | 1.25 | 52.5 | 1.25 | 47.5 | 1.25 | 52.5 | 1.75 | 42.5 | 1.25 | 50 | 1.75 | 20 | 1.25 | 27.5 | 1.25 | 28 | 1.25 | 37.5 | 1.75 |
| 159 | 0 | MMBVSSSSMMKPR/DAMH/7095/09 | 34.28571 | 1.25 | 35 | 1.5 | 52.5 | 1.5 | 22.5 | 1.5 | 12.5 | 0.5 | 12.5 | 0.5 | 37.5 | 1.5 | 57.5 | 2 | 44 | 1.25 | 22.5 | 1.25 |
| 160 | 0 | MMBVSSSSMMKPR/DBMH/9616/08 | 24.28571 | 1.5 | 52.5 | 1 | 30 | 1.5 | 35 | 1.5 | 25 | 1.5 | 22.5 | 1 | 57.5 | 1.75 | 42.5 | 1.25 | 24 | 1.25 | 22.5 | 1 |

TABLE 3C

| Sl. No | Outcome | Sample No. | U%-M | UI-M | U%-C | UI-C | V%-M | VI-M | V%-C | VI-C | W%-M | WI-M | W%-C | WI-C | ZA1%-M | ZAI1-M | ZA1%-C | ZAI1-C | ZB%-C |
|---|---|---|---|---|---|---|---|---|---|---|---|---|---|---|---|---|---|---|---|
| 1 | 1 | MMBYSSSSMMKPR/AAJH/0467/06 | 42.5 | 1.5 | 56.36363636 | 2 | 60 | 2 | 10 | 0.25 | 52.5 | 2 | 50 | 2 | 47.5 | 1.75 | 37.5 | 1.5 | 37.5 |
| 2 | 1 | MMBYSSSSMMKPR/ABMH/4734/07 | 42.5 | 1.75 | 49.09090909 | 2 | 60 | 2 | 10 | 0.25 | 60 | 2 | 7.5 | 0.5 | 47.5 | 1.5 | 42.5 | 1.5 | 37.5 |
| 3 | 1 | MMBYSSSSMMKPR/HLRG/1219/03 | 27.5 | 1.25 | 38.18181818 | 2 | 15 | 0.5 | 20 | 1.25 | 47.5 | 1.75 | 47.5 | 1.75 | 50 | 1.75 | 37.5 | 1.25 | 42.5 |
| 4 | 1 | MMBYSSSSMMKPR/ACRG/2834/03 | 27.5 | 1.5 | 52.72727273 | 1.75 | 55 | 1.5 | 10 | 0.25 | 52.5 | 1.25 | 42.5 | 1.5 | 17.5 | 1 | 42.5 | 1.5 | 57.5 |
| 5 | 1 | MMBYSSSSMMKPR/AVRG/1397/04 | 22.5 | 1.5 | 54.54545455 | 2 | 22.5 | 1.25 | 25 | 1.25 | 27.5 | 1.25 | 50 | 1.5 | 22.5 | 1 | 42.5 | 1.25 | 52.5 |
| 6 | 1 | MMBYSSSSMMKPR/AEMH/6521/06 | 12.5 | 0.5 | 47.27272727 | 2 | 30 | 1.25 | 10 | 0.25 | 27.5 | 1.25 | 27.5 | 1.75 | 32.5 | 1.75 | 12.5 | 0.5 | 37.5 |
| 7 | 1 | MMBYSSSSMMKPR/AFJH/0478/06 | 32.5 | 1.25 | 50.90909091 | 1.75 | 55 | 2 | 10 | 0.25 | 52.5 | 1.5 | 12.5 | 1.75 | 12.5 | 0.5 | 12.5 | 0.5 | 47.5 |
| 8 | 1 | MMBYSSSSMMKPR/HTMX/0675/08 | 17.5 | 1 | 34.54545455 | 1.5 | 40 | 1.5 | 40 | 1.25 | 25 | 1.5 | 37.5 | 1.75 | 47.5 | 1.75 | 37.5 | 1.5 | 47.5 |
| 9 | 1 | MMBYSSSSMMKPR/IRRG/5724/08 | 47.5 | 1.5 | 41.81818182 | 1.75 | 50 | 1.5 | 45 | 1.25 | 45 | 1 | 37.5 | 1.75 | 47.5 | 1.5 | 37.5 | 1 | 52.5 |
| 10 | 1 | MMBYSSSSMMKPR/JMRG/1480/08 | 22.5 | 1 | 49.09090909 | 1.75 | 60 | 1.75 | 47.5 | 1 | 52.5 | 2 | 42.5 | 2 | 22.5 | 1.25 | 50 | 1.75 | 42.5 |
| 11 | 1 | MMBYSSSSMMKPR/HCGA1/222/10 | 17.5 | 1.25 | 49.09090909 | 1.25 | 55 | 1.5 | 40 | 1 | 47.5 | 1.25 | 32.5 | 1.25 | 42.5 | 1.75 | 12.5 | 0.5 | 42.5 |
| 12 | 1 | MMBYSSSSMMKPR/KIDC/0164/06 | 32.5 | 1 | 52.72727273 | 1.75 | 55 | 2 | 10 | 0.25 | 45 | 1.5 | 47.5 | 1.5 | 47.5 | 2 | 12.5 | 0.5 | 47.5 |
| 13 | 1 | MMBYSSSSMMKPR/KJDC/0167/06 | 22.5 | 1 | 49.09090909 | 1.25 | 55 | 2 | 35 | 1.75 | 52.5 | 1.5 | 32.5 | 1.5 | 45 | 1.75 | 12.5 | 0.5 | 50 |
| 14 | 1 | MMBYSSSSMMKPR/KNDC/0176/05 | 32.5 | 1 | 49.09090909 | 1.25 | 45 | 1.25 | 50 | 1.5 | 47.5 | 1.5 | 42.5 | 1.5 | 55 | 2 | 47.5 | 1.75 | 47.5 |
| 15 | 1 | MMBYSSSSMMKPR/MH11/3187/09 | 42.5 | 1.5 | 50.90909091 | 1.5 | 50 | 1.25 | 40 | 1 | 42.5 | 1.5 | 47.5 | 1.75 | 47.5 | 1.5 | 47.5 | 1.5 | 47.5 |
| 16 | 1 | MMBYSSSSMMKPR/HCGA4/5535/06 | 12.5 | 1.5 | 50.90909091 | 1.5 | 15 | 0.5 | 10 | 1 | 45 | 1.5 | 17.5 | 1.25 | 17.5 | 1.5 | 17.5 | 1 | 52.5 |
| 17 | 1 | MMBYSSSSMMKPR/SP5/6544/08 | 12.5 | 0.5 | 49.09090909 | 1.5 | 15 | 0.5 | 10 | 0.25 | 25 | 1.5 | 12.5 | 0.5 | 12.5 | 0.5 | 47.5 | 1.25 | 47.5 |
| 18 | 1 | MMBYSSSSMMKPR/SP6/5298/06 | 37.5 | 1.25 | 52.72727273 | 1.75 | 55 | 1.75 | 50 | 1.25 | 50 | 1.5 | 7.5 | 0.5 | 50 | 1.5 | 50 | 1.5 | 45 |
| 19 | 1 | MMBYSSSSMMKPR/SP6/6116/06 | 27.5 | 1 | 49.09090909 | 1.5 | 55 | 1.5 | 50 | 1.5 | 50 | 1.5 | 42.5 | 1.75 | 50 | 1.75 | 50 | 1.75 | 52.5 |
| 20 | 1 | MMBYSSSSMMKPR/SP8/6543/06 | 52.5 | 1.5 | 52.72727273 | 1.75 | 55 | 1.5 | 45 | 1.5 | 52.5 | 1.5 | 47.5 | 1.5 | 52.5 | 1.75 | 52.5 | 1.75 | 52.5 |
| 21 | 1 | MMBYSSSSMMKPR/SP9/1761/97 | 37.5 | 1.5 | 52.72727273 | 1.75 | 32.5 | 1.5 | 45 | 1.75 | 32.5 | 1.75 | 47.5 | 1.75 | 37.5 | 1.5 | 40 | 1.25 | 52.5 |
| 22 | 1 | MMBYSSSSMMKPR/SP9/2006/02 | 27.5 | 1.25 | 49.09090909 | 1.75 | 42.5 | 1.75 | 45 | 1.5 | 47.5 | 1.75 | 45 | 1.5 | 50 | 1.75 | 42.5 | 1 | 47.5 |
| 23 | 1 | MMBYSSSSMMKPR/SP10/4338/05 | 12.5 | 0.5 | 49.09090909 | 1.25 | 47.5 | 1.75 | 47.5 | 1.5 | 52.5 | 1.5 | 42.5 | 1.5 | 52.5 | 2 | 47.5 | 1.75 | 47.5 |
| 24 | 1 | MMBYSSSSMMKPR/SP13/0242/10 | 47.5 | 1.25 | 52.72727273 | 1.75 | 55 | 1.5 | 50 | 1.25 | 50 | 1.5 | 47.5 | 1.25 | 52.5 | 1.5 | 47.5 | 1.5 | 47.5 |
| 25 | 1 | MMBYSSSSMMKPR/ADRG/1440/02 | 32.5 | 1.5 | 49.09090909 | 1.75 | 40 | 1.5 | 10 | 0.25 | 27.5 | 1 | 42.5 | 1.25 | 57.5 | 1.5 | 12.5 | 0.5 | 42.5 |
| 26 | 1 | MMBYSSSSMMKPR/AGMH/2268/04 | 12.5 | 0.5 | 50.90909091 | 2 | 55 | 2 | 55 | 1.25 | 50 | 2 | 7.5 | 0.5 | 42.5 | 1.75 | 32.5 | 1.5 | 52.5 |
| 27 | 1 | MMBYSSSSMMKPR/AHMH/2180/03 | 32.5 | 1.25 | 49.09090909 | 1.75 | 60 | 2 | 20 | 0.25 | 57.5 | 1.75 | 27.5 | 1.25 | 52.5 | 1.75 | 20 | 1.25 | 50 |
| 28 | 1 | MMBYSSSSMMKPR/AJMH/1975/03 | 37.5 | 1.25 | 52.72727273 | 1.25 | 60 | 2 | 10 | 0.25 | 55 | 2 | 7.5 | 0.5 | 57.5 | 2 | 12.5 | 0.5 | 37.5 |
| 29 | 1 | MMBYSSSSMMKPR/AKMH/1186/03 | 12.5 | 0.5 | 56.36363636 | 1.5 | 60 | 2 | 37.5 | 1.5 | 60 | 2 | 22.5 | 0.5 | 27.5 | 1 | 52.5 | 1.75 | 57.5 |
| 30 | 1 | MMBYSSSSMMKPR/ALMH/4227/05 | 20 | 1.25 | 38.18181818 | 1.25 | 37.5 | 1.5 | 10 | 0.25 | 45 | 2 | 7.5 | 0.5 | 52.5 | 2 | 12.5 | 0.5 | 42.5 |
| 31 | 1 | MMBYSSSSMMKPR/AMMH/2138/05 | 22.5 | 1.25 | 27.27272727 | 1.25 | 60 | 2 | 10 | 0.25 | 57.5 | 2 | 7.5 | 0.5 | 47.5 | 2 | 12.5 | 1.5 | 37.5 |
| 32 | 1 | MMBYSSSSMMKPR/ANMH/6528/05 | 22.5 | 1.25 | 52.72727273 | 2 | 60 | 2 | 55 | 1.75 | 52.5 | 2 | 22.5 | 0.5 | 12.5 | 0.5 | 37.5 | 1.5 | 42.5 |
| 33 | 1 | MMBYSSSSMMKPR/AOMH/1621/05 | 37.5 | 2 | 34.54545455 | 1.5 | 55 | 1.5 | 55 | 1.5 | 52.5 | 1.75 | 42.5 | 2 | 27.5 | 1.5 | 27.5 | 1.5 | 30 |
| 34 | 1 | MMBYSSSSMMKPR/APMH/6408/05 | 42.5 | 1.25 | 52.72727273 | 1.75 | 57.5 | 1.75 | 10 | 0.25 | 55 | 2 | 47.5 | 1.75 | 42.5 | 1.75 | 32.5 | 1.75 | 37.5 |
| 35 | 1 | MMBYSSSSMMKPR/AQMH/1408/06 | 47.5 | 2 | 52.72727273 | 2 | 60 | 2 | 10 | 0.25 | 57.5 | 2 | 22.5 | 1.25 | 50 | 2 | 47.5 | 0.5 | 25 |
| 36 | 1 | MMBYSSSSMMKPR/ARMH/4622/06 | 32.5 | 1.25 | 52.72727273 | 1.75 | 60 | 1.75 | 20 | 1.25 | 42.5 | 1.5 | 32.5 | 1.25 | 60 | 1.75 | 12.5 | 0.5 | 55 |
| 37 | 1 | MMBYSSSSMMKPR/ASRG/5174/03 | 20 | 1 | 41.81818182 | 1.5 | 35 | 1.25 | 50 | 1.5 | 27.5 | 1.25 | 32.5 | 1.5 | 32.5 | 1.25 | 32.5 | 1.5 | 47.5 |
| 38 | 1 | MMBYSSSSMMKPR/ATMH/4074/01 | 30 | 1.75 | 49.09090909 | 2 | 15 | 0.5 | 40 | 1.75 | 37.5 | 1.25 | 37.5 | 1.5 | 42.5 | 1.25 | 12.5 | 0.5 | 27.5 |
| 39 | 1 | MMBYSSSSMMKPR/AYRG/3670/02 | 12.5 | 0.5 | 50.90909091 | 1.5 | 15 | 0.5 | 45 | 1.25 | 22.5 | 0.5 | 37.5 | 0.5 | 17.5 | 0.5 | 37.5 | 1.5 | 47.5 |
| 40 | 1 | MMBYSSSSMMKPR/AZRG/1472/02 | 20 | 1.25 | 47.27272727 | 1.5 | 22.5 | 1 | 25 | 1.25 | 22.5 | 1.5 | 37.5 | 0.5 | 12.5 | 0.5 | 12.5 | 1.5 | 52.5 |
| 41 | 1 | MMBYSSSSMMKPR/BAJH/0102/07 | 40 | 1.75 | 50.90909091 | 2 | 45 | 1.5 | 20 | 1.25 | 45 | 1.5 | 42.5 | 1.5 | 47.5 | 1.5 | 47.5 | 0.5 | 42.5 |
| 42 | 1 | MMBYSSSSMMKPR/HSMH/4789/07 | 27.5 | 1 | 49.09090909 | 2 | 15 | 0.5 | 52.5 | 1.75 | 22.5 | 1 | 37.5 | 1.25 | 27.5 | 1.25 | 37.5 | 2 | 32.5 |
| 43 | 1 | MMBYSSSSMMKPR/HKRG/3754/03 | 12.5 | 0.5 | 49.09090909 | 1.5 | 15 | 0.5 | 42.5 | 1.25 | 52.5 | 1 | 37.5 | 1.5 | 42.5 | 1 | 12.5 | 0.5 | 47.5 |
| 44 | 1 | MMBYSSSSMMKPR/IMRG/5141/08 | 12.5 | 0.5 | 47.27272727 | 2 | 15 | 0.5 | 10 | 0.25 | 22.5 | 0.5 | 37.5 | 1.5 | 17.5 | 1.25 | 52.5 | 1.25 | 47.5 |
| 45 | 1 | MMBYSSSSMMKPR/IQRG/5751/08 | 12.5 | 0.5 | 52.72727273 | 1.5 | 15 | 0.5 | 10 | 0.25 | 32.5 | 1.25 | 47.5 | 1.5 | 27.5 | 1.5 | 12.5 | 1.75 | 27.5 |
| 46 | 1 | MMBYSSSSMMKPR/JNRG/6963/08 | 32.5 | 1.25 | 49.09090909 | 1.5 | 25 | 1.25 | 45 | 1.5 | 52.5 | 1.5 | 27.5 | 1.5 | 37.5 | 1.5 | 42.5 | 1.5 | 47.5 |
| 47 | 1 | MMBYSSSSMMKPR/JORG/6520/08 | 27.5 | 1.25 | 54.54545455 | 2 | 52.5 | 1.75 | 52.5 | 1.25 | 52.5 | 2 | 42.5 | 1.5 | 42.5 | 1.75 | 42.5 | 1.75 | 42.5 |
| 48 | 1 | MMBYSSSSMMKPR/IXRG/1912/08 | 12.5 | 0.5 | 58.18181818 | 2 | 45 | 1.5 | 37.5 | 1.25 | 27.5 | 1.25 | 37.5 | 1.75 | 27.5 | 1.5 | 42.5 | 1.5 | 57.5 |

TABLE 3C-continued

| Sl. No | Outcome | Sample No. | U %-M | UI-M | U %-C | UI-C | V %-M | VI-M | V %-C | VI-C | W %-M | WI-M | W %-C | WI-C | ZA1 %-M | ZA1I-M | ZA1 %-C | ZA1I-C | ZB %-C |
|---|---|---|---|---|---|---|---|---|---|---|---|---|---|---|---|---|---|---|---|
| 49 | 1 | MMBVSSSSMMKPR/IHRG/1461/07 | 37.5 | 1 | 52.72727273 | 2 | 55 | 2 | 20 | 1.25 | 47.5 | 2 | 32.5 | 1.75 | 57.5 | 2 | 12.5 | 0.5 | 47.5 |
| 50 | 1 | MMBVSSSSMMKPR/INRG/6074/08 | 12.5 | 0.5 | 50.90909091 | 2 | 15 | 0.5 | 10 | 0.25 | 42.5 | 1.5 | 22.5 | 1.25 | 12.5 | 0.5 | 52.5 | 2 | 55 |
| 51 | 1 | MMBVSSSSMMKPR/JPRG/7119/08 | 12.5 | 0.5 | 34.54545455 | 1 | 55 | 1.5 | 45 | 1.5 | 52.5 | 1.75 | 42.5 | 0.5 | 52.5 | 1.25 | 42.5 | 1.75 | 27.5 |
| 52 | 1 | MMBVSSSSMMKPR/JARG/1209/01 | 37.5 | 1 | 38.18181818 | 1 | 45 | 1.5 | 20 | 1.5 | 42.5 | 1.75 | 7.5 | 2 | 35 | 1.75 | 37.5 | 1.25 | 27.5 |
| 53 | 1 | MMBVSSSSMMKPR/JQRG/6998/08 | 25 | 1 | 54.54545455 | 1.75 | 57.5 | 1.75 | 22.5 | 1.25 | 55 | 2 | 42.5 | 1.5 | 52.5 | 1.75 | 47.5 | 1.5 | 37.5 |
| 54 | 1 | MMBVSSSSMMKPR/HCGA1/5042/08 | 17.5 | 1 | 52.72727273 | 1 | 40 | 1 | 27.5 | 0.75 | 52.5 | 1.5 | 22.5 | 1.5 | 22.5 | 1 | 37.5 | 1 | 42.5 |
| 55 | 1 | MMBVSSSSMMKPR/RG20/7272/08 | 37.5 | 1.25 | 52.72727273 | 1.75 | 50 | 1.5 | 45 | 1.5 | 47.5 | 1.5 | 42.5 | 1.5 | 45 | 1.5 | 47.5 | 1.25 | 52.5 |
| 56 | 1 | MMBVSSSSMMKPR/MH10/826/06 | 12.5 | 0.5 | 32.72727273 | 0.5 | 50 | 1.5 | 45 | 1.5 | 47.5 | 1.5 | 35 | 1.25 | 27.5 | 1.25 | 17.5 | 1.25 | 27.5 |
| 57 | 1 | MMBVSSSSMMKPR/MH12/6907/09 | 37.5 | 1.25 | 52.72727273 | 1.5 | 45 | 1.5 | 45 | 1.5 | 45 | 1.5 | 32.5 | 1 | 45 | 1.5 | 37.5 | 1.25 | 52.5 |
| 58 | 1 | MMBVSSSSMMKPR/MH13/5276/09 | 47.5 | 1.5 | 52.72727273 | 1.5 | 40 | 1.5 | 50 | 1.25 | 45 | 1.5 | 32.5 | 1.5 | 50 | 1.5 | 37.5 | 1.25 | 47.5 |
| 59 | 1 | MMBVSSSSMMKPR/MH13/2852/02 | 32.5 | 1.5 | 52.72727273 | 1.5 | 57.5 | 1.75 | 50 | 1.25 | 55 | 1.5 | 50 | 1 | 12.5 | 0.5 | 37.5 | 1.25 | 42.5 |
| 60 | 1 | MMBVSSSSMMKPR/RG24/2672/09 | 17.5 | 1 | 52.72727273 | 1.5 | 20 | 1 | 50 | 1.25 | 17.5 | 1 | 12.5 | 1.25 | 50 | 1.5 | 37.5 | 0.75 | 52.5 |
| 61 | 1 | MMBVSSSSMMKPR/RG24/786/09 | 32.5 | 1.25 | 49.09090909 | 1.25 | 40 | 1 | 35 | 1 | 47.5 | 1 | 42.5 | 1.5 | 12.5 | 1 | 22.5 | 1 | 42.5 |
| 62 | 1 | MMBVSSSSMMKPR/RG24/3773/09 | 32.5 | 1.5 | 52.72727273 | 1.5 | 55 | 1.75 | 50 | 1 | 50 | 1.5 | 45 | 1.75 | 47.5 | 1.5 | 47.5 | 1.5 | 47.5 |
| 63 | 1 | MMBVSSSSMMKPR/RG24/3821/09 | 20 | 1.25 | 52.72727273 | 1.5 | 25 | 1.5 | 47.5 | 1.5 | 42.5 | 1.5 | 37.5 | 1.5 | 25 | 1.25 | 25 | 1 | 32.5 |
| 64 | 1 | MMBVSSSSMMKPR/RG25/1072/09 | 27.5 | 1 | 49.09090909 | 1 | 15 | 0.5 | 20 | 0.75 | 27.5 | 1 | 37.5 | 1.5 | 12.5 | 0.5 | 25 | 1 | 52.5 |
| 65 | 1 | MMBVSSSSMMKPR/HCGA5/7545/07 | 47.5 | 1.5 | 50.90909091 | 1.25 | 50 | 1.5 | 40 | 1 | 52.5 | 1.5 | 47.5 | 1.5 | 52.5 | 1.5 | 47.5 | 1.25 | 52.5 |
| 66 | 1 | MMBVSSSSMMKPR/SP2/2851/03 | 17.5 | 1 | 49.09090909 | 1.25 | 30 | 1.25 | 52.5 | 1 | 55 | 1.75 | 50 | 1.5 | 22.5 | 1 | 50 | 1.5 | 47.5 |
| 67 | 1 | MMBVSSSSMMKPR/SP2/06011/08 | 32.5 | 1.5 | 52.72727273 | 1.5 | 27.5 | 1.5 | 52.5 | 1.5 | 27.5 | 1.5 | 50 | 1.5 | 25 | 1.25 | 50 | 1.75 | 52.5 |
| 68 | 1 | MMBVSSSSMMKPR/SP2/5595E/04 | 42.5 | 1.5 | 54.54545455 | 1.75 | 52.5 | 1.5 | 45 | 1.5 | 50 | 1.5 | 50 | 1.5 | 50 | 1.5 | 50 | 1.75 | 47.5 |
| 69 | 1 | MMBVSSSSMMKPR/SP3/12267/07 | 42.5 | 1.5 | 49.09090909 | 1.25 | 45 | 1.5 | 42.5 | 0.75 | 52.5 | 1.5 | 42.5 | 1.5 | 37.5 | 1.5 | 37.5 | 1.5 | 52.5 |
| 70 | 1 | MMBVSSSSMMKPR/SP3/09935/08 | 45 | 1.5 | 50.90909091 | 1.75 | 57.5 | 1.75 | 35 | 1 | 55 | 1.75 | 50 | 1.5 | 52.5 | 1.5 | 50 | 1.5 | 47.5 |
| 71 | 1 | MMBVSSSSMMKPR/SP4/04418/08 | 17.5 | 1 | 50.90909091 | 1.75 | 27.5 | 1.25 | 47.5 | 1.5 | 27.5 | 1.25 | 50 | 1.25 | 25 | 1.25 | 50 | 1.75 | 52.5 |
| 72 | 1 | MMBVSSSSMMKPR/KFDC/0149/07 | 32.5 | 1 | 52.72727273 | 1.5 | 15 | 0.5 | 10 | 0.25 | 32.5 | 1.5 | 27.5 | 1.5 | 37.5 | 1.5 | 12.5 | 0.5 | 27.5 |
| 73 | 1 | MMBVSSSSMMKPR/BDRG/5248/06 | 12.5 | 0.5 | 50.90909091 | 1.25 | 45 | 1.25 | 40 | 1.25 | 45 | 1.25 | 42.5 | 1.75 | 50 | 2 | 47.5 | 2 | 40 |
| 74 | 1 | MMBVSSSSMMKPR/KODC/0178/05 | 22.5 | 1 | 41.81818182 | 1 | 25 | 0.5 | 25 | 1.25 | 22.5 | 0.5 | 20 | 1.5 | 37.5 | 2 | 12.5 | 0.5 | 22.5 |
| 75 | 1 | MMBVSSSSMMKPR/SP5/2503/08 | 17.5 | 1 | 52.72727273 | 1.5 | 55 | 1.5 | 45 | 1.5 | 55 | 1.75 | 42.5 | 1.75 | 55 | 1.75 | 55 | 1.75 | 52.5 |
| 76 | 1 | MMBVSSSSMMKPR/SP5/2049/09 | 52.5 | 1.5 | 54.54545455 | 1.5 | 55 | 1.5 | 50 | 1.5 | 55 | 1.75 | 50 | 1.5 | 55 | 1.75 | 50 | 1.5 | 52.5 |
| 77 | 1 | MMBVSSSSMMKPR/SP5/2933/09 | 52.5 | 1.5 | 50.90909091 | 1 | 50 | 1.5 | 25 | 0.75 | 52.5 | 1.5 | 45 | 1.5 | 55 | 1.75 | 42.5 | 1.5 | 32.5 |
| 78 | 1 | MMBVSSSSMMKPR/SP5/5414/09 | 12.5 | 0.5 | 50.90909091 | 1.5 | 50 | 1.5 | 45 | 1.25 | 50 | 1.5 | 42.5 | 1.5 | 25 | 1.5 | 50 | 1.5 | 47.5 |
| 79 | 1 | MMBVSSSSMMKPR/SP5/6317/09 | 12.5 | 0.5 | 52.72727273 | 1.25 | 52.5 | 1.5 | 50 | 1.5 | 47.5 | 1.5 | 45 | 1.5 | 52.5 | 1.75 | 47.5 | 1.5 | 50 |
| 80 | 1 | MMBVSSSSMMKPR/SP8/5630/07 | 52.5 | 1.5 | 50.90909091 | 1.5 | 25 | 1.25 | 47.5 | 1.5 | 35 | 1 | 45 | 1.5 | 20 | 1.5 | 27.5 | 1.75 | 52.5 |
| 81 | 1 | MMBVSSSSMMKPR/SP8/3347/09 | 45 | 1.5 | 52.72727273 | 1.75 | 55 | 1.5 | 50 | 1.25 | 42.5 | 1.5 | 42.5 | 1.5 | 47.5 | 1.75 | 50 | 1.5 | 45 |
| 82 | 1 | MMBVSSSSMMKPR/SP8/7252/08 | 40 | 1.25 | 50.90909091 | 1.5 | 55 | 1.5 | 47.5 | 1.25 | 55 | 1.5 | 45 | 1.5 | 40 | 1.5 | 50 | 1.5 | 50 |
| 83 | 1 | MMBVSSSSMMKPR/SP6/215/05 | 12.5 | 0.5 | 41.81818182 | 1 | 22.5 | 1.25 | 22.5 | 1.25 | 12.5 | 0.5 | 20 | 1.5 | 25 | 1.75 | 12.5 | 1.75 | 22.5 |
| 84 | 1 | MMBVSSSSMMKPR/SP6/4283/08 | 22.5 | 1 | 52.72727273 | 1.25 | 45 | 1.5 | 45 | 1.5 | 47.5 | 1.5 | 47.5 | 1.5 | 52.5 | 1.75 | 55 | 1.5 | 52.5 |
| 85 | 1 | MMBVSSSSMMKPR/SP6/3004/09 | 47.5 | 1.5 | 52.72727273 | 1.75 | 55 | 1.5 | 25 | 1.25 | 50 | 1.5 | 45 | 1.5 | 50 | 1.5 | 50 | 1.5 | 32.5 |
| 86 | 1 | MMBVSSSSMMKPR/HCGA3/5860/09 | 22.5 | 1.25 | 52.72727273 | 1.5 | 55 | 1.5 | 45 | 1.5 | 52.5 | 1.75 | 45 | 1.5 | 52.5 | 1.75 | 47.5 | 1.5 | 52.5 |
| 87 | 1 | MMBVSSSSMMKPR/SP7/7675/07 | 22.5 | 1 | 52.72727273 | 1.5 | 35 | 1 | 50 | 1.25 | 35 | 1.5 | 37.5 | 1.5 | 25 | 1.5 | 47.5 | 1.5 | 47.5 |
| 88 | 1 | MMBVSSSSMMKPR/SP7/4924/06 | 12.5 | 0.5 | 50.90909091 | 1 | 47.5 | 1.5 | 47.5 | 1.5 | 47.5 | 1.5 | 42.5 | 1.5 | 20 | 1.5 | 27.5 | 1.5 | 47.5 |
| 89 | 1 | MMBVSSSSMMKPR/SP8/7537/09 | 45 | 1.5 | 49.09090909 | 1.5 | 32.5 | 1.5 | 50 | 1.25 | 50 | 1.5 | 42.5 | 1.5 | 47.5 | 1.5 | 50 | 1.5 | 45 |
| 90 | 1 | MMBVSSSSMMKPR/AURG/1691/04 | 35 | 1.25 | 52.72727273 | 1 | 55 | 1.5 | 47.5 | 1.25 | 50 | 1.5 | 42.5 | 1.5 | 50 | 1.5 | 50 | 1.5 | 50 |
| 91 | 1 | MMBVSSSSMMKPR/AWRG/3418/04 | 22.5 | 1.25 | 43.63636364 | 1.5 | 40 | 1.25 | 22.5 | 0.25 | 32.5 | 1 | 15 | 1 | 42.5 | 1.5 | 37.5 | 1.5 | 42.5 |
| 92 | 1 | MMBVSSSSMMKPR/HCGA1/6737/09 | 27.5 | 1.5 | 49.09090909 | 0.5 | 25 | 1 | 10 | 1 | 27.5 | 1.5 | 7.5 | 0.5 | 27.5 | 1.25 | 47.5 | 1.75 | 47.5 |
| 93 | 1 | MMBVSSSSMMKPR/SP7/4665/07 | 12.5 | 0.5 | 52.72727273 | 1.25 | 55 | 1.5 | 40 | 0.25 | 50 | 1.5 | 17.5 | 1.25 | 42.5 | 1.5 | 25 | 1 | 32.5 |
| 94 | 1 | MMBVSSSSMMKPR/HCGA3/5860/09 | 22.5 | 1 | 52.72727273 | 1.75 | 35 | 1.5 | 50 | 1.5 | 22.5 | 1.5 | 32.5 | 1.25 | 47.5 | 1.5 | 42.5 | 1.5 | 52.5 |
| 95 | 1 | MMBVSSSSMMKPR/BBMH/6814/07 | 17.5 | 1 | 49.09090909 | 1 | 47.5 | 1.5 | 50 | 1.5 | 47.5 | 1.5 | 20 | 1 | 52.5 | 1.75 | 12.5 | 0.5 | 47.5 |
| 96 | 1 | MMBVSSSSMMKPR/BEMH/3166/01 | 25 | 1.5 | 49.09090909 | 1.75 | 32.5 | 1.25 | 35 | 1 | 47.5 | 1.5 | 75 | 0.5 | 57.5 | 1.75 | 12.5 | 0.5 | 17.5 |
| 97 | 1 | MMBVSSSSMMKPR/RG25/2941/09 | 37.5 | 1.25 | 52.72727273 | 1.25 | 20 | 1.25 | 10 | 0.25 | 50 | 1.5 | 45 | 1.5 | 12.5 | 1.5 | 47.5 | 1.5 | 52.5 |
| 98 | 1 | MMBVSSSSMMKPR/SP1/1287/98 | 27.5 | 1.5 | 52.72727273 | 1.25 | 57.5 | 1.5 | 50 | 1.25 | 50 | 1.5 | 47.5 | 1.5 | 52.5 | 1.5 | 52.5 | 1.5 | 17.5 |
| 99 | 1 | MMBVSSSSMMKPR/SP2/00396/06 | 42.5 | 1.5 | 52.72727273 | 2 | 57.5 | 1.75 | 52.5 | 1.5 | 52.5 | 1.5 | 47.5 | 1.75 | 57.5 | 1.75 | 42.5 | 1.25 | 52.5 |

TABLE 3C-continued

| Sl. No | Outcome | Sample No. | U%-M | UI-M | U%-C | UI-C | V%-M | VI-M | V%-C | VI-C | W%-M | WI-M | W%-C | WI-C | ZA1%-M | ZA1I-M | ZA1%-C | ZA1I-C | ZB%-C |
|---|---|---|---|---|---|---|---|---|---|---|---|---|---|---|---|---|---|---|---|
| 99 | 1 | MMBYSSSMMKPR/SP2/5090/03 | 22.5 | 1 | 52.72727273 | 1.5 | 45 | 1.75 | 52.5 | 1.5 | 22.5 | 1.5 | 47.5 | 1.75 | 42.5 | 1.75 | 42.5 | 1.5 | 52.5 |
| 100 | 1 | MMBYSSSMMKPR/SP3/00076/06 | 42.5 | 1.25 | 52.72727273 | 1.75 | 55 | 1.5 | 45 | 1.25 | 55 | 1.75 | 45 | 1.5 | 42.5 | 1.5 | 52.5 | 1.75 | 55 |
| 101 | 1 | MMBYSSSMMKPR/SP5/5658/09 | 12.5 | 0.5 | 54.54545455 | 1.75 | 40 | 1.5 | 50 | 1.5 | 42.5 | 1.5 | 50 | 1.75 | 45 | 1.5 | 42.5 | 1.5 | 52.5 |
| 102 | 1 | MMBYSSSMMKPR/SP9/1431/07 | 32.5 | 1.25 | 49.09090909 | 1.5 | 27.5 | 1.75 | 50 | 1.5 | 35 | 1.5 | 45 | 1.75 | 37.5 | 1.5 | 37.5 | 1 | 47.5 |
| 103 | 1 | MMBYSSSMMKPR/SP9/00521/07 | 37.5 | 1.25 | 49.09090909 | 1.75 | 50 | 1.5 | 45 | 1.5 | 50 | 1.5 | 45 | 1.75 | 52.5 | 1.75 | 25 | 1.5 | 52.5 |
| 104 | 1 | MMBYSSSMMKPR/SP9/919/99 | 42.5 | 1.25 | 52.72727273 | 1.75 | 15 | 0.5 | 10 | 0.25 | 17.5 | 1.75 | 47.5 | 1.75 | 52.5 | 1.25 | 52.5 | 1.5 | 52.5 |
| 105 | 1 | MMBYSSSMMKPR/SP10/1693/03 | 47.5 | 1.25 | 49.09090909 | 1.25 | 55 | 1.75 | 50 | 1.5 | 52.5 | 1.5 | 47.5 | 1.75 | 52.5 | 1.75 | 47.5 | 1.25 | 45 |
| 106 | 1 | MMBYSSSMMKPR/SP11/2802/01 | 52.5 | 1.5 | 50.90909091 | 1.75 | 52.5 | 1.5 | 42.5 | 1.25 | 52.5 | 1.5 | 45 | 1.75 | 52.5 | 1.5 | 40 | 1.5 | 45 |
| 107 | 1 | MMBYSSSMMKPR/SP11/1002/05 | 47.5 | 1.5 | 45.45454545 | 1.5 | 45 | 1.5 | 37.5 | 1.25 | 45 | 1.5 | 45 | 1.5 | 57.5 | 1.5 | 42.5 | 1.5 | 50 |
| 108 | 1 | MMBYSSSMMKPR/SP11/4945/09 | 42.5 | 1.25 | 49.09090909 | 1.5 | 50 | 1.5 | 45 | 1.5 | 47.5 | 1.5 | 42.5 | 1.75 | 50 | 1.5 | 42.5 | 1.5 | 37.5 |
| 109 | 1 | MMBYSSSMMKPR/RG32/47/10 | 42.5 | 1.25 | 50.90909091 | 1.5 | 52.5 | 1.75 | 45 | 1.25 | 37.5 | 1 | 35 | 1.75 | 52.5 | 1.5 | 45 | 1.5 | 37.5 |
| 110 | 1 | MMBYSSSMMKPR/RG32/7449/09 | 50 | 1.5 | 40 | 1.5 | 52.5 | 1.75 | 22.5 | 1 | 40 | 1.5 | 35 | 1.5 | 57.5 | 1.5 | 45 | 1.25 | 47.5 |
| 111 | 1 | MMBYSSSMMKPR/SP12/0353/09 | 50 | 1.25 | 52.72727273 | 1.5 | 55 | 1.5 | 50 | 1.25 | 52.5 | 1.5 | 32.5 | 1.5 | 42.5 | 1.5 | 20 | 1.25 | 12.5 |
| 112 | 1 | MMBYSSSMMKPR/SP12/2027/09 | 47.5 | 1.25 | 52.72727273 | 1.75 | 45 | 1.5 | 45 | 1.25 | 50 | 1.5 | 45 | 1.75 | 42.5 | 1.25 | 42.5 | 1.25 | 47.5 |
| 113 | 1 | MMBYSSSMMKPR/SP12/1631/09 | 47.5 | 1.25 | 52.72727273 | 1.75 | 60 | 1.5 | 55 | 1.75 | 57.5 | 1.5 | 52.5 | 1.75 | 57.5 | 1.5 | 37.5 | 1.75 | 37.5 |
| 114 | 1 | MMBYSSSMMKPR/RG34/1091/10 | 42.5 | 1.25 | 45.45454545 | 1.75 | 40 | 1.25 | 40 | 1.25 | 50 | 1.5 | 52.5 | 1.5 | 47.5 | 1.5 | 47.5 | 1.5 | 50 |
| 115 | 1 | MMBYSSSMMKPR/SP13/6097/08 | 42.5 | 1.25 | 52.72727273 | 1.5 | 55 | 1.5 | 50 | 1.5 | 52.5 | 1.5 | 45 | 1.5 | 52.5 | 1.25 | 52.5 | 1.5 | 50 |
| 116 | 1 | MMBYSSSMMKPR/BFMH/2540/04 | 17.5 | 1.25 | 32.72727273 | 2 | 27.5 | 2 | 10 | 0.25 | 37.5 | 1.5 | 7.5 | 0.5 | 55 | 2 | 42.5 | 1.25 | 27.5 |
| 117 | 1 | MMBYSSSMMKPR/BGMH/3558/03 | 12.5 | 0.5 | 56.36363636 | 2 | 62.5 | 2 | 27.5 | 1.25 | 60 | 2 | 20 | 1.5 | 42.5 | 1.75 | 27.5 | 1.25 | 47.5 |
| 118 | 1 | MMBYSSSMMKPR/BIMH/4596/05 | 37.5 | 1.5 | 34.54545455 | 1.5 | 57.5 | 1.75 | 10 | 0.25 | 57.5 | 1.75 | 7.5 | 0.5 | 47.5 | 1.75 | 37.5 | 1.75 | 32.5 |
| 119 | 1 | MMBYSSSMMKPR/BJMH/1942/07 | 20 | 1.5 | 41.81818182 | 1.25 | 50 | 1.5 | 10 | 0.25 | 52.5 | 1.5 | 7.5 | 0.5 | 52.5 | 2 | 37.5 | 0.5 | 42.5 |
| 120 | 1 | MMBYSSSMMKPR/BKMH/3435/06 | 47.5 | 2 | 56.36363636 | 2 | 40 | 1.5 | 50 | 1.75 | 57.5 | 1.5 | 47.5 | 2 | 32.5 | 1 | 12.5 | 1.5 | 42.5 |
| 121 | 1 | MMBYSSSMMKPR/BLJH/2584/05 | 37.5 | 1.5 | 56.36363636 | 1.5 | 60 | 2 | 35 | 1.75 | 50 | 2 | 20 | 1.25 | 12.5 | 0.5 | 37.5 | 0.5 | 42.5 |
| 122 | 1 | MMBYSSSMMKPR/BMMH/3591/08 | 37.5 | 1.75 | 50.90909091 | 2 | 60 | 2 | 10 | 0.25 | 60 | 2 | 15 | 0.5 | 50 | 1.5 | 12.5 | 1.5 | 40 |
| 123 | 1 | MMBYSSSMMKPR/BNMH/3242/06 | 42.5 | 1.75 | 50.90909091 | 1.5 | 60 | 2 | 25 | 1.75 | 60 | 2 | 15 | 1.75 | 52.5 | 1.75 | 50 | 1.5 | 42.5 |
| 124 | 1 | MMBYSSSMMKPR/BORG/0945/03 | 30 | 1.25 | 49.09090909 | 2 | 45 | 1 | 10 | 0.25 | 47.5 | 1.25 | 42.5 | 1.5 | 47.5 | 1.25 | 52.5 | 1.75 | 52.5 |
| 125 | 1 | MMBYSSSMMKPR/BPRG/3398/03 | 37.5 | 1.25 | 52.72727273 | 1.25 | 20 | 1 | 10 | 0.25 | 25 | 1 | 37.5 | 1.25 | 25 | 1 | 47.5 | 1.75 | 47.5 |
| 126 | 1 | MMBYSSSMMKPR/BQRG/4390/03 | 42.5 | 1.5 | 52.72727273 | 1.5 | 30 | 1.25 | 25 | 0.25 | 37.5 | 1.25 | 22.5 | 1.25 | 42.5 | 1.25 | 27.5 | 1.25 | 50 |
| 127 | 1 | MMBYSSSMMKPR/BTRG/3606/03 | 35 | 1.5 | 52.72727273 | 1.5 | 30 | 1 | 25 | 0.75 | 40 | 1.5 | 27.5 | 1.5 | 32.5 | 1.25 | 42.5 | 1.75 | 57.5 |
| 128 | 1 | MMBYSSSMMKPR/BUMH/6186/04 | 42.5 | 1.25 | 41.81818182 | 1.5 | 15 | 0.5 | 25 | 0.75 | 32.5 | 1.5 | 27.5 | 1.75 | 42.5 | 2 | 25 | 1.25 | 25 |
| 129 | 1 | MMBYSSSMMKPR/BVMH/6080/07 | 25 | 1.25 | 49.09090909 | 1.5 | 40 | 1 | 40 | 1.5 | 32.5 | 1.5 | 47.5 | 1.75 | 57.5 | 0.5 | 12.5 | 0.5 | 52.5 |
| 130 | 1 | MMBYSSSMMKPR/DMMX/3990/07 | 20 | 1 | 52.72727273 | 1.25 | 60 | 2 | 20 | 1.75 | 60 | 2 | 15 | 1.75 | 52.5 | 1.5 | 12.5 | 1.5 | 47.5 |
| 131 | 1 | MMBYSSSMMKPR/SP1/2238/01 | 27.5 | 1.25 | 52.72727273 | 1.5 | 15 | 0.5 | 10 | 0.25 | 20 | 1.25 | 37.5 | 1.75 | 25 | 1.25 | 50 | 1.5 | 47.5 |
| 132 | 1 | MMBYSSSMMKPR/RG15/1464/08 | 25 | 1 | 49.09090909 | 1.5 | 50 | 1.5 | 45 | 1.75 | 47.5 | 1.5 | 17.5 | 1 | 47.5 | 1.75 | 27.5 | 1.75 | 42.5 |
| 133 | 1 | MMBYSSSMMKPR/RG22/1931/09 | 22.5 | 1.25 | 52.72727273 | 1.5 | 27.5 | 1.5 | 45 | 1.5 | 27.5 | 1.25 | 42.5 | 1.75 | 17.5 | 1 | 42.5 | 1.5 | 42.5 |
| 134 | 1 | MMBYSSSMMKPR/MH14/6324/08 | 37.5 | 1 | 45.45454545 | 1.5 | 60 | 2 | 25 | 1 | 47.5 | 1.75 | 20 | 0.5 | 12.5 | 0.5 | 12.5 | 0.5 | 40 |
| 135 | 1 | MMBYSSSMMKPR/RG24/805/09 | 20 | 1 | 52.72727273 | 1.5 | 35 | 1 | 25 | 1.25 | 50 | 1.75 | 15 | 1.25 | 32.5 | 1 | 25 | 1.25 | 42.5 |
| 136 | 1 | MMBYSSSMMKPR/HCGA4/6374/08 | 52.5 | 1.5 | 52.72727273 | 1.5 | 55 | 1.5 | 50 | 1.5 | 50 | 1.5 | 42.5 | 1.25 | 37.5 | 1.25 | 25 | 1 | 52.5 |
| 137 | 1 | MMBYSSSMMKPR/SP1/3187/99 | 20 | 1.25 | 49.09090909 | 1.5 | 55 | 1.75 | 50 | 1.5 | 32.5 | 1.5 | 47.5 | 1.75 | 20 | 1.75 | 32.5 | 1 | 37.5 |
| 138 | 1 | MMBYSSSMMKPR/SP1/1543/00 | 32.5 | 1 | 52.72727273 | 1.5 | 45 | 1.5 | 25 | 0.75 | 25 | 1.5 | 45 | 1.75 | 52.5 | 1.75 | 45 | 1.5 | 52.5 |
| 139 | 1 | MMBYSSSMMKPR/SP2/10817/07 | 30 | 1 | 50.90909091 | 1.5 | 30 | 1.75 | 20 | 1 | 52.5 | 1.5 | 47.5 | 1.5 | 55 | 1.5 | 50 | 1.75 | 47.5 |
| 140 | 1 | MMBYSSSMMKPR/SP2/3424/03 | 22.5 | 1.25 | 52.72727273 | 1.5 | 57.5 | 1.5 | 45 | 1.25 | 50 | 1.5 | 47.5 | 1.75 | 42.5 | 1 | 55 | 1.5 | 42.5 |
| 141 | 1 | MMBYSSSMMKPR/SP2/489/02 | 12.5 | 0.5 | 47.27272727 | 1.5 | 50 | 1.5 | 42.5 | 1 | 42.5 | 1.25 | 42.5 | 1.5 | 30 | 1.25 | 32.5 | 1.75 | 37.5 |
| 142 | 1 | MMBYSSSMMKPR/SP3/5454/05 | 50 | 1.75 | 50.90909091 | 1.5 | 20 | 1.5 | 40 | 1 | 47.5 | 1.5 | 37.5 | 1.5 | 50 | 1.75 | 50 | 1.5 | 52.5 |
| 143 | 1 | MMBYSSSMMKPR/SP3/00070/06 | 25 | 1.5 | 50.90909091 | 1.5 | 37.5 | 1.25 | 42.5 | 1 | 27.5 | 1.5 | 45 | 1.5 | 47.5 | 1.5 | 12.5 | 1.75 | 50 |
| 144 | 1 | MMBYSSSMMKPR/SP4/11639/06 | 45 | 1.25 | 52.72727273 | 1.5 | 25 | 1.25 | 42.5 | 1 | 50 | 1.5 | 45 | 1.75 | 45 | 1.75 | 47.5 | 1.25 | 47.5 |
| 145 | 1 | MMBYSSSMMKPR/SP4/12823/07 | 17.5 | 1.25 | 52.72727273 | 1.5 | 35 | 1.5 | 35 | 1.25 | 27.5 | 1.25 | 42.5 | 1.5 | 42.5 | 1.5 | 42.5 | 1.5 | 37.5 |
| 146 | 1 | MMBYSSSMMKPR/SP4/14511/07 | 30 | 1.5 | 50.90909091 | 1.5 | 35 | 1.25 | 40 | 1.5 | 37.5 | 1.75 | 37.5 | 1.5 | 47.5 | 1.25 | 45 | 1.5 | 47.5 |
| 147 | 1 | MMBYSSSMMKPR/IIRG/4358/08 | 42.5 | 1.25 | 49.09090909 | 1.5 | 15 | 0.5 | 40 | 1 | 47.5 | 1.5 | 37.5 | 1.5 | 60 | 2 | 52.5 | 1.75 | 50 |
| 148 | 1 | MMBYSSSMMKPR/IVRG/1658/08 | 42.5 | 1.25 | 50.90909091 | 1.5 | 15 | 0.5 | 15 | 1.25 | 52.5 | 1.75 | 27.5 | 1.25 | 60 | 2 | 12.5 | 0.5 | 52.5 |

TABLE 3C-continued

| Sl. No | Outcome | Sample No. | U%-M | UI-M | U%-C | UI-C | V%-M | VI-M | V%-C | VI-C | W%-M | WI-M | W%-C | WI-C | ZA1%-M | ZA1I-M | ZA1%-C | ZA1I-C | ZB%-C |
|---|---|---|---|---|---|---|---|---|---|---|---|---|---|---|---|---|---|---|---|
| 149 | 1 | MMBVSSSSMMKPR/JRRG/6716/08 | 22.5 | 1 | 52.72727273 | 1.75 | 22.5 | 1.25 | 47.5 | 1.75 | 42.5 | 1.5 | 32.5 | 1.5 | 17.5 | 1.5 | 52.5 | 1.75 | 47.5 |
| 150 | 1 | MMBVSSSSMMKPR/JSMH/7129/07 | 25 | 1.25 | 50.90909091 | 1.5 | 47.5 | 1.75 | 37.5 | 1.5 | 52.5 | 1.75 | 32.5 | 1.5 | 52.5 | 2 | 45 | 1.5 | 37.5 |
| 151 | 0 | MMBVSSSSMMKPR/CPMH/1187/05 | 27.5 | 1.25 | 23.63636 | 0.5 | 55 | 1.5 | 45 | 1.5 | 57.5 | 2 | 7.5 | 0.5 | 52.5 | 2 | 12.5 | 0.5 | 37.5 |
| 152 | 0 | MMBVSSSSMMKPR/CSMH/3038/04 | 17.5 | 1.5 | 52.72727 | 1.5 | 32.5 | 1.75 | 45 | 1.5 | 50 | 1 | 7.5 | 0.5 | 52.5 | 1.75 | 47.5 | 1 | 42.5 |
| 153 | 0 | MMBVSSSSMMKPR/CTMH/2852/04 | 30 | 1.5 | 56.36364 | 1.75 | 42.5 | 1.75 | 45 | 1.5 | 60 | 2 | 20 | 1.75 | 12.5 | 1.75 | 12.5 | 0.5 | 22.5 |
| 154 | 0 | MMBVSSSSMMKPR/CUMH/1591/03 | 12.5 | 0.5 | 45.45455 | 1.5 | 47.5 | 1.75 | 47.5 | 1.5 | 52.5 | 1.5 | 7.5 | 0.5 | 52.5 | 0.5 | 22.5 | 1 | 37.5 |
| 155 | 0 | MMBVSSSSMMKPR/CWMH/3473/06 | 17.5 | 1.25 | 23.63636 | 0.5 | 55 | 1.5 | 50 | 1.25 | 60 | 2 | 7.5 | 0.5 | 52.5 | 2 | 32.5 | 2 | 42.5 |
| 156 | 0 | MMBVSSSSMMKPR/CXJH/3121/05 | 45 | 1.25 | 36.36364 | 1.25 | 40 | 1.5 | 10 | 0.25 | 32.5 | 2 | 7.5 | 0.5 | 52.5 | 1.5 | 12.5 | 0.5 | 32.5 |
| 157 | 0 | MMBVSSSSMMKPR/CYJH/0878/06 | 12.5 | 0.5 | 56.36364 | 2 | 55 | 2 | 10 | 0.25 | 52.5 | 1.75 | 7.5 | 0.5 | 12.5 | 0.5 | 12.5 | 0.5 | 52.5 |
| 158 | 0 | MMBVSSSSMMKPR/RG26/5002/09 | 52.5 | 1.25 | 52.72727 | 1.75 | 55 | 2 | 55 | 1.75 | 52.5 | 1.75 | 47.5 | 1.5 | 52.5 | 1.75 | 52.5 | 1.5 | 52.5 |
| 159 | 0 | MMBVSSSSMMKPR/DAMH/7095/09 | 50 | 1.5 | 47.27273 | 1.25 | 60 | 2 | 10 | 0.25 | 60 | 2 | 15 | 1.5 | 47.5 | 2 | 37.5 | 1.75 | 22.5 |
| 160 | 0 | MMBVSSSSMMKPR/DBMH/9616/08 | 32.5 | 1.25 | 50.90909 | 2 | 60 | 2 | 37.5 | 1.5 | 50 | 1.75 | 32.5 | 1.5 | 57.5 | 2 | 57.5 | 1.25 | 47.5 |

TABLE 3D

| Sl. No. | Outcome | Sample No. | ZC %-M | ZCI-M | ZC %-C |
|---|---|---|---|---|---|
| 1 | 1 | MMBVSSSMMKPR/AAJH/0467/06 | 33.33333333 | 0.666666667 | 76.36363636 |
| 2 | 1 | MMBVSSSMMKPR/ABMH/4734/07 | 33.33333333 | 0.666666667 | 87.27272727 |
| 3 | 1 | MMBVSSSMMKPR/HLRG/1219/03 | 33.33333333 | 0.666666667 | 32.72727273 |
| 4 | 1 | MMBVSSSMMKPR/ACRG/2834/03 | 40 | 1.166666667 | 65.45454545 |
| 5 | 1 | MMBVSSSMMKPR/AVRG/1397/04 | 33.33333333 | 0.666666667 | 87.27272727 |
| 6 | 1 | MMBVSSSMMKPR/AEMH/6521/06 | 50 | 1.333333333 | 0 |
| 7 | 1 | MMBVSSSMMKPR/AFJH/0478/06 | 33.33333333 | 0.666666667 | 76.36363636 |
| 8 | 1 | MMBVSSSMMKPR/HTMX/0675/08 | 33.33333333 | 0.666666667 | 76.36363636 |
| 9 | 1 | MMBVSSSMMKPR/IRRG/5724/08 | 46.66666667 | 1 | 87.27272727 |
| 10 | 1 | MMBVSSSMMKPR/JMRG/1480/08 | 45 | 1.166666667 | 98.18181818 |
| 11 | 1 | MMBVSSSMMKPR/HCGA1/222/10 | 33.33333333 | 0.666666667 | 76.36363636 |
| 12 | 1 | MMBVSSSMMKPR/KIDC/0164/06 | 43.33333333 | 1.166666667 | 76.36363636 |
| 13 | 1 | MMBVSSSMMKPR/KJDC/0167/06 | 40 | 1 | 76.36363636 |
| 14 | 1 | MMBVSSSMMKPR/KNDC/0176/05 | 50 | 1.166666667 | 76.36363636 |
| 15 | 1 | MMBVSSSMMKPR/MH11/3187/09 | 41.66666667 | 1.333333333 | 87.27272727 |
| 16 | 1 | MMBVSSSMMKPR/HCGA4/5535/06 | 33.33333333 | 0.666666667 | 87.27272727 |
| 17 | 1 | MMBVSSSMMKPR/SP5/6544/08 | 33.33333333 | 0.666666667 | 76.36363636 |
| 18 | 1 | MMBVSSSMMKPR/SP6/5298/06 | 53.33333333 | 1 | 76.36363636 |
| 19 | 1 | MMBVSSSMMKPR/SP6/6116/06 | 40 | 1 | 76.36363636 |
| 20 | 1 | MMBVSSSMMKPR/SP8/6543/06 | 56.66666667 | 1.333333333 | 87.27272727 |
| 21 | 1 | MMBVSSSMMKPR/SP9/1761/97 | 36.66666667 | 1 | 87.27272727 |
| 22 | 1 | MMBVSSSMMKPR/SP9/2006/02 | 38.33333333 | 1.166666667 | 81.81818182 |
| 23 | 1 | MMBVSSSMMKPR/SP10/4338/05 | 38.33333333 | 1.166666667 | 81.81818182 |
| 24 | 1 | MMBVSSSMMKPR/SP13/0242/10 | 45 | 1.166666667 | 87.27272727 |
| 25 | 1 | MMBVSSSMMKPR/ADRG/1440/02 | 40 | 1.166666667 | 54.54545455 |
| 26 | 1 | MMBVSSSMMKPR/AGMH/2268/04 | 33.33333333 | 0.666666667 | 65.45454545 |
| 27 | 1 | MMBVSSSMMKPR/AHMH/2180/03 | 33.33333333 | 0.666666667 | 43.63636364 |
| 28 | 1 | MMBVSSSMMKPR/AJMH/1975/03 | 33.33333333 | 0.666666667 | 87.27272727 |
| 29 | 1 | MMBVSSSMMKPR/AKMH/1186/03 | 33.33333333 | 0.666666667 | 87.27272727 |
| 30 | 1 | MMBVSSSMMKPR/ALMH/4227/05 | 45 | 1.166666667 | 65.45454545 |
| 31 | 1 | MMBVSSSMMKPR/AMMH/2138/05 | 41.66666667 | 1 | 87.27272727 |
| 32 | 1 | MMBVSSSMMKPR/ANMH/6528/05 | 33.33333333 | 0.666666667 | 87.27272727 |
| 33 | 1 | MMBVSSSMMKPR/AOMH/1621/05 | 33.33333333 | 0.666666667 | 54.54545455 |
| 34 | 1 | MMBVSSSMMKPR/APMH/6408/05 | 33.33333333 | 0.666666667 | 87.27272727 |
| 35 | 1 | MMBVSSSMMKPR/AQMH/1408/06 | 33.33333333 | 0.666666667 | 10.90909091 |
| 36 | 1 | MMBVSSSMMKPR/ARMH/4622/06 | 41.66666667 | 1 | 76.36363636 |
| 37 | 1 | MMBVSSSMMKPR/ASRG/5174/03 | 36.66666667 | 1 | 65.45454545 |
| 38 | 1 | MMBVSSSMMKPR/ATMH/4074/01 | 33.33333333 | 0.666666667 | 65.45454545 |
| 39 | 1 | MMBVSSSMMKPR/AYRG/3670/02 | 33.33333333 | 0.666666667 | 98.18181818 |
| 40 | 1 | MMBVSSSMMKPR/AZRG/1472/02 | 48.33333333 | 1.166666667 | 87.27272727 |
| 41 | 1 | MMBVSSSMMKPR/BAJH/0102/07 | 56.66666667 | 1.5 | 87.27272727 |
| 42 | 1 | MMBVSSSMMKPR/HSMH/4789/07 | 33.33333333 | 0.666666667 | 65.45454545 |
| 43 | 1 | MMBVSSSMMKPR/HKRG/3754/03 | 36.66666667 | 1 | 87.27272727 |
| 44 | 1 | MMBVSSSMMKPR/IMRG/5141/08 | 33.33333333 | 0.666666667 | 98.18181818 |
| 45 | 1 | MMBVSSSMMKPR/IQRG/5751/08 | 33.33333333 | 0.666666667 | 76.36363636 |
| 46 | 1 | MMBVSSSMMKPR/JNRG/6963/08 | 45 | 1.166666667 | 98.18181818 |
| 47 | 1 | MMBVSSSMMKPR/JORG/6520/08 | 46.66666667 | 1.5 | 87.27272727 |
| 48 | 1 | MMBVSSSMMKPR/IXRG/1912/08 | 43.33333333 | 1.166666667 | 76.36363636 |
| 49 | 1 | MMBVSSSMMKPR/IHRG/1461/07 | 33.33333333 | 0.666666667 | 87.27272727 |
| 50 | 1 | MMBVSSSMMKPR/INRG/6074/08 | 33.33333333 | 0.666666667 | 65.45454545 |
| 51 | 1 | MMBVSSSMMKPR/JPRG/7119/08 | 36.66666667 | 1 | 76.36363636 |
| 52 | 1 | MMBVSSSMMKPR/IARG/1209/01 | 33.33333333 | 0.666666667 | 76.36363636 |
| 53 | 1 | MMBVSSSMMKPR/JQRG/6998/08 | 46.66666667 | 1 | 92.72727273 |
| 54 | 1 | MMBVSSSMMKPR/HCGA1/5042/08 | 36.66666667 | 1 | 87.27272727 |
| 55 | 1 | MMBVSSSMMKPR/RG20/7272/08 | 38.33333333 | 1.166666667 | 87.27272727 |
| 56 | 1 | MMBVSSSMMKPR/MH10/826/06 | 36.66666667 | 1 | 87.27272727 |
| 57 | 1 | MMBVSSSMMKPR/MH12/6907/09 | 40 | 1.166666667 | 87.27272727 |
| 58 | 1 | MMBVSSSMMKPR/MH13/5276/09 | 33.33333333 | 0.666666667 | 87.27272727 |
| 59 | 1 | MMBVSSSMMKPR/MH13/2852/02 | 38.33333333 | 1.166666667 | 87.27272727 |
| 60 | 1 | MMBVSSSMMKPR/RG24/2672/09 | 43.33333333 | 1 | 76.36363636 |
| 61 | 1 | MMBVSSSMMKPR/RG24/786/09 | 53.33333333 | 1.166666667 | 65.45454545 |
| 62 | 1 | MMBVSSSMMKPR/RG24/3773/09 | 33.33333333 | 0.666666667 | 76.36363636 |
| 63 | 1 | MMBVSSSMMKPR/RG24/3821/09 | 43.33333333 | 1 | 76.36363636 |
| 64 | 1 | MMBVSSSMMKPR/RG25/1072/09 | 38.33333333 | 1.166666667 | 65.45454545 |
| 65 | 1 | MMBVSSSMMKPR/HCGA5/7545/07 | 55 | 1 | 87.27272727 |
| 66 | 1 | MMBVSSSMMKPR/SP2/2851/03 | 36.66666667 | 1.166666667 | 92.72727273 |
| 67 | 1 | MMBVSSSMMKPR/SP2/06011/08 | 36.66666667 | 1.166666667 | 92.72727273 |
| 68 | 1 | MMBVSSSMMKPR/SP2/5595E/04 | 33.33333333 | 0.666666667 | 81.81818182 |
| 69 | 1 | MMBVSSSMMKPR/SP3/12267/07 | 50 | 1.333333333 | 81.81818182 |
| 70 | 1 | MMBVSSSMMKPR/SP3/09935/08 | 58.33333333 | 1.333333333 | 87.27272727 |
| 71 | 1 | MMBVSSSMMKPR/SP4/04418/08 | 33.33333333 | 0.666666667 | 65.45454545 |
| 72 | 1 | MMBVSSSMMKPR/KFDC/0149/07 | 50 | 1.166666667 | 65.45454545 |
| 73 | 1 | MMBVSSSMMKPR/BDRG/5248/04 | 33.33333333 | 0.666666667 | 70.90909091 |
| 74 | 1 | MMBVSSSMMKPR/KODC/0178/05 | 33.33333333 | 0.666666667 | 76.36363636 |
| 75 | 1 | MMBVSSSMMKPR/SP5/2503/08 | 43.33333333 | 1.166666667 | 87.27272727 |
| 76 | 1 | MMBVSSSMMKPR/SP5/2049/09 | 53.33333333 | 1.166666667 | 76.36363636 |
| 77 | 1 | MMBVSSSMMKPR/SP5/2933/09 | 50 | 1 | 32.72727273 |
| 78 | 1 | MMBVSSSMMKPR/SP5/5414/09 | 43.33333333 | 1 | 76.36363636 |

TABLE 3D-continued

| | | | | | |
|---|---|---|---|---|---|
| 79 | 1 | MMBVSSSMMKPR/SP5/6317/09 | 33.33333333 | 0.666666667 | 81.81818182 |
| 80 | 1 | MMBVSSSMMKPR/SP5/5630/07 | 43.33333333 | 1.166666667 | 87.27272727 |
| 81 | 1 | MMBVSSSMMKPR/SP6/4628/02 | 45 | 1.166666667 | 81.81818182 |
| 82 | 1 | MMBVSSSMMKPR/SP6/215/05 | 41.66666667 | 1 | 87.27272727 |
| 83 | 1 | MMBVSSSMMKPR/SP6/4283/08 | 53.33333333 | 1 | 76.36363636 |
| 84 | 1 | MMBVSSSMMKPR/SP6/3004/09 | 50 | 1.166666667 | 65.45454545 |
| 85 | 1 | MMBVSSSMMKPR/SP7/6675/07 | 55 | 1.166666667 | 87.27272727 |
| 86 | 1 | MMBVSSSMMKPR/SP7/4924/06 | 33.33333333 | 0.666666667 | 87.27272727 |
| 87 | 1 | MMBVSSSMMKPR/SP8/7537/09 | 38.33333333 | 1.166666667 | 65.45454545 |
| 88 | 1 | MMBVSSSMMKPR/SP8/3347/09 | 53.33333333 | 1.333333333 | 87.27272727 |
| 89 | 1 | MMBVSSSMMKPR/SP8/7252/08 | 43.33333333 | 1.166666667 | 81.81818182 |
| 90 | 1 | MMBVSSSMMKPR/AURG/1691/04 | 43.33333333 | 1 | 76.36363636 |
| 91 | 1 | MMBVSSSMMKPR/AWRG/3418/04 | 36.66666667 | 1.166666667 | 87.27272727 |
| 92 | 1 | MMBVSSSMMKPR/HCGA1/6737/09 | 46.66666667 | 1.166666667 | 87.27272727 |
| 93 | 1 | MMBVSSSMMKPR/HCGA3/5860/09 | 36.66666667 | 1.166666667 | 92.72727273 |
| 94 | 1 | MMBVSSSMMKPR/BBMH/6814/07 | 33.33333333 | 0.666666667 | 43.63636364 |
| 95 | 1 | MMBVSSSMMKPR/BEMH/3166/01 | 53.33333333 | 1 | 76.36363636 |
| 96 | 1 | MMBVSSSMMKPR/RG25/2941/09 | 53.33333333 | 1.166666667 | 76.36363636 |
| 97 | 1 | MMBVSSSMMKPR/SP1/1287/98 | 45 | 1.333333333 | 87.27272727 |
| 98 | 1 | MMBVSSSMMKPR/SP2/00396/06 | 36.66666667 | 1.333333333 | 92.72727273 |
| 99 | 1 | MMBVSSSMMKPR/SP2/5090/03 | 36.66666667 | 1.166666667 | 76.36363636 |
| 100 | 1 | MMBVSSSMMKPR/SP3/00076/06 | 45 | 1.333333333 | 87.27272727 |
| 101 | 1 | MMBVSSSMMKPR/SP5/5658/09 | 46.66666667 | 1.166666667 | 87.27272727 |
| 102 | 1 | MMBVSSSMMKPR/SP9/1431/07 | 40 | 1.166666667 | 76.36363636 |
| 103 | 1 | MMBVSSSMMKPR/SP9/00521/07 | 40 | 1 | 76.36363636 |
| 104 | 1 | MMBVSSSMMKPR/SP9/919/99 | 41.66666667 | 1.166666667 | 87.27272727 |
| 105 | 1 | MMBVSSSMMKPR/SP10/1693/03 | 36.66666667 | 1 | 87.27272727 |
| 106 | 1 | MMBVSSSMMKPR/SP11/2802/01 | 56.66666667 | 1.166666667 | 87.27272727 |
| 107 | 1 | MMBVSSSMMKPR/SP11/1002/05 | 46.66666667 | 1.166666667 | 76.36363636 |
| 108 | 1 | MMBVSSSMMKPR/SP11/4945/09 | 51.66666667 | 1.166666667 | 87.27272727 |
| 109 | 1 | MMBVSSSMMKPR/RG32/47/10 | 46.66666667 | 1 | 87.27272727 |
| 110 | 1 | MMBVSSSMMKPR/RG32/7449/09 | 56.66666667 | 1.333333333 | 70.90909091 |
| 111 | 1 | MMBVSSSMMKPR/SP12/0353/09 | 53.33333333 | 1.166666667 | 76.36363636 |
| 112 | 1 | MMBVSSSMMKPR/SP12/2027/09 | 41.66666667 | 1.166666667 | 87.27272727 |
| 113 | 1 | MMBVSSSMMKPR/SP12/1631/09 | 40 | 1.166666667 | 87.27272727 |
| 114 | 1 | MMBVSSSMMKPR/RG34/1091/10 | 43.33333333 | 1.166666667 | 87.27272727 |
| 115 | 1 | MMBVSSSMMKPR/SP13/6097/08 | 41.66666667 | 1 | 87.27272727 |
| 116 | 1 | MMBVSSSMMKPR/BFMH/2540/04 | 33.33333333 | 0.666666667 | 87.27272727 |
| 117 | 1 | MMBVSSSMMKPR/BGMH/3558/03 | 33.33333333 | 0.666666667 | 87.27272727 |
| 118 | 1 | MMBVSSSMMKPR/BIMH/4596/05 | 50 | 1.166666667 | 43.63636364 |
| 119 | 1 | MMBVSSSMMKPR/BJMH/1942/07 | 33.33333333 | 0.666666667 | 54.54545455 |
| 120 | 1 | MMBVSSSMMKPR/BKMH/3435/06 | 43.33333333 | 1.166666667 | 87.27272727 |
| 121 | 1 | MMBVSSSMMKPR/BLJH/2584/05 | 33.33333333 | 0.666666667 | 65.45454545 |
| 122 | 1 | MMBVSSSMMKPR/BMMH/3591/08 | 33.33333333 | 0.666666667 | 81.81818182 |
| 123 | 1 | MMBVSSSMMKPR/BNMH/3242/06 | 33.33333333 | 0.666666667 | 87.27272727 |
| 124 | 1 | MMBVSSSMMKPR/BORG/0945/03 | 50 | 1.166666667 | 87.27272727 |
| 125 | 1 | MMBVSSSMMKPR/BPRG/3398/03 | 33.33333333 | 0.666666667 | 65.45454545 |
| 126 | 1 | MMBVSSSMMKPR/BQRG/4390/03 | 33.33333333 | 0.666666667 | 103.6363636 |
| 127 | 1 | MMBVSSSMMKPR/BTRG/3606/03 | 36.66666667 | 1.166666667 | 65.45454545 |
| 128 | 1 | MMBVSSSMMKPR/BUMH/6186/04 | 41.66666667 | 1.166666667 | 87.27272727 |
| 129 | 1 | MMBVSSSMMKPR/BVMH/6080/07 | 33.33333333 | 0.666666667 | 81.81818182 |
| 130 | 1 | MMBVSSSMMKPR/DMMX/3990/07 | 38.33333333 | 1 | 87.27272727 |
| 131 | 1 | MMBVSSSMMKPR/SP1/2238/01 | 36.66666667 | 1.166666667 | 87.27272727 |
| 132 | 1 | MMBVSSSMMKPR/RG15/1464/08 | 33.33333333 | 0.666666667 | 87.27272727 |
| 133 | 1 | MMBVSSSMMKPR/RG22/1931/09 | 38.33333333 | 1 | 87.27272727 |
| 134 | 1 | MMBVSSSMMKPR/MH14/6324/08 | 33.33333333 | 0.666666667 | 87.27272727 |
| 135 | 1 | MMBVSSSMMKPR/RG24/805/09 | 56.66666667 | 1.166666667 | 76.36363636 |
| 136 | 1 | MMBVSSSMMKPR/HCGA4/6374/08 | 41.66666667 | 1.166666667 | 87.27272727 |
| 137 | 1 | MMBVSSSMMKPR/SP1/3187/99 | 36.66666667 | 1 | 87.27272727 |
| 138 | 1 | MMBVSSSMMKPR/SP1/1543/00 | 46.66666667 | 1.166666667 | 87.27272727 |
| 139 | 1 | MMBVSSSMMKPR/SP2/10817/07 | 45 | 1.166666667 | 87.27272727 |
| 140 | 1 | MMBVSSSMMKPR/SP2/3424/03 | 43.33333333 | 1.166666667 | 81.81818182 |
| 141 | 1 | MMBVSSSMMKPR/SP2/489/02 | 33.33333333 | 0.666666667 | 54.54545455 |
| 142 | 1 | MMBVSSSMMKPR/SP3/5454/05 | 46.66666667 | 1.333333333 | 76.36363636 |
| 143 | 1 | MMBVSSSMMKPR/SP3/00070/06 | 33.33333333 | 0.666666667 | 87.27272727 |
| 144 | 1 | MMBVSSSMMKPR/SP4/11639/06 | 45 | 1.166666667 | 81.81818182 |
| 145 | 1 | MMBVSSSMMKPR/SP4/12823/07 | 36.66666667 | 1.166666667 | 81.81818182 |
| 146 | 1 | MMBVSSSMMKPR/SP4/14511/07 | 36.66666667 | 1.166666667 | 87.27272727 |
| 147 | 1 | MMBVSSSMMKPR/IIRG/4358/08 | 38.33333333 | 1.166666667 | 65.45454545 |
| 148 | 1 | MMBVSSSMMKPR/IVRG/1658/08 | 33.33333333 | 0.666666667 | 0 |
| 149 | 1 | MMBVSSSMMKPR/JRRG/6716/08 | 46.66666667 | 1 | 87.27272727 |
| 150 | 1 | MMBVSSSMMKPR/JSMH/7129/07 | 46.66666667 | 1 | 76.36363636 |
| 151 | 0 | MMBVSSSMMKPR/CPMH/1187/05 | 53.33333333 | 1.166666667 | 87.27272727 |
| 152 | 0 | MMBVSSSMMKPR/CSMH/3038/04 | 33.33333333 | 0.666666667 | 76.36363636 |
| 153 | 0 | MMBVSSSMMKPR/CTMH/2852/04 | 36.66666667 | 1.166666667 | 87.27272727 |
| 154 | 0 | MMBVSSSMMKPR/CUMH/1591/03 | 40 | 1 | 43.63636364 |
| 155 | 0 | MMBVSSSMMKPR/CWMH/3473/06 | 38.33333333 | 1 | 54.54545455 |
| 156 | 0 | MMBVSSSMMKPR/CXJH/3121/05 | 36.66666667 | 1 | 87.27272727 |
| 157 | 0 | MMBVSSSMMKPR/CYJH/0878/06 | 33.33333333 | 0.666666667 | 65.45454545 |
| 158 | 0 | MMBVSSSMMKPR/RG26/5002/09 | 40 | 1.333333333 | 87.27272727 |

TABLE 3D-continued

| | | | Sl. No. | ZCI-C | ZD %-C | ZDI-C | ZF2 %-N | ZF2I-N |
|---|---|---|---|---|---|---|---|---|
| 159 | 0 | MMBVSSSMMKPR/DAMH/7095/09 | | 46.66666667 | 1 | | 43.63636364 | |
| 160 | 0 | MMBVSSSMMKPR/DBMH/9616/08 | | 33.33333333 | 0.666666667 | | 87.27272727 | |
| | | | 1 | 2.5 | 83.91608392 | 3.333333333 | 74.59016393 | 2.666666667 |
| | | | 2 | 3.333333333 | 78.67132867 | 2.666666667 | 85.24590164 | 4 |
| | | | 3 | 2.5 | 83.91608392 | 2.666666667 | 63.93442623 | 4 |
| | | | 4 | 2.5 | 41.95804196 | 2 | 101.2295082 | 4 |
| | | | 5 | 3.333333333 | 83.91608392 | 4 | 26.63934426 | 2.666666667 |
| | | | 6 | 0.833333333 | 73.42657343 | 2.666666667 | 74.59016393 | 4 |
| | | | 7 | 2.5 | 94.40559441 | 4 | 0 | 0 |
| | | | 8 | 2.5 | 57.69230769 | 2.666666667 | 85.24590164 | 2.666666667 |
| | | | 9 | 3.333333333 | 52.44755245 | 3.333333333 | 10.6557377 | 2.666666667 |
| | | | 10 | 3.333333333 | 73.42657343 | 3.333333333 | 63.93442623 | 2.666666667 |
| | | | 11 | 2.5 | 62.93706294 | 2 | 10.6557377 | 2 |
| | | | 12 | 2.5 | 52.44755245 | 2 | 26.63934426 | 3.333333333 |
| | | | 13 | 2.916666667 | 73.42657343 | 2 | 10.6557377 | 2 |
| | | | 14 | 2.916666667 | 52.44755245 | 2.666666667 | 10.6557377 | 2.666666667 |
| | | | 15 | 3.333333333 | 73.42657343 | 2 | 21.31147541 | 2 |
| | | | 16 | 2.916666667 | 83.91608392 | 3.333333333 | 0 | 0 |
| | | | 17 | 2.5 | 73.42657343 | 2.666666667 | 26.63934426 | 2.666666667 |
| | | | 18 | 2.083333333 | 73.42657343 | 3.333333333 | 21.31147541 | 2 |
| | | | 19 | 2.5 | 83.91608392 | 3.333333333 | 79.91803279 | 3.333333333 |
| | | | 20 | 2.5 | 83.91608392 | 2.666666667 | 21.31147541 | 2 |
| | | | 21 | 2.916666667 | 78.67132867 | 3.333333333 | 0 | 0 |
| | | | 22 | 2.916666667 | 83.91608392 | 3.333333333 | 10.6557377 | 2.666666667 |
| | | | 23 | 2.916666667 | 83.91608392 | 3.333333333 | 5.327868852 | 2.666666667 |
| | | | 24 | 2.916666667 | 83.91608392 | 2.666666667 | 63.93442623 | 4 |
| | | | 25 | 2.5 | 52.44755245 | 2.666666667 | 95.90163934 | 3.333333333 |
| | | | 26 | 2.916666667 | 20.97902098 | 1.333333333 | 10.6557377 | 2.666666667 |
| | | | 27 | 3.333333333 | 83.91608392 | 2.666666667 | 31.96721311 | 3.333333333 |
| | | | 28 | 3.333333333 | 94.40559441 | 4 | 21.31147541 | 2.666666667 |
| | | | 29 | 3.333333333 | 94.40559441 | 4 | 15.98360656 | 2.666666667 |
| | | | 30 | 3.333333333 | 62.93706294 | 1.333333333 | 0 | 0 |
| | | | 31 | 2.916666667 | 73.42657343 | 4 | 74.59016393 | 2.666666667 |
| | | | 32 | 3.333333333 | 83.91608392 | 4 | 31.96721311 | 2.666666667 |
| | | | 33 | 2.916666667 | 73.42657343 | 3.333333333 | 0 | 0 |
| | | | 34 | 3.333333333 | 73.42657343 | 3.333333333 | 15.98360656 | 2.666666667 |
| | | | 35 | 1.666666667 | 83.91608392 | 3.333333333 | 74.59016393 | 2.666666667 |
| | | | 36 | 2.916666667 | 83.91608392 | 4 | 79.91803279 | 2.666666667 |
| | | | 37 | 2.5 | 78.67132867 | 4 | 26.63934426 | 2.666666667 |
| | | | 38 | 3.333333333 | 62.93706294 | 2.666666667 | 85.24590164 | 4 |
| | | | 39 | 3.333333333 | 73.42657343 | 2.666666667 | 0 | 0 |
| | | | 40 | 2.916666667 | 73.42657343 | 3.333333333 | 0 | 0 |
| | | | 41 | 2.916666667 | 83.91608392 | 4 | 79.91803279 | 3.333333333 |
| | | | 42 | 2.083333333 | 73.42657343 | 4 | 95.90163934 | 3.333333333 |
| | | | 43 | 2.5 | 68.18181818 | 2.666666667 | 15.98360656 | 1.333333333 |
| | | | 44 | 3.333333333 | 104.8951049 | 4 | 31.96721311 | 2.666666667 |
| | | | 45 | 2.5 | 83.91608392 | 2.666666667 | 74.59016393 | 4 |
| | | | 46 | 3.333333333 | 94.40559441 | 1.333333333 | 53.27868852 | 2 |
| | | | 47 | 3.333333333 | 94.40559441 | 4 | 31.96721311 | 2.666666667 |
| | | | 48 | 3.333333333 | 94.40559441 | 4 | 0 | 0 |
| | | | 49 | 2.916666667 | 83.91608392 | 4 | 10.6557377 | 1.333333333 |
| | | | 50 | 2.916666667 | 73.42657343 | 4 | 21.31147541 | 1.333333333 |
| | | | 51 | 2.5 | 83.91608392 | 3.333333333 | 31.96721311 | 1.333333333 |
| | | | 52 | 2.5 | 78.67132867 | 3.333333333 | 95.90163934 | 3.333333333 |
| | | | 53 | 3.333333333 | 78.67132867 | 2.666666667 | 58.60655738 | 3.333333333 |
| | | | 54 | 2.5 | 83.91608392 | 3.333333333 | 10.6557377 | 2 |
| | | | 55 | 2.5 | 83.91608392 | 2.666666667 | 0 | 0 |
| | | | 56 | 2.916666667 | 41.95804196 | 2 | 69.26229508 | 3.333333333 |
| | | | 57 | 2.916666667 | 73.42657343 | 3.333333333 | 15.98360656 | 2 |
| | | | 58 | 2.916666667 | 83.91608392 | 2.666666667 | 0 | 0 |
| | | | 59 | 2.083333333 | 83.91608392 | 2 | 95.90163934 | 3.333333333 |
| | | | 60 | 1.666666667 | 68.18181818 | 2.666666667 | 0 | 0 |
| | | | 61 | 2.083333333 | 62.93706294 | 2.666666667 | 0 | 0 |
| | | | 62 | 2.5 | 83.91608392 | 2 | 79.91803279 | 3.333333333 |
| | | | 63 | 1.666666667 | 52.44755245 | 2 | 10.6557377 | 3.333333333 |
| | | | 64 | 2.083333333 | 83.91608392 | 2.666666667 | 0 | 0 |
| | | | 65 | 2.916666667 | 83.91608392 | 3.333333333 | 74.59016393 | 3.333333333 |
| | | | 66 | 2.916666667 | 83.91608392 | 3.333333333 | 0 | 0 |
| | | | 67 | 2.916666667 | 83.91608392 | 3.333333333 | 0 | 0 |
| | | | 68 | 2.5 | 83.91608392 | 3.333333333 | 31.96721311 | 3.333333333 |
| | | | 69 | 2.916666667 | 78.67132867 | 2.666666667 | 53.27868852 | 2.666666667 |
| | | | 70 | 2.916666667 | 73.42657343 | 2.666666667 | 0 | 0 |
| | | | 71 | 2.5 | 89.16083916 | 3.333333333 | 0 | 0 |
| | | | 72 | 2.916666667 | 52.44755245 | 2 | 42.62295082 | 2.666666667 |
| | | | 73 | 2.916666667 | 78.67132867 | 3.333333333 | 0 | 0 |
| | | | 74 | 2.5 | 41.9580416 | 2.666666667 | 74.59016393 | 2.666666667 |
| | | | 75 | 2.5 | 83.91608392 | 2 | 0 | 0 |

TABLE 3D-continued

| | | | | | |
|---|---|---|---|---|---|
| 76 | 2.5 | 73.42657343 | 2.666666667 | 0 | 0 |
| 77 | 2.083333333 | 52.44755245 | 2 | 21.31147541 | 2.666666667 |
| 78 | 2.083333333 | 73.42657343 | 2.666666667 | 42.62295082 | 2.666666667 |
| 79 | 2.083333333 | 83.91608392 | 3.333333333 | 69.26229508 | 2.666666667 |
| 80 | 2.5 | 73.42657343 | 2.666666667 | 90.57377049 | 4 |
| 81 | 2.5 | 83.91608392 | 3.333333333 | 37.29508197 | 2.666666667 |
| 82 | 2.5 | 83.91608392 | 3.333333333 | 0 | 0 |
| 83 | 2.083333333 | 83.91608392 | 3.333333333 | 85.24590164 | 3.333333333 |
| 84 | 2.5 | 68.18181818 | 3.333333333 | 26.63934426 | 1.333333333 |
| 85 | 2.5 | 83.91608392 | 2.666666667 | 31.96721311 | 2 |
| 86 | 2.916666667 | 83.91608392 | 3.333333333 | 0 | 0 |
| 87 | 2.5 | 68.18181818 | 2.666666667 | 31.96721311 | 3.333333333 |
| 88 | 2.916666667 | 73.42657343 | 3.333333333 | 95.90163934 | 3.333333333 |
| 89 | 2.916666667 | 78.67132867 | 2.666666667 | 63.93442623 | 2.666666667 |
| 90 | 2.916666667 | 73.42657343 | 3.333333333 | 53.27868852 | 2.666666667 |
| 91 | 2.916666667 | 73.42657343 | 2.666666667 | 0 | 0 |
| 92 | 2.5 | 83.91608392 | 2 | 0 | 0 |
| 93 | 2.5 | 73.42657343 | 3.333333333 | 63.93442623 | 4 |
| 94 | 1.666666667 | 73.42657343 | 2 | 21.31147541 | 3.333333333 |
| 95 | 2.083333333 | 15.73426573 | 2 | 85.24590164 | 4 |
| 96 | 2.5 | 83.91608392 | 3.333333333 | 95.90163934 | 4 |
| 97 | 2.916666667 | 68.18181818 | 3.333333333 | 53.27868852 | 3.333333333 |
| 98 | 2.916666667 | 83.91608392 | 3.333333333 | 42.62295082 | 4 |
| 99 | 2.5 | 83.91608392 | 3.333333333 | 53.27868852 | 2.666666667 |
| 100 | 2.916666667 | 83.91608392 | 3.333333333 | 0 | 0 |
| 101 | 2.916666667 | 68.18181818 | 2.666666667 | 15.98360656 | 2.666666667 |
| 102 | 2.5 | 83.91608392 | 3.333333333 | 0 | 0 |
| 103 | 2.5 | 83.91608392 | 3.333333333 | 42.62295082 | 2.666666667 |
| 104 | 2.916666667 | 83.91608392 | 3.333333333 | 85.24590164 | 2.666666667 |
| 105 | 2.5 | 83.91608392 | 2.666666667 | 85.24590164 | 3.333333333 |
| 106 | 2.5 | 83.91608392 | 3.333333333 | 95.90163934 | 3.333333333 |
| 107 | 2.5 | 73.42657343 | 3.333333333 | 95.90163934 | 3.333333333 |
| 108 | 2.916666667 | 83.91608392 | 3.333333333 | 74.59016393 | 2 |
| 109 | 2.5 | 68.18181818 | 2.666666667 | 0 | 0 |
| 110 | 2.916666667 | 62.93706294 | 2 | 5.327868852 | 4 |
| 111 | 2.916666667 | 10.48951049 | 1.333333333 | 79.91803279 | 2.666666667 |
| 112 | 2.916666667 | 83.91608392 | 2.666666667 | 0 | 0 |
| 113 | 2.916666667 | 78.67132867 | 1.333333333 | 95.90163934 | 2.666666667 |
| 114 | 2.916666667 | 83.91608392 | 3.333333333 | 63.93442623 | 4 |
| 115 | 2.916666667 | 83.91608392 | 3.333333333 | 74.59016393 | 2.666666667 |
| 116 | 2.083333333 | 62.93706294 | 2.666666667 | 85.24590164 | 2.666666667 |
| 117 | 3.333333333 | 31.46853147 | 2 | 85.24590164 | 2.666666667 |
| 118 | 2.916666667 | 52.44755245 | 2.666666667 | 37.29508197 | 2 |
| 119 | 2.5 | 73.42657343 | 3.333333333 | 63.93442623 | 3.333333333 |
| 120 | 3.333333333 | 89.16083916 | 4 | 42.62295082 | 2.666666667 |
| 121 | 2.5 | 83.91608392 | 4 | 0 | 0 |
| 122 | 3.333333333 | 62.93706294 | 2.666666667 | 95.90163934 | 3.333333333 |
| 123 | 2.5 | 83.91608392 | 4 | 31.96721311 | 2 |
| 124 | 2.916666667 | 83.91608392 | 3.333333333 | 26.63934426 | 1.333333333 |
| 125 | 2.916666667 | 78.67132867 | 3.333333333 | 10.6557377 | 2.666666667 |
| 126 | 3.333333333 | 73.42657343 | 2.666666667 | 37.29508197 | 2 |
| 127 | 2.5 | 73.42657343 | 2 | 10.6557377 | 1.333333333 |
| 128 | 2.916666667 | 0 | 0 | 0 | 0 |
| 129 | 2.5 | 52.44755245 | 2 | 53.27868852 | 2.666666667 |
| 130 | 2.916666667 | 62.93706294 | 2.666666667 | 31.96721311 | 2.666666667 |
| 131 | 2.916666667 | 41.95804196 | 2.666666667 | 0 | 0 |
| 132 | 2.5 | 83.91608392 | 2.666666667 | 42.62295082 | 1.333333333 |
| 133 | 2.5 | 83.91608392 | 2.666666667 | 0 | 0 |
| 134 | 2.916666667 | 73.42657343 | 2.666666667 | 85.24590164 | 2 |
| 135 | 2.5 | 73.42657343 | 2.666666667 | 0 | 0 |
| 136 | 2.5 | 83.91608392 | 3.333333333 | 0 | 0 |
| 137 | 2.916666667 | 73.42657343 | 2.666666667 | 79.91803279 | 4 |
| 138 | 2.5 | 62.93706294 | 3.333333333 | 42.62295082 | 2.666666667 |
| 139 | 2.916666667 | 83.91608392 | 3.333333333 | 63.93442623 | 2.666666667 |
| 140 | 2.5 | 83.91608392 | 3.333333333 | 0 | 0 |
| 141 | 2.083333333 | 83.91608392 | 3.333333333 | 85.24590164 | 3.333333333 |
| 142 | 2.5 | 78.67132867 | 3.333333333 | 0 | 0 |
| 143 | 2.5 | 83.91608392 | 3.333333333 | 0 | 0 |
| 144 | 2.083333333 | 78.67132867 | 3.333333333 | 21.31147541 | 2 |
| 145 | 2.916666667 | 83.91608392 | 3.333333333 | 15.98360656 | 2 |
| 146 | 2.916666667 | 89.16083916 | 3.333333333 | 0 | 0 |
| 147 | 2.916666667 | 73.42657343 | 4 | 0 | 0 |
| 148 | 0.833333333 | 89.16083916 | 4 | 85.24590164 | 4 |
| 149 | 3.333333333 | 78.67132867 | 3.333333333 | 0 | 0 |
| 150 | 2.5 | 83.91608392 | 3.333333333 | 0 | 0 |
| 151 | 2.916666667 | 78.67132867 | 2.666666667 | 95.90163934 | 4 |
| 152 | 2.916666667 | 36.71328671 | 2 | 74.59016393 | 4 |
| 153 | 2.916666667 | 68.18181818 | 4 | 95.90163934 | 3.333333333 |
| 154 | 2.5 | 83.91608392 | 4 | 0 | 0 |
| 155 | 2.083333333 | 36.71328671 | 2.666666667 | 26.63934426 | 2.666666667 |

TABLE 3D-continued

| | | | | | |
|---|---|---|---|---|---|
| 156 | 2.916666667 | 73.42657343 | 2.666666667 | 95.90163934 | 3.333333333 |
| 157 | 2.5 | 73.42657343 | 3.333333333 | 0 | 0 |
| 158 | 2.916666667 | 73.42657343 | 3.333333333 | 42.62295082 | 2.666666667 |
| 159 | 1.666666667 | 10.48951049 | 1.333333333 | 63.93442623 | 4 |
| 160 | 2.5 | 73.42657343 | 2.666666667 | 74.59016393 | 2.666666667 |

Once the combination of 5 biomarkers is selected, based on the data obtained by retrospective study of 298 patient samples (training set), scores of these 5 biomarkers are coupled with the three clinical parameters (tumor size, grade and node status) to construct/develop the CanAssist-Breast algorithm/algorithm of the present disclosure which provides a CanAssist Breast relapse score which helps in stratifying patients as low risk or high risk of recurrence within 5 years from diagnosis. The relapse score is computed on a scale of 1-100 and scores of 15.5 and below are classified as low risk, and above 15.5 are classified as high risk. The risk of recurrence is considered high if the probability of recurrence is greater than about 9% and low if it is less than or equal to about 9%.

Example 2: Validation Studies of 5 Biomarker and 3 Clinical Parameter Combination of the Present Disclosure and Correlation of CanAssist Breast Relapse Score with Recurrence in Early Stage ER-14PR+ and Her2− Breast Cancer Patients The prognostic test developed in example 1 is validated on a validation sample set of 700 early stage ER+/PR+ and Her2− breast cancer patients. A representative set of the complete validation set is provided herewith by way of table no. 4, wherein IHC measurements are provided for 299 data samples.

TABLE 4

| Sl. No | Age | Grade | TNM | A %-M | W %-C | U %-C | R %-M | F %-M |
|---|---|---|---|---|---|---|---|---|
| 1 | 53 | 1 | T1N0M0 | 37.5 | 22.5 | 38.2 | 48 | 32.86 |
| 2 | 66 | 2 | T1N0M0 | 57.5 | 45 | 50.9 | 48 | 34.29 |
| 3 | 72 | 2 | T2N0M0 | 50 | 47.5 | 52.7 | 44 | 35.71 |
| 4 | 42 | 2 | T2N0M0 | 52.5 | 47.5 | 52.7 | 42 | 32.86 |
| 5 | 43 | 3 | T1N0M0 | 52.5 | 42.5 | 50.9 | 40 | 27.14 |
| 6 | 69 | 3 | T2N0M0 | 15 | 40 | 38.2 | 34 | 21.43 |
| 7 | 40 | 3 | T2N0M0 | 42.5 | 37.5 | 49.1 | 44 | 27.14 |
| 8 | 52 | 2 | T2N1M0 | 17.5 | 42.5 | 49.1 | 44 | 30.00 |
| 9 | 44 | 2 | T2N0M0 | 52.5 | 48.75 | 51.8 | 31 | 20.71 |
| 10 | 62 | 1 | T2N0M0 | 52.5 | 50 | 52.7 | 38 | 20.71 |
| 11 | 62 | 2 | T1N0M0 | 28.75 | 43.75 | 49.1 | 35 | 22.14 |
| 12 | 61 | 1 | T1N0M0 | 27.5 | 43.75 | 49.1 | 50 | 32.86 |
| 13 | 41 | 2 | T2N0M0 | 15 | 45 | 52.7 | 29 | 12.86 |
| 14 | 59 | 2 | T1N0M0 | 50 | 46.25 | 50.9 | 29 | 18.57 |
| 15 | 59 | 3 | T2N2M0 | 12.5 | 38.75 | 50.9 | 25 | 15.00 |
| 16 | 71 | 3 | T2N1M0 | 22.5 | 42.5 | 52.7 | 30 | 17.86 |
| 17 | 59 | 2 | T1N0M0 | 32.5 | 45 | 50.9 | 36 | 19.29 |
| 18 | 65 | 3 | T2N0M0 | 12.5 | 43.75 | 50.0 | 24 | 14.29 |
| 19 | 57 | 2 | T2N0M0 | 35 | 46.25 | 51.8 | 45 | 25.00 |
| 20 | 67 | 2 | T1N0M0 | 36.25 | 42.5 | 50.0 | 41 | 15.71 |
| 21 | 43 | 2 | T1N0M0 | 22.5 | 32.5 | 51.8 | 27 | 18.57 |
| 22 | 74 | 1 | T2N0M0 | 21.25 | 40 | 47.3 | 28 | 15.71 |
| 23 | 59 | 2 | T1N0M0 | 43.75 | 47.5 | 52.7 | 37 | 24.29 |
| 24 | 42 | 2 | T1N0M0 | 17.5 | 30 | 40.0 | 23 | 12.86 |
| 25 | 72 | 3 | T2N0M0 | 37.5 | 40 | 47.3 | 26 | 14.29 |
| 26 | 56 | 2 | T2N0M0 | 12.5 | 46.25 | 52.7 | 28 | 19.29 |
| 27 | 72 | 2 | T1N0M0 | 42.5 | 46.25 | 51.8 | 40 | 27.14 |
| 28 | 51 | 2 | T2N0M0 | 50 | 47.5 | 53.6 | 22 | 12.86 |
| 29 | 57 | 3 | T2N0M0 | 35 | 47.5 | 52.7 | 37 | 22.86 |
| 30 | 72 | 2 | T2N1M0 | 52.5 | 45 | 52.7 | 40 | 25.71 |
| 31 | 50 | 2 | T2N0M0 | 22.5 | 40 | 51.8 | 46 | 17.86 |
| 32 | 75 | 2 | T3N1M0 | 18.75 | 42.5 | 52.7 | 24 | 15.71 |
| 33 | 73 | 1 | T1N0M0 | 20 | 41.25 | 49.1 | 25 | 12.86 |
| 34 | 64 | 3 | T2N0M0 | 12.5 | 45 | 51.8 | 25 | 14.29 |
| 35 | 75 | 2 | T2N2M0 | 25 | 48.75 | 53.6 | 24 | 15.71 |
| 36 | 66 | 1 | T1N0M0 | 18.75 | 41.25 | 51.8 | 28 | 20.71 |
| 37 | 64 | 2 | T2N0M0 | 37.5 | 50 | 52.7 | 26 | 16.43 |
| 38 | 57 | 1 | T1N1M0 | 32.5 | 43.75 | 49.1 | 24 | 16.43 |
| 39 | 73 | 2 | T2N1M0 | 13.75 | 45 | 53.6 | 36 | 20.71 |
| 40 | 67 | 3 | T1N0M0 | 27.5 | 42.5 | 53.6 | 28 | 15.00 |
| 41 | 69 | 2 | T2N0M0 | 46.25 | 46.25 | 52.7 | 26 | 15.71 |
| 42 | 57 | 2 | T1N0M0 | 12.5 | 42.5 | 52.7 | 20 | 12.86 |
| 43 | 70 | 2 | T1N0M0 | 40 | 46.25 | 52.7 | 22 | 15.00 |
| 44 | 63 | 3 | T1N0M0 | 50 | 42.5 | 54.5 | 31 | 17.14 |
| 45 | 51 | 3 | T2N0M0 | 52.5 | 37.5 | 50.9 | 20 | 14.29 |
| 46 | 71 | 2 | T2N0M0 | 45 | 46.25 | 47.3 | 20 | 14.29 |
| 47 | 60 | 3 | T2N2M0 | 50 | 37.5. | 50.9 | 20 | 12.86 |
| 48 | 72 | 1 | T2N0M0 | 25 | 45 | 53.6 | 31 | 21.43 |
| 49 | 56 | 1 | T1N0M0 | 51.25 | 46.25 | 52.7 | 38 | 21.43 |

TABLE 4-continued

| | | | | | | | | |
|---|---|---|---|---|---|---|---|---|
| 50 | 71 | 3 | T1N0M0 | 22.5 | 48.75 | 53.6 | 29 | 17.14 |
| 51 | 70 | 2 | T2N0M0 | 51.25 | 45 | 52.7 | 37 | 23.57 |
| 52 | 74 | 2 | T2N1M0 | 45 | 48.75 | 53.6 | 42 | 32.86 |
| 53 | 69 | 2 | T2N0M0 | 37.5 | 46.25 | 53.6 | 24 | 21.43 |
| 54 | 71 | 3 | T2N0M0 | 40 | 35 | 50.9 | 32 | 20.00 |
| 55 | 53 | 3 | T2N0M0 | 42.5 | 46.25 | 51.8 | 33 | 21.43 |
| 56 | 70 | 2 | T2N0M0 | 37.5 | 47.5 | 50.0 | 28 | 22.86 |
| 57 | 57 | 2 | T2N0M0 | 48.75 | 42.5 | 54.5 | 32 | 21.43 |
| 58 | 68 | 3 | T2N0M0 | 43.75 | 42.5 | 50.0 | 25 | 15.00 |
| 59 | 50 | 2 | T1N0M0 | 12.5 | 42.5 | 51.8 | 33 | 18.57 |
| 60 | 50 | 2 | T1N0M0 | 40 | 50 | 54.5 | 33 | 25.00 |
| 61 | 53 | 2 | T1N0M0 | 17.5 | 37.5 | 49.1 | 44 | 26.43 |
| 62 | 65 | 1 | T1N0M0 | 28.75 | 47.5 | 53.6 | 39 | 19.29 |
| 63 | 55 | 2 | T1N0M0 | 37.5 | 43.75 | 51.8 | 28 | 17.14 |
| 64 | 61 | 1 | T2N0M0 | 31.25 | 46.25 | 51.8 | 30 | 17.14 |
| 65 | 48 | 3 | T2N0M0 | 25 | 45 | 52.7 | 22 | 12.86 |
| 66 | 53 | 2 | T1N0M0 | 36.25 | 45 | 50.0 | 22 | 17.14 |
| 67 | 40 | 3 | T2N0M0 | 15 | 36.25 | 54.5 | 22 | 16.43 |
| 68 | 66 | 2 | T1N0M0 | 47.5 | 40 | 50.9 | 42 | 27.14 |
| 69 | 48 | 3 | T2N0M0 | 21.25 | 48.75 | 54.5 | 30 | 17.14 |
| 70 | 46 | 2 | T2N0M0 | 40 | 48.75 | 51.8 | 29 | 15.71 |
| 71 | 59 | 3 | T2N0M0 | 16.25 | 47.5 | 52.7 | 29 | 18.57 |
| 72 | 60 | 3 | T2N0M0 | 15 | 48.75 | 53.6 | 30 | 25.71 |
| 73 | 68 | 1 | T1N0M0 | 12.5 | 43.75 | 43.6 | 20 | 20.71 |
| 74 | 59 | 3 | T2N1M0 | 18.75 | 45 | 52.7 | 39 | 29.29 |
| 75 | 62 | 3 | T1N0M0 | 15 | 48.75 | 53.6 | 31 | 15.71 |
| 76 | 58 | 2 | T2N0M0 | 16.25 | 47.5 | 53.6 | 29 | 21.43 |
| 77 | 62 | 3 | T1N0M0 | 26.25 | 47.5 | 51.8 | 27 | 20.00 |
| 78 | 55 | 3 | T1N0M0 | 12.5 | 46.25 | 52.7 | 23 | 14.29 |
| 79 | 50 | 2 | T2N0M0 | 18.75 | 46.25 | 54.5 | 23 | 19.29 |
| 80 | 56 | 3 | T1N0M0 | 41.25 | 43.75 | 51.8 | 35 | 28.57 |
| 81 | 54 | 3 | T1N0M0 | 42.5 | 46.25 | 52.7 | 28 | 14.29 |
| 82 | 57 | 3 | T2N0M0 | 28.75 | 47.5 | 52.7 | 22 | 12.86 |
| 83 | 61 | 2 | T1N0M0 | 21.25 | 36.25 | 51.8 | 29 | 16.43 |
| 84 | 60 | 3 | T1N1M0 | 20 | 40 | 50.9 | 28 | 20.00 |
| 85 | 65 | 3 | T2N0M0 | 30 | 47.5 | 53.6 | 30 | 20.00 |
| 86 | 43 | 2 | T1N0M0 | 48.75 | 47.5 | 52.7 | 32 | 20.00 |
| 87 | 65 | 2 | T2N0M0 | 37.5 | 37.5 | 41.8 | 29 | 16.43 |
| 88 | 67 | 3 | T1N0M0 | 51.25 | 47.5 | 52.7 | 35 | 24.29 |
| 89 | 62 | 2 | T2N0M0 | 26.25 | 42.5 | 52.7 | 31 | 23.57 |
| 90 | 52 | 1 | T3N0M0 | 16.25 | 43.75 | 52.7 | 30 | 19.29 |
| 91 | 57 | 2 | T2N0M0 | 22.5 | 47.5 | 40.0 | 28 | 22.86 |
| 92 | 63 | 2 | T1N0M0 | 41.25 | 41.25 | 48.2 | 30 | 18.57 |
| 93 | 49 | 2 | T1N0M0 | 12.5 | 25 | 47.3 | 24 | 14.29 |
| 94 | 68 | 2 | T1N0M0 | 43.75 | 36.25 | 53.6 | 35 | 22.14 |
| 95 | 56 | 1 | T1N0M0 | 17.5 | 47.5 | 52.7 | 27 | 15.71 |
| 96 | 63 | 2 | T2N0M0 | 22.5 | 41.25 | 52.7 | 36 | 26.43 |
| 97 | 70 | 2 | T1N0M0 | 40 | 35 | 52.7 | 35 | 24.29 |
| 98 | 68 | 1 | T2N0M0 | 55 | 42.5 | 54.5 | 26 | 23.57 |
| 99 | 59 | 1 | T1N0M0 | 50 | 41.25 | 49.1 | 35 | 18.57 |
| 100 | 40 | 3 | T1N0M0 | 38.75 | 45 | 49.1 | 36 | 23.57 |
| 101 | 56 | 1 | T2N0M0 | 12.5 | 47.5 | 52.7 | 30 | 21.43 |
| 102 | 62 | 2 | T2N1M0 | 26.25 | 40 | 54.5 | 33 | 20.00 |
| 103 | 61 | 3 | T1N0M0 | 43.75 | 45 | 50.9 | 33 | 23.57 |
| 104 | 68 | 2 | T2N1M0 | 47.5 | 45 | 50.9 | 33 | 24.29 |
| 105 | 53 | 2 | T1N0M0 | 27.5 | 36.25 | 52.7 | 31 | 20.00 |
| 106 | 45 | 3 | T1N0M0 | 16.25 | 45 | 52.7 | 31 | 20.71 |
| 107 | 50 | 2 | T2N1M0 | 30 | 42.5 | 53.6 | 25 | 16.43 |
| 108 | 42 | 3 | T2N0M0 | 15 | 48.75 | 52.7 | 24 | 16.43 |
| 109 | 53 | 3 | T2N0M0 | 13.75 | 47.5 | 53.6 | 36 | 20.00 |
| 110 | 55 | 2 | T1N0M0 | 45 | 42.5 | 50.0 | 41 | 29.29 |
| 111 | 48 | 3 | T2N0M0 | 12.5 | 48.75 | 54.5 | 26 | 15.00 |
| 112 | 31 | 3 | T1N0M0 | 40 | 43.75 | 53.6 | 31 | 19.29 |
| 113 | 53 | 3 | T1N0M0 | 12.5 | 42.5 | 45.5 | 30 | 20.71 |
| 114 | 65 | 2 | T1N1M0 | 12.5 | 40 | 44.5 | 37 | 21.43 |
| 115 | 40 | 3 | T1N0M0 | 31.25 | 40 | 51.8 | 35 | 24.29 |
| 116 | 69 | 3 | T1N0M0 | 17.5 | 42.5 | 47.3 | 36 | 15.00 |
| 117 | 74 | 3 | T2N0M0 | 36.25 | 35 | 47.3 | 30 | 17.86 |
| 118 | 62 | 2 | T2N0M0 | 32.5 | 40 | 52.7 | 32 | 21.43 |
| 119 | 62 | 2 | T1N0M0 | 12.5 | 42.5 | 50.9 | 28 | 16.43 |
| 120 | 55 | 2 | T1N0M0 | 42.5 | 47.5 | 52.7 | 36 | 21.43 |
| 121 | 52 | 1 | T2N0M0 | 40 | 40 | 51.8 | 42 | 17.14 |
| 122 | 56 | 3 | T2N1M0 | 13.75 | 46.25 | 52.7 | 30 | 22.86 |
| 123 | 63 | 2 | T2N0M0 | 28.75 | 47.5 | 52.7 | 34 | 20.00 |
| 124 | 58 | 1 | T1N0M0 | 35 | 47.5 | 47.3 | 26 | 17.14 |
| 125 | 59 | 2 | T1N0M0 | 43.75 | 43.75 | 45.5 | 32 | 22.14 |
| 126 | 44 | 2 | T1N0M0 | 16.25 | 37.5 | 50.9 | 26 | 15.00 |
| 127 | 54 | 2 | T2N0M0 | 25 | 42.5 | 49.1 | 35 | 23.57 |
| 128 | 58 | 1 | T1N0M0 | 28.75 | 45 | 47.3 | 30 | 16.43 |
| 129 | 61 | 2 | T1N0M0 | 57.5 | 42.5 | 52.7 | 22 | 24.29 |

TABLE 4-continued

| | | | | | | | | |
|---|---|---|---|---|---|---|---|---|
| 130 | 66 | 1 | T1N0M0 | 50 | 47.5 | 49.1 | 30 | 22.86 |
| 131 | 63 | 2 | T1N0M0 | 12.5 | 42.5 | 46.4 | 24 | 12.86 |
| 132 | 52 | 2 | T1N0M0 | 12.5 | 43.75 | 52.7 | 20 | 12.86 |
| 133 | 65 | 2 | T1N0M0 | 50 | 47.5 | 54.5 | 32 | 17.14 |
| 134 | 49 | 1 | T1N0M0 | 40 | 30 | 50.0 | 20 | 12.86 |
| 135 | 72 | 2 | T2N0M0 | 50 | 42.5 | 52.7 | 34 | 14.29 |
| 136 | 54 | 2 | T2N1M0 | 18.75 | 46.25 | 50.9 | 32 | 17.14 |
| 137 | 68 | 1 | T1N0M0 | 51.25 | 38.75 | 50.9 | 26 | 20.00 |
| 138 | 64 | 2 | T1N0M0 | 45 | 45 | 54.5 | 20 | 15.00 |
| 139 | 47 | 2 | T1N0M0 | 36.25 | 41.25 | 48.2 | 22 | 18.57 |
| 140 | 57 | 3 | T1N0M0 | 25 | 42.5 | 45.5 | 20 | 12.86 |
| 141 | 62 | 2 | T1N0M0 | 13.75 | 35 | 54.5 | 34 | 18.57 |
| 142 | 72 | 3 | T1N0M0 | 27.5 | 33.75 | 43.6 | 28 | 15.71 |
| 143 | 67 | 3 | T1N0M0 | 12.5 | 46.25 | 54.5 | 31 | 25.00 |
| 144 | 50 | 3 | T2N0M0 | 52.5 | 43.75 | 49.1 | 29 | 14.29 |
| 145 | 26 | 2 | T2N0M0 | 50 | 45 | 50.9 | 35 | 22.86 |
| 146 | 59 | 3 | T1N0M0 | 50 | 32.5 | 49.1 | 31 | 19.29 |
| 147 | 69 | 2 | T1N0M0 | 52.5 | 37.5 | 50.0 | 42 | 31.43 |
| 148 | 72 | 2 | T1N0M0 | 48.75 | 43.75 | 53.6 | 32 | 14.29 |
| 149 | 66 | 2 | T2N0M0 | 37.5 | 32.5 | 47.3 | 30 | 25.00 |
| 150 | 62 | 2 | T1N0M0 | 33.75 | 45 | 52.7 | 20 | 17.14 |
| 151 | 43 | 2 | T1N0M0 | 30 | 42.5 | 51.8 | 31 | 25.00 |
| 152 | 61 | 2 | T1N0M0 | 48.75 | 43.75 | 51.8 | 24 | 15.71 |
| 153 | 65 | 1 | T1N0M0 | 27.5 | 33.75 | 52.7 | 22 | 12.86 |
| 154 | 60 | 3 | T2N2M0 | 37.5 | 47.5 | 52.7 | 28 | 28.57 |
| 155 | 41 | 3 | T3N0M0 | 12.5 | 45 | 50.9 | 42 | 22.86 |
| 156 | 47 | 2 | T2N2M0 | 50 | 37.5 | 45.5 | 50 | 35.71 |
| 157 | 62 | 2 | T2N2M0 | 15 | 42.5 | 49.1 | 40 | 27.14 |
| 158 | 50 | 3 | T2N2M0 | 15 | 42.5 | 47.3 | 40 | 31.43 |
| 159 | 50 | 2 | T2N1M0 | 12.5 | 42.5 | 49.1 | 44 | 12.86 |
| 160 | 48 | 2 | T2N1M0 | 12.5 | 45 | 52.7 | 40 | 12.86 |
| 161 | 45 | 2 | T2N0M0 | 52.5 | 37.5 | 52.7 | 50 | 32.86 |
| 162 | 57 | 1 | T1N0M0 | 12.5 | 47.5 | 50.9 | 40 | 21.43 |
| 163 | 57 | 2 | T2N2M0 | 12.5 | 42.5 | 52.7 | 40 | 21.43 |
| 164 | 36 | 2 | T2N1M0 | 30 | 45 | 50.9 | 46 | 21.43 |
| 165 | 52 | 3 | T2N1M0 | 35 | 42.5 | 52.7 | 42 | 27.14 |
| 166 | 57 | 2 | T1N2M0 | 45 | 45 | 52.7 | 30 | 15.71 |
| 167 | 46 | 2 | T3N3M0 | 42.5 | 47.5 | 52.7 | 48 | 30.00 |
| 168 | 48 | 2 | T1N2M0 | 12.5 | 47.5 | 52.7 | 40 | 17.14 |
| 169 | 55 | 2 | T2N1M0 | 16.25 | 47.5 | 53.6 | 32 | 17.14 |
| 170 | 29 | 3 | T2N0M0 | 43.75 | 45 | 50.0 | 32 | 25.71 |
| 171 | 47 | 3 | T2N0M0 | 41.25 | 43.75 | 50.0 | 42 | 26.43 |
| 172 | 51 | 3 | T2N0M0 | 15 | 47.5 | 53.6 | 31 | 19.29 |
| 173 | 56 | 2 | T1N0M0 | 46.25 | 40 | 50.9 | 28 | 12.86 |
| 174 | 49 | 2 | T2N0M0 | 32.5 | 42.5 | 52.7 | 40 | 22.86 |
| 175 | 49 | 2 | T2N0M0 | 30 | 50 | 54.5 | 24 | 34.29 |
| 176 | 48 | 2 | T2N2M0 | 28.75 | 45 | 54.5 | 28 | 15.00 |
| 177 | 74 | 2 | T2N0M0 | 48.75 | 48.75 | 52.7 | 28 | 20.71 |
| 178 | 65 | 3 | T2N1M0 | 15 | 43.75 | 50.0 | 36 | 24.29 |
| 179 | 55 | 2 | T2N1M0 | 12.5 | 33.75 | 50.0 | 41 | 22.86 |
| 180 | 61 | 2 | T2N1M0 | 12.5 | 43.75 | 49.1 | 28 | 16.43 |
| 181 | 47 | 1 | T1N0M0 | 26.25 | 45 | 53.6 | 22 | 18.57 |
| 182 | 37 | 2 | T1N0M0 | 33.75 | 35 | 47.3 | 27 | 17.86 |
| 183 | 52 | 2 | T2N0M0 | 35 | 45 | 50.9 | 37 | 25.00 |
| 184 | 47 | 2 | T1N0M0 | 42.5 | 46.25 | 52.7 | 29 | 19.29 |
| 185 | 68 | 3 | T2N0M0 | 55 | 42.5 | 50.9 | 24 | 18.57 |
| 186 | 37 | 2 | T2N0M0 | 20 | 42.5 | 52.7 | 20 | 24.29 |
| 187 | 48 | 3 | T2N0M0 | 23.75 | 46.25 | 52.7 | 27 | 17.14 |
| 188 | 50 | 1 | T2N0M0 | 22.5 | 40 | 37.3 | 24 | 20.00 |
| 189 | 60 | 3 | T2N0M0 | 37.5 | 32.5 | 50.9 | 33 | 24.29 |
| 190 | 65 | 2 | T2N0M0 | 13.75 | 17.5 | 41.8 | 26 | 17.14 |
| 191 | 53 | 2 | T2N0M0 | 40 | 52.5 | 52.7 | 20 | 17.86 |
| 192 | 62 | 2 | T2N0M0 | 22.5 | 45 | 50.9 | 26 | 18.57 |
| 193 | 61 | 2 | T2N0M0 | 16.25 | 41.25 | 46.4 | 20 | 12.86 |
| 194 | 68 | 3 | T2N0M0 | 22.5 | 43.75 | 50.9 | 34 | 20.00 |
| 195 | 47 | 2 | T1N1M0 | 31.25 | 48.75 | 52.7 | 28 | 17.86 |
| 196 | 60 | 3 | T2N0M0 | 15 | 47.5 | 50.9 | 24 | 15.71 |
| 197 | 49 | 2 | T2N0M0 | 22.5 | 47.5 | 52.7 | 24 | 16.43 |
| 198 | 42 | 2 | T2N0M0 | 25 | 45 | 50.9 | 26 | 12.86 |
| 199 | 39 | 2 | T2N1M0 | 20 | 45 | 51.8 | 27 | 16.43 |
| 200 | 61 | 2 | T2N1M0 | 12.5 | 46.25 | 52.7 | 29 | 19.29 |
| 201 | 48 | 3 | T2N1M0 | 12.5 | 47.5 | 52.7 | 27 | 18.57 |
| 202 | 49 | 2 | T2N1M0 | 12.5 | 37.5 | 52.7 | 28 | 14.29 |
| 203 | 56 | 3 | T2N1M0 | 12.5 | 32.5 | 41.8 | 26 | 24.29 |
| 204 | 59 | 2 | T2N1M0 | 42.5 | 37.5 | 45.5 | 30 | 18.57 |
| 205 | 61 | 2 | T2N1M0 | 42.5 | 42.5 | 52.7 | 34 | 15.71 |
| 206 | 47 | 2 | T2N1M0 | 12.5 | 42.5 | 52.7 | 40 | 24.29 |
| 207 | 45 | 2 | T2N1M0 | 22.5 | 45 | 52.7 | 20 | 12.86 |
| 208 | 61 | 3 | T2N1M0 | 12.5 | 42.5 | 51.8 | 36 | 17.86 |
| 209 | 67 | 3 | T2N1M0 | 12.5 | 45 | 54.5 | 24 | 17.14 |

TABLE 4-continued

| | | | | | | | | |
|---|---|---|---|---|---|---|---|---|
| 210 | 57 | 2 | T2N1M0 | 17.5 | 47.5 | 41.8 | 22 | 15.71 |
| 211 | 56 | 2 | T2N1M0 | 42.5 | 22.5 | 38.2 | 20 | 17.14 |
| 212 | 76 | 3 | T2N2M0 | 18.75 | 47.5 | 47.3 | 22 | 18.57 |
| 213 | 40 | 2 | T3N1M0 | 25 | 37.5 | 50.9 | 32 | 22.86 |
| 214 | 70 | 2 | T2N2M0 | 12.5 | 45 | 50.9 | 30 | 16.43 |
| 215 | 47 | 3 | T2N2M0 | 23.75 | 42.5 | 41.8 | 22 | 17.14 |
| 216 | 48 | 3 | T2N2M0 | 20 | 45 | 50.9 | 26 | 12.86 |
| 217 | 58 | 3 | T2N2M0 | 12.5 | 45 | 53.6 | 24 | 16.43 |
| 218 | 55 | 3 | T2N0M0 | 31.25 | 47.5 | 49.1 | 24 | 12.86 |
| 219 | 40 | 3 | T2N0M0 | 38.75 | 42.5 | 50.0 | 25 | 17.14 |
| 220 | 34 | 2 | T2N0M0 | 12.5 | 46.25 | 51.8 | 24 | 12.86 |
| 221 | 57 | 3 | T2N0M0 | 15 | 45 | 50.0 | 22 | 27.14 |
| 222 | 73 | 2 | T2N0M0 | 20 | 46.25 | 50.9 | 34 | 17.86 |
| 223 | 53 | 2 | T2N0M0 | 37.5 | 45 | 50.0 | 27 | 17.86 |
| 224 | 55 | 3 | T2N0M0 | 21.25 | 47.5 | 53.6 | 20 | 12.86 |
| 225 | 60 | 3 | T2N0M0 | 25 | 43.75 | 53.6 | 20 | 17.86 |
| 226 | 63 | 3 | T2N0M0 | 18.75 | 47.5 | 52.7 | 23 | 14.29 |
| 227 | 58 | 2 | T2N0M0 | 38.75 | 43.75 | 50.0 | 39 | 24.29 |
| 228 | 55 | 2 | T1N0M0 | 21.25 | 43.75 | 53.6 | 23 | 14.29 |
| 229 | 60 | 3 | T3N0M0 | 12.5 | 41.25 | 53.6 | 34 | 17.14 |
| 230 | 66 | 3 | T2N0M0 | 16.25 | 50 | 53.6 | 26 | 15.71 |
| 231 | 41 | 3 | T2N0M0 | 17.5 | 47.5 | 50.9 | 28 | 17.14 |
| 232 | 43 | 3 | T2N0M0 | 12.5 | 47.5 | 52.7 | 26 | 15.71 |
| 233 | 47 | 2 | T1N0M0 | 46.25 | 27.5 | 49.1 | 20 | 20.00 |
| 234 | 62 | 2 | T1N0M0 | 12.5 | 40 | 49.1 | 28 | 27.86 |
| 235 | 57 | 2 | T2N0M0 | 55 | 48.75 | 51.8 | 43 | 31.43 |
| 236 | 52 | 3 | T2N0M0 | 47.5 | 47.5 | 53.6 | 25 | 22.14 |
| 237 | 85 | 2 | T2N0M0 | 12.5 | 48.75 | 54.5 | 30 | 16.43 |
| 238 | 64 | 3 | T2N0M0 | 41.25 | 43.75 | 51.8 | 31 | 20.00 |
| 239 | 67 | 2 | T3N0M0 | 20 | 37.5 | 52.7 | 26 | 18.57 |
| 240 | 61 | 2 | T1N0M0 | 15 | 43.75 | 51.8 | 36 | 18.57 |
| 241 | 55 | 2 | T2N0M0 | 40 | 47.5 | 52.7 | 36 | 22.86 |
| 242 | 66 | 3 | T2N0M0 | 35 | 42.5 | 51.8 | 35 | 25.00 |
| 243 | 39 | 3 | T2N0M0 | 12.5 | 30 | 50.9 | 24 | 16.43 |
| 244 | 53 | 2 | T2N0M0 | 46.25 | 40 | 48.2 | 36 | 14.29 |
| 245 | 54 | 2 | T2N0M0 | 23.75 | 46.25 | 52.7 | 24 | 21.43 |
| 246 | 58 | 2 | T1N0M0 | 36.25 | 48.75 | 53.6 | 32 | 27.14 |
| 247 | 40 | 3 | T1N0M0 | 36.25 | 46.25 | 50.9 | 39 | 28.57 |
| 248 | 67 | 2 | T1N0M0 | 27.5 | 47.5 | 52.7 | 28 | 15.71 |
| 249 | 61 | 3 | T2N0M0 | 16.25 | 41.25 | 51.8 | 35 | 23.57 |
| 250 | 45 | 1 | T3N3M0 | 22.5 | 42.5 | 52.72727273 | 26 | 21.42857143 |
| 251 | 69 | 2 | T4N1M0 | 20 | 47.5 | 52.72727273 | 44 | 24.28571429 |
| 252 | 61 | 3 | T4N1M0 | 47.5 | 45 | 52.72727273 | 36 | 21.42857143 |
| 253 | 55 | 3 | T2N2M0 | 22.5 | 47.5 | 52.72727273 | 46 | 27.14285714 |
| 254 | 44 | 2 | T3N1M0 | 45 | 47.5 | 52.72727273 | 44 | 31.42857143 |
| 255 | 64 | 2 | T1N0M0 | 14.16666667 | 45 | 47.27272727 | 36 | 18.57142857 |
| 256 | 63 | 2 | T2N2M0 | 22.5 | 43.75 | 51.81818182 | 30 | 20 |
| 257 | 48 | 1 | T1N1M0 | 30 | 42.5 | 47.27272727 | 33 | 28.57142857 |
| 258 | 50 | 2 | T2N1M0 | 32.5 | 45 | 50 | 36 | 18.57142857 |
| 259 | 41 | 2 | T2N2M0 | 16.25 | 45 | 50.90909091 | 26 | 16.42857143 |
| 260 | 60 | 2 | T2N0M0 | 16.25 | 45 | 51.81818182 | 32 | 18.57142857 |
| 261 | 49 | 3 | T2N0M0 | 20 | 27.5 | 52.72727273 | 32 | 21.42857143 |
| 262 | 50 | 2 | T2N0M0 | 52.5 | 46.25 | 52.72727273 | 37 | 22.14285714 |
| 263 | 49 | 2 | T2N0M0 | 22.5 | 47.5 | 54.54545455 | 27 | 15.71428571 |
| 264 | 50 | 3 | T2N1M0 | 27.5 | 47.5 | 51.81818182 | 32 | 21.42857143 |
| 265 | 55 | 2 | T2N2M0 | 16.25 | 45 | 49.09090909 | 28 | 14.28571429 |
| 266 | 57 | 2 | T2N0M0 | 37.5 | 40 | 53.63636364 | 32 | 12.85714286 |
| 267 | 41 | 2 | T2N0M0 | 45 | 47.5 | 52.72727273 | 45 | 20 |
| 268 | 48 | 1 | T2N0M0 | 15 | 43.75 | 54.54545455 | 35 | 16.42857143 |
| 269 | 63 | 3 | T2N0M0 | 22.5 | 46.25 | 54.54545455 | 30 | 15 |
| 270 | 65 | 2 | T2N0M0 | 32.5 | 46.25 | 54.54545455 | 38 | 23.57142857 |
| 271 | 55 | 2 | T2N0M0 | 27.5 | 46.25 | 52.72727273 | 34 | 22.85714286 |
| 272 | 61 | 2 | T2N0M0 | 41.25 | 45 | 52.72727273 | 33 | 25.71428571 |
| 273 | 67 | 2 | T2N0M0 | 45 | 47.5 | 52.72727273 | 34 | 27.14285714 |
| 274 | 74 | 2 | T2N1M0 | 20 | 46.25 | 51.81818182 | 35 | 30 |
| 275 | 66 | 2 | T1N0M0 | 15 | 47.5 | 54.54545455 | 35 | 28.57142857 |
| 276 | 61 | 2 | T2N0M0 | 36.25 | 50 | 52.72727273 | 35 | 25.71428571 |
| 277 | 35 | 2 | T2N0M0 | 40 | 42.5 | 50.90909091 | 40 | 25.71428571 |
| 278 | 57 | 2 | T2N1M0 | 15 | 46.25 | 51.81818182 | 38 | 23.57142857 |
| 279 | 34 | 3 | T2N0M0 | 20 | 46.25 | 52.72727273 | 39 | 27.14285714 |
| 280 | 41 | 2 | T2N0M0 | 50 | 47.5 | 49.09090909 | 39 | 25.71428571 |
| 281 | 55 | 2 | T2N0M0 | 43.75 | 46.25 | 51.81818182 | 40 | 27.14285714 |
| 282 | 55 | 2 | T1N0M0 | 43.75 | 46.25 | 51.81818182 | 40 | 27.14285714 |
| 283 | 63 | 2 | T2N1M0 | 27.5 | 42.5 | 52.72727273 | 36 | 21.42857143 |
| 284 | 49 | 2 | T2N1M0 | 17.5 | 47.5 | 52.72727273 | 40 | 15.71428571 |
| 285 | 65 | 2 | T2N1M0 | 25 | 45 | 52.72727273 | 40 | 25.71428571 |
| 286 | 40 | 2 | T2N0M0 | 33.33333334 | 45 | 53.93939394 | 37.33333333 | 24.28571429 |
| 287 | 43 | 1 | T1N0M0 | 15.83333333 | 43.33333334 | 53.33333333 | 30 | 18.09523809 |
| 288 | 44 | 3 | T2N2M0 | 12.5 | 46.25 | 51.81818182 | 24 | 14.28571429 |
| 289 | 59 | 2 | T1N1M0 | 15 | 46.25 | 52.72727273 | 28 | 16.42857143 |

TABLE 4-continued

| | | | | | | | | |
|---|---|---|---|---|---|---|---|---|
| 290 | 73 | 2 | T2N1M0 | 35 | 45 | 52.72727273 | 34 | 18.57142857 |
| 291 | 61 | 2 | T2N1M0 | 26.25 | 47.5 | 52.72727273 | 31 | 34.28571429 |
| 292 | 37 | 2 | T2N1M0 | 40 | 47.5 | 52.72727273 | 33 | 21.42857143 |
| 293 | 55 | 2 | T2N1M0 | 12.5 | 40 | 49.09090909 | 30 | 19.28571429 |
| 294 | 37 | 2 | T2N0M0 | 41.25 | 37.5 | 52.72727273 | 26 | 15.71428571 |
| 295 | 67 | 2 | T2N0M0 | 32.5 | 47.5 | 52.72727273 | 36 | 22.85714286 |
| 296 | 38 | 2 | T2N0M0 | 25 | 42.5 | 52.72727273 | 30 | 23.57142857 |
| 297 | 49 | 2 | T1N0M0 | 31.25 | 42.5 | 50.90909091 | 31 | 22.85714286 |
| 298 | 65 | 2 | T2N0M0 | 23.75 | 36.25 | 47.27272727 | 25 | 17.85714286 |
| 299 | 40 | 2 | T2N0M0 | 12.5 | 32.5 | 50 | 30 | 35.71428571 |

| Sl. No | WI-C | Outcome | DFS | TTP | Chemo Details | CanAssist Breast Score |
|---|---|---|---|---|---|---|
| 1 | 1.3 | Recurrence | | 35 | Chemo Naive | 45.6 |
| 2 | 1.8 | Recurrence | | 60 | Chemo Naive | 15.6 |
| 3 | 1.5 | Recurrence | | 44 | Chemo Naive | 19.4 |
| 4 | 1.8 | Recurrence | | 52 | Chemo Naive | 11.5 |
| 5 | 1.5 | Recurrence | | 55 | Chemo Naive | 20.8 |
| 6 | 1.5 | Recurrence | | 43 | Chemo Naive | 13.9 |
| 7 | 1.8 | Recurrence | | 46 | Chemo Naive | 24.1 |
| 8 | 1.3 | Recurrence | | 53 | Chemo Naive | 23.8 |
| 9 | 1.5 | No Recurrence | 76 | | Chemo Naive | 8.3 |
| 10 | 1.8 | No Recurrence | 80 | | Chemo Naive | 8.3 |
| 11 | 1.6 | No Recurrence | 65 | | Chemo Naive | 2.5 |
| 12 | 1.6 | No Recurrence | 64 | | Chemo Naive | 8.1 |
| 13 | 1.6 | No Recurrence | 68 | | Chemo Naive | 9 |
| 14 | 1.8 | No Recurrence | 61 | | Chemo Naive | 5.5 |
| 15 | 1.4 | No Recurrence | 74 | | Chemo Naive | 7.1 |
| 16 | 1.4 | No Recurrence | 75 | | Chemo Naive | 7.5 |
| 17 | 1.8 | No Recurrence | 74 | | Chemo Naive | 4 |
| 18 | 1.8 | No Recurrence | 88 | | Chemo Naive | 6.7 |
| 19 | 1.5 | No Recurrence | 137 | | Chemo Naive | 9.8 |
| 20 | 1.4 | No Recurrence | 69 | | Chemo Naive | 11.5 |
| 21 | 1.1 | No Recurrence | 66 | | Chemo Naive | 4 |
| 22 | 1.5 | No Recurrence | 65 | | Chemo Naive | 5.6 |
| 23 | 1.8 | No Recurrence | 78 | | Chemo Naive | 3.7 |
| 24 | 1.5 | No Recurrence | 71 | | Chemo Naive | 3.4 |
| 25 | 1.5 | No Recurrence | 103 | | Chemo Naive | 5.4 |
| 26 | 1.6 | No Recurrence | 60 | | Chemo Naive | 5.9 |
| 27 | 1.8 | No Recurrence | 60 | | Chemo Naive | 3.7 |
| 28 | 1.8 | No Recurrence | 60 | | Chemo Naive | 13.1 |
| 29 | 1.5 | No Recurrence | 85 | | Chemo Naive | 10.3 |
| 30 | 1.6 | No Recurrence | 93 | | Chemo Naive | 15 |
| 31 | 1.5 | No Recurrence | 109 | | Chemo Naive | 12.4 |
| 32 | 1.3 | No Recurrence | 130 | | Chemo Naive | 10.9 |
| 33 | 1.5 | No Recurrence | 79 | | Chemo Naive | 12.7 |
| 34 | 1.9 | No Recurrence | 68 | | Chemo Naive | 9.1 |
| 35 | 1.8 | No Recurrence | 86 | | Chemo Naive | 12.4 |
| 36 | 1.6 | No Recurrence | 69 | | Chemo Naive | 7.7 |
| 37 | 1.6 | No Recurrence | 86 | | Chemo Naive | 6.8 |
| 38 | 1.4 | No Recurrence | 77 | | Chemo Naive | 10.5 |
| 39 | 1.8 | No Recurrence | 83 | | Chemo Naive | 8.4 |
| 40 | 1.6 | No Recurrence | 60 | | Chemo Naive | 8.4 |
| 41 | 1.5 | No Recurrence | 63 | | Chemo Naive | 7.8 |
| 42 | 1.6 | No Recurrence | 63 | | Chemo Naive | 15 |
| 43 | 1.5 | No Recurrence | 63 | | Chemo Naive | 9 |
| 44 | 1.5 | No Recurrence | 69 | | Chemo Naive | 13 |
| 45 | 1.4 | No Recurrence | 71 | | Chemo Naive | 11.1 |
| 46 | 1.4 | No Recurrence | 76 | | Chemo Naive | 6.7 |
| 47 | 1.4 | No Recurrence | 60 | | Chemo Naive | 9.8 |
| 48 | 1.9 | No Recurrence | 67 | | Chemo Naive | 6.9 |
| 49 | 1.6 | No Recurrence | 67 | | Chemo Naive | 7.4 |
| 50 | 1.6 | No Recurrence | 61 | | Chemo Naive | 9.8 |
| 51 | 1.5 | No Recurrence | 65 | | Chemo Naive | 10.1 |
| 52 | 1.6 | No Recurrence | 72 | | Chemo Naive | 16.1 |
| 53 | 1.5 | No Recurrence | 76 | | Chemo Naive | 5.2 |
| 54 | 1.4 | No Recurrence | 65 | | Chemo Naive | 11.7 |
| 55 | 1.5 | No Recurrence | 70 | | Chemo Naive | 10 |
| 56 | 1.8 | No Recurrence | 64 | | Chemo Naive | 3 |
| 57 | 1.4 | No Recurrence | 64 | | Chemo Naive | 9.9 |
| 58 | 1.5 | No Recurrence | 84 | | Chemo Naive | 7.4 |
| 59 | 1.4 | No Recurrence | 81 | | Chemo Naive | 7.6 |
| 60 | 1.8 | No Recurrence | 133 | | Chemo Naive | 4.1 |
| 61 | 1.4 | No Recurrence | 86 | | Chemo Naive | 10.1 |
| 62 | 1.6 | No Recurrence | 62 | | Chemo Naive | 8.7 |
| 63 | 1.6 | No Recurrence | 66 | | Chemo Naive | 4.8 |
| 64 | 1.4 | No Recurrence | 66 | | Chemo Naive | 7.6 |
| 65 | 1.1 | No Recurrence | 79 | | Chemo Naive | 7.7 |
| 66 | 1.6 | No Recurrence | 82 | | Chemo Naive | 5.3 |

TABLE 4-continued

| | | | | | |
|---|---|---|---|---|---|
| 67 | 1.5 | No Recurrence | 84 | Chemo Naive | 4.4 |
| 68 | 1.3 | No Recurrence | 135 | Chemo Naive | 17.4 |
| 69 | 1.8 | No Recurrence | 81 | Chemo Naive | 7.8 |
| 70 | 1.8 | No Recurrence | 89 | Chemo Naive | 6.4 |
| 71 | 1.6 | No Recurrence | 89 | Chemo Naive | 6.2 |
| 72 | 1.6 | No Recurrence | 84 | Chemo Naive | 6.8 |
| 73 | 1.5 | No Recurrence | 98 | Chemo Naive | 10.8 |
| 74 | 1.6 | No Recurrence | 86 | Chemo Naive | 16 |
| 75 | 1.8 | No Recurrence | 78 | Chemo Naive | 13 |
| 76 | 1.5 | No Recurrence | 91 | Chemo Naive | 5.2 |
| 77 | 1.6 | No Recurrence | 60 | Chemo Naive | 6.4 |
| 78 | 1.8 | No Recurrence | 92 | Chemo Naive | 13.9 |
| 79 | 1.6 | No Recurrence | 78 | Chemo Naive | 7.1 |
| 80 | 1.4 | No Recurrence | 61 | Chemo Naive | 14.2 |
| 81 | 1.5 | No Recurrence | 91 | Chemo Naive | 10.6 |
| 82 | 1.5 | No Recurrence | 99 | Chemo Naive | 7.9 |
| 83 | 1.3 | No Recurrence | 60 | Chemo Naive | 5.2 |
| 84 | 1.4 | No Recurrence | 87 | Chemo Naive | 8.3 |
| 85 | 1.8 | No Recurrence | 67 | Chemo Naive | 5.8 |
| 86 | 1.6 | No Recurrence | 60 | Chemo Naive | 5.9 |
| 87 | 1.3 | No Recurrence | 61 | Chemo Naive | 6.2 |
| 88 | 1.5 | No Recurrence | 62 | Chemo Naive | 13.2 |
| 89 | 1.6 | No Recurrence | 60 | Chemo Naive | 2.3 |
| 90 | 1.5 | No Recurrence | 63 | Chemo Naive | 16.1 |
| 91 | 1.6 | No Recurrence | 64 | Chemo Naive | 5.7 |
| 92 | 1.6 | No Recurrence | 81 | Chemo Naive | 3 |
| 93 | 1.0 | No Recurrence | 68 | Chemo Naive | 1.9 |
| 94 | 1.3 | No Recurrence | 72 | Chemo Naive | 10.6 |
| 95 | 1.6 | No Recurrence | 63 | Chemo Naive | 16.5 |
| 96 | 1.5 | No Recurrence | 60 | Chemo Naive | 4.1 |
| 97 | 1.3 | No Recurrence | 76 | Chemo Naive | 9.2 |
| 98 | 1.5 | No Recurrence | 105 | Chemo Naive | 11.2 |
| 99 | 1.4 | No Recurrence | 99 | Chemo Naive | 8.9 |
| 100 | 1.6 | No Recurrence | 70 | Chemo Naive | 8.2 |
| 101 | 1.8 | No Recurrence | 68 | Chemo Naive | 9.9 |
| 102 | 1.5 | No Recurrence | 69 | Chemo Naive | 6.3 |
| 103 | 1.6 | No Recurrence | 92 | Chemo Naive | 9.7 |
| 104 | 1.4 | No Recurrence | 94 | Chemo Naive | 11.8 |
| 105 | 1.4 | No Recurrence | 91 | Chemo Naive | 3.9 |
| 106 | 1.4 | No Recurrence | 88 | Chemo Naive | 8.9 |
| 107 | 1.4 | No Recurrence | 84 | Chemo Naive | 5.2 |
| 108 | 1.6 | No Recurrence | 61 | Chemo Naive | 7.8 |
| 109 | 1.5 | No Recurrence | 94 | Chemo Naive | 9.2 |
| 110 | 1.6 | No Recurrence | 98 | Chemo Naive | 6.9 |
| 111 | 1.5 | No Recurrence | 74 | Chemo Naive | 10 |
| 112 | 1.3 | No Recurrence | 73 | Chemo Naive | 12.3 |
| 113 | 1.5 | No Recurrence | 67 | Chemo Naive | 6.3 |
| 114 | 1.3 | No Recurrence | 64 | Chemo Naive | 14.1 |
| 115 | 1.3 | No Recurrence | 72 | Chemo Naive | 12.5 |
| 116 | 1.5 | No Recurrence | 71 | Chemo Naive | 8.9 |
| 117 | 1.3 | No Recurrence | 72 | Chemo Naive | 9.4 |
| 118 | 1.3 | No Recurrence | 85 | Chemo Naive | 5.7 |
| 119 | 1.6 | No Recurrence | 95 | Chemo Naive | 7.8 |
| 120 | 1.5 | No Recurrence | 66 | Chemo Naive | 6 |
| 121 | 1.4 | No Recurrence | 60 | Chemo Naive | 12 |
| 122 | 1.5 | No Recurrence | 110 | Chemo Naive | 8.5 |
| 123 | 1.5 | No Recurrence | 78 | Chemo Naive | 4.5 |
| 124 | 1.6 | No Recurrence | 82 | Chemo Naive | 8.4 |
| 125 | 1.5 | No Recurrence | 110 | Chemo Naive | 4.3 |
| 126 | 1.3 | No Recurrence | 67 | Chemo Naive | 5.7 |
| 127 | 1.5 | No Recurrence | 65 | Chemo Naive | 3 |
| 128 | 1.6 | No Recurrence | 60 | Chemo Naive | 7.7 |
| 129 | 1.5 | No Recurrence | 61 | Chemo Naive | 9.4 |
| 130 | 1.6 | No Recurrence | 71 | Chemo Naive | 5.8 |
| 131 | 1.5 | No Recurrence | 66 | Chemo Naive | 8.7 |
| 132 | 1.3 | No Recurrence | 71 | Chemo Naive | 13.9 |
| 133 | 1.5 | No Recurrence | 62 | Chemo Naive | 9.9 |
| 134 | 1.3 | No Recurrence | 63 | Chemo Naive | 9 |
| 135 | 1.8 | No Recurrence | 63 | Chemo Naive | 9.9 |
| 136 | 1.4 | No Recurrence | 63 | Chemo Naive | 7.4 |
| 137 | 1.1 | No Recurrence | 62 | Chemo Naive | 11 |
| 138 | 1.5 | No Recurrence | 65 | Chemo Naive | 11.6 |
| 139 | 1.5 | No Recurrence | 63 | Chemo Naive | 2.7 |
| 140 | 1.5 | No Recurrence | 67 | Chemo Naive | 6 |
| 141 | 1.4 | No Recurrence | 68 | Chemo Naive | 7.8 |
| 142 | 1.3 | No Recurrence | 68 | Chemo Naive | 6 |
| 143 | 1.6 | No Recurrence | 61 | Chemo Naive | 9.3 |
| 144 | 1.4 | No. Recurrence | 70 | Chemo Naive | 14.2 |
| 145 | 1.5 | No Recurrence | 72 | Chemo Naive | 8.4 |
| 146 | 1.3 | No Recurrence | 68 | Chemo Naive | 16.9 |

TABLE 4-continued

| | | | | | | |
|---|---|---|---|---|---|---|
| 147 | 1.8 | No Recurrence | 62 | | Chemo Naive | 11.5 |
| 148 | 1.4 | No Recurrence | 65 | | Chemo Naive | 11.8 |
| 149 | 1.3 | No Recurrence | 60 | | Chemo Naive | 7.2 |
| 150 | 1.5 | No Recurrence | 60 | | Chemo Naive | 7.7 |
| 151 | 1.4 | No Recurrence | 60 | | Chemo Naive | 3.6 |
| 152 | 1.4 | No Recurrence | 68 | | Chemo Naive | 8.4 |
| 153 | 1.3 | No Recurrence | 62 | | Chemo Naive | 11.5 |
| 154 | 1.8 | Recurrence | | 12 | Chemo Treated | 16.7 |
| 155 | 1.3 | Recurrence | | 37 | Chemo Treated | 30.1 |
| 156 | 1.3 | Recurrence | | 45 | Chemo Treated | 100 |
| 157 | 1.3 | Recurrence | | 54 | Chemo Treated | 27.2 |
| 158 | 1.5 | Recurrence | | 40 | Chemo Treated | 39.4 |
| 159 | 1.5 | Recurrence | | 50 | Chemo Treated | 19.8 |
| 160 | 1.8 | Recurrence | | 26 | Chemo Treated | 15.8 |
| 161 | 1.5 | Recurrence | | 18 | Chemo Treated | 35.5 |
| 162 | 1.5 | Recurrence | | 21 | Chemo Treated | 16.2 |
| 163 | 1.5 | Recurrence | | 27 | Chemo Treated | 19.4 |
| 164 | 1.5 | Recurrence | | 45 | Chemo Treated | 16.8 |
| 165 | 1.5 | Recurrence | | 35 | Chemo Treated | 25.4 |
| 166 | 1.3 | Recurrence | | 49 | Chemo Treated | 18.9 |
| 167 | 1.8 | Recurrence | | 20 | Chemo Treated | 60.8 |
| 168 | 1.8 | Recurrence | | 9 | Chemo Treated | 27.2 |
| 169 | 1.8 | No Recurrence | 84 | | Chemo Treated | 9.2 |
| 170 | 1.5 | No Recurrence | 87 | | Chemo Treated | 11.8 |
| 171 | 1.6 | No Recurrence | 96 | | Chemo Treated | 17.7 |
| 172 | 1.6 | No Recurrence | 87 | | Chemo Treated | 6.9 |
| 173 | 1.3 | No Recurrence | 87 | | Chemo Treated | 9.8 |
| 174 | 1.5 | No Recurrence | 89 | | Chemo Treated | 6.6 |
| 175 | 1.9 | No Recurrence | 83 | | Chemo Treated | 9.5 |
| 176 | 1.6 | No Recurrence | 83 | | Chemo Treated | 10.7 |
| 177 | 1.9 | No Recurrence | 60 | | Chemo Treated | 6.5 |
| 178 | 1.4 | No Recurrence | 60 | | Chemo Treated | 13.9 |
| 179 | 1.3 | No Recurrence | 64 | | Chemo Treated | 15.6 |
| 180 | 1.5 | No Recurrence | 68 | | Chemo Treated | 5.9 |
| 181 | 1.6 | No Recurrence | 61 | | Chemo Treated | 13.3 |
| 182 | 1.4 | No Recurrence | 68 | | Chemo Treated | 1.8 |
| 183 | 1.6 | No Recurrence | 60 | | Chemo Treated | 3 |
| 184 | 1.5 | No Recurrence | 60 | | Chemo Treated | 5.7 |
| 185 | 1.5 | No Recurrence | 66 | | Chemo Treated | 12.4 |
| 186 | 1.5 | No Recurrence | 64 | | Chemo Treated | 4.2 |
| 187 | 1.5 | No Recurrence | 61 | | Chemo Treated | 5.6 |
| 188 | 1.5 | No Recurrence | 121 | | Chemo Treated | 7.8 |
| 189 | 1.8 | No Recurrence | 60 | | Chemo Treated | 9.7 |
| 190 | 1.0 | No Recurrence | 63 | | Chemo Treated | 0 |
| 191 | 1.6 | No Recurrence | 69 | | Chemo Treated | 9.6 |
| 192 | 1.5 | No Recurrence | 62 | | Chemo Treated | 3.1 |
| 193 | 1.4 | No Recurrence | 74 | | Chemo Treated | 3.6 |
| 194 | 1.5 | No Recurrence | 60 | | Chemo Treated | 6.3 |
| 195 | 1.8 | No Recurrence | 94 | | Chemo Treated | 9.4 |
| 196 | 1.6 | No Recurrence | 75 | | Chemo Treated | 6.6 |
| 197 | 1.6 | No Recurrence | 72 | | Chemo Treated | 6.7 |
| 198 | 1.6 | No Recurrence | 60 | | Chemo Treated | 6.4 |
| 199 | 1.5 | No Recurrence | 71 | | Chemo Treated | 5.6 |
| 200 | 1.5 | No Recurrence | 60 | | Chemo Treated | 7.4 |
| 201 | 1.9 | No Recurrence | 64 | | Chemo Treated | 9.2 |
| 202 | 1.4 | No Recurrence | 71 | | Chemo Treated | 5.8 |
| 203 | 1.0 | No Recurrence | 60 | | Chemo Treated | 9.7 |
| 204 | 1.3 | No Recurrence | 67 | | Chemo Treated | 9.1 |
| 205 | 1.5 | No Recurrence | 82 | | Chemo Treated | 9.4 |
| 206 | 1.5 | No Recurrence | 93 | | Chemo Treated | 11.1 |
| 207 | 1.6 | No Recurrence | 79 | | Chemo Treated | 8.8 |
| 208 | 1.4 | No Recurrence | 71 | | Chemo Treated | 12.7 |
| 209 | 1.8 | No Recurrence | 118 | | Chemo Treated | 8.6 |
| 210 | 1.5 | No Recurrence | 72 | | Chemo Treated | 7.4 |
| 211 | 1.5 | No Recurrence | 61 | | Chemo Treated | 7.1 |
| 212 | 1.8 | No Recurrence | 78 | | Chemo Treated | 10.6 |
| 213 | 1.5 | No Recurrence | 127 | | Chemo Treated | 15.3 |
| 214 | 1.8 | No Recurrence | 127 | | Chemo Treated | 13.3 |
| 215 | 1.5 | No Recurrence | 64 | | Chemo Treated | 9.6 |
| 216 | 1.6 | No Recurrence | 85 | | Chemo Treated | 10.1 |
| 217 | 1.6 | No Recurrence | 62 | | Chemo Treated | 10.7 |
| 218 | 1.6 | No Recurrence | 61 | | Chemo Treated | 6.5 |
| 219 | 1.5 | No Recurrence | 60 | | Chemo Treated | 5.5 |
| 220 | 1.8 | No Recurrence | 60 | | Chemo Treated | 11.5 |
| 221 | 1.5 | No Recurrence | 60 | | Chemo Treated | 5.5 |
| 222 | 1.6 | No Recurrence | 64 | | Chemo Treated | 4.5 |
| 223 | 1.5 | No Recurrence | 64 | | Chemo Treated | 3.6 |
| 224 | 1.8 | No Recurrence | 62 | | Chemo Treated | 10.8 |
| 225 | 1.8 | No Recurrence | 65 | | Chemo Treated | 6.4 |
| 226 | 1.8 | No Recurrence | 60 | | Chemo Treated | 8.6 |

TABLE 4-continued

| | | | | | | |
|---|---|---|---|---|---|---|
| 227 | 1.5 | No Recurrence | 61 | | Chemo Treated | 7 |
| 228 | 1.4 | No Recurrence | 62 | | Chemo Treated | 10.4 |
| 229 | 1.5 | No Recurrence | 60 | | Chemo Treated | 16.6 |
| 230 | 1.6 | No Recurrence | 61 | | Chemo Treated | 8.9 |
| 231 | 1.6 | No Recurrence | 60 | | Chemo Treated | 5.7 |
| 232 | 1.6 | No Recurrence | 60 | | Chemo Treated | 7.9 |
| 233 | 1.1 | No Recurrence | 83 | | Chemo Treated | 5.5 |
| 234 | 1.5 | No Recurrence | 81 | | Chemo Treated | 3 |
| 235 | 1.6 | No Recurrence | 63 | | Chemo Treated | 14.2 |
| 236 | 1.6 | No Recurrence | 86 | | Chemo Treated | 9.6 |
| 237 | 1.8 | No Recurrence | 60 | | Chemo Treated | 10.2 |
| 238 | 1.8 | No Recurrence | 77 | | Chemo Treated | 7 |
| 239 | 1.3 | No Recurrence | 84 | | Chemo Treated | 11.2 |
| 240 | 1.6 | No Recurrence | 64 | | Chemo Treated | 7.2 |
| 241 | 1.6 | No Recurrence | 84 | | Chemo Treated | 4.6 |
| 242 | 1.5 | No Recurrence | 84 | | Chemo Treated | 10.2 |
| 243 | 1.1 | No Recurrence | 63 | | Chemo Treated | 1.7 |
| 244 | 1.4 | No Recurrence | 62 | | Chemo Treated | 11.7 |
| 245 | 1.3 | No Recurrence | 61 | | Chemo Treated | 4.8 |
| 246 | 1.8 | No Recurrence | 72 | | Chemo Treated | 3.2 |
| 247 | 1.9 | No Recurrence | 86 | | Chemo Treated | 7.8 |
| 248 | 1.8 | No Recurrence | 99 | | Chemo Treated | 8.5 |
| 249 | 1.4 | No Recurrence | 61 | | Chemo Treated | 8.1 |
| 250 | 1.5 | Recurrence | | 54 | Chemo Treated | 24 |
| 251 | 1.5 | Recurrence | | 42 | Chemo Treated | 57.5 |
| 252 | 1.5 | Recurrence | | 21 | Chemo Treated | 70.6 |
| 253 | 1.5 | Recurrence | | 59 | Chemo Treated | 38.9 |
| 254 | 1.5 | Recurrence | | 12 | Chemo Treated | 42.3 |
| 255 | 1.166666667 | No Recurrence | 60 | | Chemo naïve | 9.6 |
| 256 | 1.625 | No Recurrence | 75 | | Chemo Treated | 9.3 |
| 257 | 1.625 | No Recurrence | 60 | | Chemo Treated | 6.7 |
| 258 | 1.5 | No Recurrence | 83 | | Chemo Treated | 7.7 |
| 259 | 1.375 | No Recurrence | 62 | | Chemo Treated | 9.5 |
| 260 | 1.5 | No Recurrence | 64 | | Chemo Treated | 4.5 |
| 261 | 1.375 | No Recurrence | 65 | | Chemo Treated | 7 |
| 262 | 1.5 | No Recurrence | 73 | | Chemo Treated | 10.4 |
| 263 | 1.75 | No Recurrence | 62 | | Chemo Treated | 8.4 |
| 264 | 1.625 | No Recurrence | 69 | | Chemo Treated | 7.9 |
| 265 | 1.625 | No Recurrence | 61 | | Chemo Treated | 11.5 |
| 266 | 1.375 | No Recurrence | 67 | | Chemo Treated | 8.9 |
| 267 | 1.5 | No Recurrence | 84 | | Chemo Treated | 13.2 |
| 268 | 1.25 | No Recurrence | 75 | | Chemo Treated | 12.5 |
| 269 | 1.625 | No Recurrence | 76 | | Chemo Treated | 8 |
| 270 | 1.625 | No Recurrence | 72 | | Chemo Treated | 4.8 |
| 271 | 1.5 | No Recurrence | 62 | | Chemo Treated | 3.7 |
| 272 | 1.375 | No Recurrence | 60 | | Chemo Treated | 7 |
| 273 | 1.625 | No Recurrence | 61 | | Chemo Treated | 5.6 |
| 274 | 1.625 | No Recurrence | 62 | | Chemo Treated | 8.1 |
| 275 | 1.625 | No Recurrence | 61 | | Chemo Treated | 6.3 |
| 276 | 1.875 | No Recurrence | 60 | | Chemo Treated | 3 |
| 277 | 1.5 | No Recurrence | 63 | | Chemo Treated | 8.4 |
| 278 | 1.5 | No Recurrence | 66 | | Chemo Treated | 9.5 |
| 279 | 1.625 | No Recurrence | 62 | | Chemo Treated | 9.1 |
| 280 | 1.5 | No Recurrence | 73 | | Chemo Treated | 10.8 |
| 281 | 1.625 | No Recurrence | 68 | | Chemo Treated | 7.1 |
| 282 | 1.625 | No Recurrence | 60 | | Chemo Treated | 8.5 |
| 283 | 1.5 | No Recurrence | 60 | | Chemo Treated | 7.2 |
| 284 | 1.75 | No Recurrence | 82 | | Chemo Treated | 9.1 |
| 285 | 1.5 | No Recurrence | 67 | | Chemo Treated | 10.4 |
| 286 | 1.333333334 | No Recurrence | 94 | | Chemo Treated | 7.7 |
| 287 | 1.25 | No Recurrence | 101 | | Chemo Treated | 12.6 |
| 288 | 1.625 | No Recurrence | 69 | | Chemo Treated | 11.3 |
| 289 | 1.625 | No Recurrence | 62 | | Chemo Treated | 13.2 |
| 290 | 1.625 | No Recurrence | 68 | | Chemo Treated | 6.5 |
| 291 | 1.625 | No Recurrence | 91 | | Chemo Treated | 10.4 |
| 292 | 1.75 | No Recurrence | 62 | | Chemo Treated | 5.9 |
| 293 | 1.5 | No Recurrence | 69 | | Chemo Treated | 4.4 |
| 294 | 1.5 | No Recurrence | 91 | | Chemo Treated | 5.2 |
| 295 | 1.5 | No Recurrence | 61 | | Chemo Treated | 4.6 |
| 296 | 1.625 | No Recurrence | 85 | | Chemo Treated | 2.3 |
| 297 | 1.625 | No Recurrence | 92 | | Chemo Treated | 2 |
| 298 | 1.375 | No Recurrence | 66 | | Chemo Treated | 4.5 |
| 299 | 1.375 | No Recurrence | 67 | | Chemo Treated | 8.5 |

The samples employed for validation studies are subjected to exact same inclusion criteria as provided in example 1 except that Stages used were I, II and IIIA (thus excluding IIIB and IIIC), and each sample is scored for percentage of tumors stained (0-100) and staining intensity (0-3) for the 5 markers—CD44, ABCC11, N-cadherin, Pan-cadherin and ABCC4. The protocol followed for IHC measurements remain identical to that provided in example 1. The results from grading along with three clinical parameters are fed into the proprietary statistical CanAssist Breast algorithm for obtaining a prediction score (CanAssist Breast relapse score) for stratifying patients into high risk or low risk of breast cancer recurrence The prediction score for each sample is compared with the respective patient's medical history with respect to relapse of the disease within 5 years to understand the accuracy of the present method. The results showed that the method of the present disclosure provides a 95% NPV which signifies high predictive capability when compared with the respective patient's medical history data available.

Example 3: Synergistic Interplay of Markers within the 5 Marker Combination of the Present Disclosure The 5 biomarker combination along with the three clinical parameters of the tumor of the present disclosure is a synergistic combination of markers, which play an important role in prognosis of early stage ER+/PR+ and Her2− breast cancer. Though the individual expression of some of the markers in two samples may be identical, the recurrence profile need not necessarily be the same. It is the interplay of these markers which when assessed by way of the CanAssist Breast algorithm, provides the accurate results for a sample. The validation sample set provided in example 2 above provides good data points to understand the significance of the combination of markers, vis-à-vis individual markers.

As can be seen from table no. 5 provided below (derived from validation sample data of table no. 4), even when one (scenarios 1, 3, 8 and 9), two (scenarios 4, 5, 6 and 7) or three markers (scenarios 2 and 10) between two different samples have similar IHC staining grades, the overall outcome is not necessarily the same. Therefore, no single marker can determine prognosis, and it is the specific combination of 5 biomarkers that is critical for accurate prognostication.

TABLE 5

| Scenario | Sl. No. | Age | A %-M | W %-C | U %-C | R %-M | F %-M | WI-C | CanAssist Score | Outcome |
|---|---|---|---|---|---|---|---|---|---|---|
| 1 | 8 | 52 | 17.5 | 42.5 | 49.1 | 44 | 30.00 | 1.3 | 23.8 | Recurred |
|   | 24 | 42 | 17.5 | 30 | 40.0 | 23 | 12.86 | 1.5 | 3.4 | Not recurred |
| 2 | 7 | 40 | 42.5 | 37.5 | 49.1 | 44 | 27.14 | 1.8 | 24.1 | Recurred |
|   | 27 | 72 | 42.5 | 46.25 | 51.8 | 40 | 27.14 | 1.8 | 3.7 | Not recurred |
| 3 | 5 | 43 | 52.5 | 42.5 | 50.9 | 40 | 27.14 | 1.5 | 20.8 | Recurred |
|   | 14 | 59 | 50 | 46.25 | 50.9 | 29 | 18.57 | 1.8 | 5.5 | Not recurred |
| 4 | 5 | 43 | 52.5 | 42.5 | 50.9 | 40 | 27.14 | 1.5 | 20.8 | Recurred |
|   | 27 | 72 | 42.5 | 46.25 | 51.8 | 40 | 27.14 | 1.8 | 3.7 | Not recurred |
| 5 | 3 | 72 | 50 | 47.5 | 52.7 | 44 | 35.71 | 1.5 | 19.4 | Recurred |
|   | 28 | 51 | 50 | 47.5 | 53.6 | 22 | 12.86 | 1.8 | 13.1 | Not recurred |
| 6 | 155 | 41 | 12.5 | 45 | 50.9 | 42 | 22.86 | 1.3 | 30.1 | Recurred |
|   | 15 | 59 | 12.5 | 38.75 | 50.9 | 25 | 15.00 | 1.4 | 7.1 | Not recurred |
| 7 | 156 | 47 | 50 | 37.5 | 45.5 | 50 | 35.71 | 1.3 | 100 | Recurred |
|   | 47 | 60 | 50 | 37.5 | 50.9 | 20 | 12.86 | 1.4 | 9.8 | Not recurred |
| 8 | 159 | 50 | 12.5 | 42.5 | 49.1 | 44 | 12.86 | 1.5 | 19.8 | Recurred |
|   | 47 | 60 | 50 | 37.5 | 50.9 | 20 | 12.86 | 1.4 | 9.8 | Not recurred |
| 9 | 154 | 60 | 37.5 | 47.5 | 52.7 | 28 | 28.57 | 1.8 | 16.7 | Recurred |
|   | 22 | 74 | 21.25 | 40 | 47.3 | 28 | 15.71 | 1.5 | 5.6 | Not recurred |
| 10 | 2 | 66 | 57.5 | 45 | 50.9 | 48 | 34.29 | 1.8 | 15.6 | Recurred |
|   | 17 | 59 | 32.5 | 45 | 50.9 | 36 | 19.29 | 1.8 | 4 | Not recurred |

Figure 1:
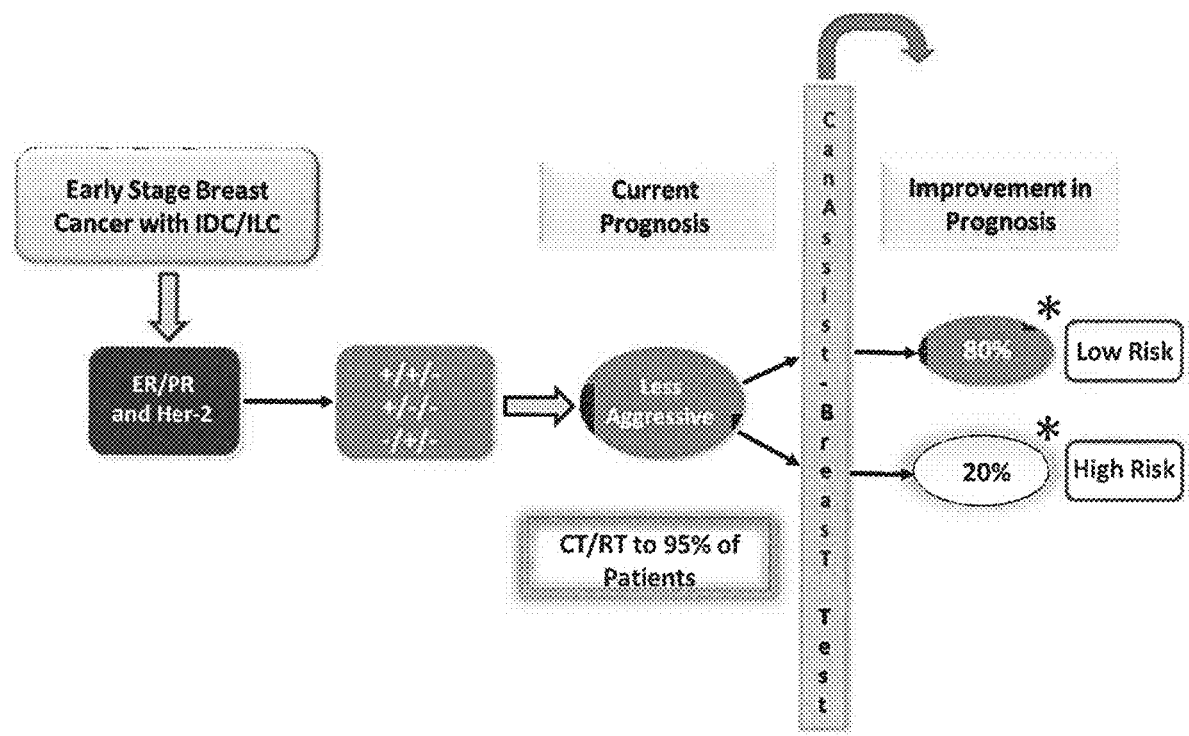
FIG. 1 illustrates current method of prognosis and improvement using CanAssist-Breast: Overview of factors considered for risk stratification of patients with early stage Her2 negative breast cancer.

Example 4: Prognostic Test of the Instant Disclosure v/s Prior Known Means of Prognostication Risk stratification of patients into high/low risk of breast cancer recurrence in the prior art is carried out by analyzing patient samples for presence or absence of hormone receptor status and clinical Stage of the disease. Eg: If a Her2-, early stage breast cancer patient's sample shows any of the combination of receptor expression including ER+/PR+ or ER+/PR− or ER−/PR+ then the said patient is considered at low risk for recurrence compared to a patient not expressing both ER and PR receptors but such a patient is still prescribed to have chemotherapy treatment. However, chemotherapy is not beneficial in majority (~80%) of such ER+ and/PR+, Her2− early stage breast cancer patients in terms of preventing recurrence and often leads to reduction in quality of life (FIG. 1).

On the contrary, the prognostic test of the instant disclosure is performed on these Her2-, early stage breast cancer patients with ER+ and/or PR+ disease, which includes assessing expression of a 5 marker combination comprising (CD44, ABCC11, N-cadherin, Pan-cadherin and ABCC4). The prognostic test of the instant disclosure does not proceed if the hormone receptor status is found negative for both the markers ER or PR. The prognostic test of the instant disclosure is performed by carrying out an IHC based assay for expression of said 5 biomarker combination, followed by grading the expression of the biomarkers on the basis of parameters including percentage of staining and intensity of staining. The data from said grading along with status of clinical prognostic parameters is inputted into a proprietary statistical algorithm or module for obtaining a prediction score. This score helps in deciphering if the patient falls under the high risk category or low risk category. Accordingly, a low risk patient is advised to take optimum therapy as per the clinician's decision (FIG. 1) thus leading to improved quality of life.

Therefore, if a patient sample was analyzed by the prior known method, said patient would be classified only based on hormone receptor status, and most often advised to take aggressive chemotherapy which may not be beneficial and will reduce quality of life. However, on the contrary as the instant prognostic test would take into consideration the 5 biomarker combination expression which are specific to tumor biology involved in recurrence and compute a relapse score which is assessed based on biomarker data and clinical prognostic factors, said information could render the same patient sample into low risk and be advised treatment accordingly. Thus, the doctors employing the prognostic test of the instant disclosure can very accurately assess the patient samples and stratify them effectively into high risk or low risk for cancer recurrence and devise a suitable and optimum treatment module.

Advantages of the method and the biomarker combination of the present disclosure:

1. The method of the present disclosure uses biomarkers from pathways other than hormone regulation and proliferation pathways thereby enhancing its predictive potential.
2. Importantly, the prognostic test is developed and validated on Node negative and Node positive patients from tumor stages I-IIIA and this makes it a broad based test with wider applicability and enhanced utility worldwide. Other prognostic tests available in the art have mostly been developed in Stage I node negative patients and have reduced applicability in node positive patients.
3. The method of the present disclosure is not only prognostic, but also chemopredictive (i.e, can decide benefit of chemotherapy to patients), unlike other methods in the art, some of which are only prognostic. Hence, the prognostic test of the instant disclosure can help reduce unwanted chemotherapy and prescribe additional targeted therapy via a central lab facility.
4. The method of the present disclosure uses biomarker combination hitherto unknown to have prognostic application in Breast Cancer. Further, these marker combination(s) are also selected for their potential to be targeted for developing new drugs to treat Breast Cancer in the future. No earlier known method has considered this factor in their test development protocol. This is possible because the biomarkers employed by the present disclosure are membrane associated and hence can be targeted to make new drugs.
5. All other prognostic methods developed so far are expensive and not widely used in geographies outside the Western world. However, the method of the present disclosure is the first test to be affordable in India and worldwide, thereby enhancing its utility and reach.
6. The prognostic and predictive test of the present disclosure can be a companion test for new drugs to come in the market.
7. The method of prognosis or the prognostic test of the instant disclosure is robust and a simple IHC based test with high NPV when compared to any other prognostic tests available in the prior art for breast cancer detection and prognosis.
8. The test of the present disclosure is developed on patients of Stage I, II and IIIA. The reason IIIA is included is there are a group of these patients also shown to do well without chemotherapy. On the contrary, the methods of the prior art have been developed on patient samples from stage I breast cancer but however, validated on Stage II breast cancer and node positive patients. This means that since these models are not built on that stage II data set, they are not as robust and applicable on the Stage II cancers as training and validation should always preferably be done on cohorts with identical inclusion criteria.

Although the disclosure and exemplification has been provided by way of illustrations and examples for the purpose of clarity and understanding, it is apparent to a person skilled in the art that various changes and modifications can be practiced without departing from the spirit or scope of the disclosure. Accordingly, the foregoing descriptions and examples should not be construed as limiting the scope of the present disclosure.

The description of the embodiments of the present disclosure reveals the general nature of the embodiments that are readily suitable for modification and/or adaptation for various applications by applying the current knowledge. Such specific embodiments of the disclosure, without departing from the generic concept, and, therefore, such adaptations and modifications should and are intended to be comprehended and considered within the meaning and range of equivalents of the disclosed embodiments.

It is also to be understood that the phrases or terms employed herein are for the purpose of description and not intended to be of any limitation. Throughout the present disclosure, the word "comprise", or variations such as "comprises" or "comprising" wherever used, are to be understood to imply the inclusion of a stated element, integer or step, or group of elements, integers or steps, but not the exclusion of any other element, integer or step, or group of elements, integers or steps.

Where a numerical limit or range is stated herein, the endpoints are included. Also, values and sub-ranges within a numerical limit or range are specifically included as if explicitly written out.

With respect to the use of any plural and/or singular terms in the present disclosure, those of skill in the art can translate from the plural to the singular and/or from the singular to the plural as is considered appropriate to the context and/or application. The various singular/plural permutations may be expressly set forth herein for the sake of clarity.

Any discussion of documents, acts, materials, devices, articles and the like that has been included in this specification is solely for the purpose of providing a context for the present disclosure. It is not to be taken as an admission that any or all of these matters form a part of the prior art base or are common general knowledge in the field relevant to the present disclosure, as it existed anywhere before the priority date of this application.

The contents of all references, patents, and published patent applications cited throughout this application are incorporated herein by reference for all purposes.

We claim:

1. A method of obtaining measurements of biomarker expression and clinical parameters, comprising:
    obtaining a biological sample taken from a subject having estrogen-receptor-positive and/or progesterone-receptor-positive (ER+/PR+) and human-epidermal-growth-factor-receptor-2-negative (Her2−) breast cancer or after removal of the breast cancer;
    contacting the biological sample with antibodies that are each specific for a respective biomarker;
    quantifying binding of each antibody to the respective biomarker in order to measure expression of only five biomarkers wherein the five biomarkers are cluster of differentiation 44 (CD44), ATP-binding cassette transporter sub-family C member 11 (ABCC11), N-cadherin, Pan-cadherin and ATP-binding cassette sub-family C member 4 (ABCC4); and
    obtaining measurements of clinical parameters comprising node status, tumor grade, and tumor size (T) wherein the node status includes tumor node positive or tumor node negative, the tumor grade includes Grades 1, 2 or 3, and the tumor size (T) includes T1, T2, or T3.

2. A method of performing immunohistochemistry (IHC) on a tumor sample obtained from a subject having breast cancer or after removal of the breast cancer, comprising:
    performing the method as claimed in claim 1 on the tumor sample by IHC to measure the expression of the five biomarkers CD44, ABCC11, N-cadherin, Pan-cadherin and ABCC4.

3. A method of prognosing and treating a subject having ER+/PR+ and Her2− breast cancer or after removal of the breast cancer, comprising:
    prognosing risk of breast-cancer recurrence for the subject by performing, and analyzing the results of the method as claimed in claim 2; and
    treating the prognosed subject having high risk for breast-cancer recurrence with chemotherapy,
    wherein greater than 9% probability of breast-cancer recurrence within five years of initial treatment of the breast cancer constitutes high risk for breast-cancer recurrence.

4. The method as claimed in claim 1, wherein the breast cancer is stage I, II or IIIA invasive ductal carcinoma or invasive lobular carcinoma of the breast.

5. The method as claimed in claim 3, wherein the breast-cancer recurrence is prognosed after surgical removal of the breast cancer.

6. The method as claimed in claim 2, wherein the IHC is morphometric IHC; and wherein expression of the five biomarkers is measured on basis of percentage of cells stained and staining intensity of cells.

7. The method as claimed in claim 1, wherein the antibodies do not include an antibody specific for P-cadherin.

8. The method as claimed in claim 2, wherein the tumor sample obtained from the subject is collected, fixed and sectioned prior to the IHC; and wherein the IHC is performed by adding primary antibodies and secondary antibodies conjugated with a detectable label, and detecting a color or fluorescence from the detectable label.

9. A method of predicting the likelihood of recurrence of breast cancer in a subject having ER+/PR+ and Her2− breast cancer or after removal of the breast cancer, comprising:
    measuring expression of five biomarkers CD44, ABCC11, N-cadherin, Pan-cadherin and ABCC4 and obtaining measurements of clinical parameters comprising node status, tumor grade, and tumor size by performing the method as claimed in claim 1 on a tumor sample obtained from the subject such that the expression of the five biomarkers is measured on basis of percentage of cells stained and staining intensity of cells;
    inputting data obtained from measuring the expression of the five biomarkers and from obtaining the measurements of the clinical parameters, into an algorithm for generation of a risk score; and
    determining risk of breast-cancer recurrence for the subject based on a cutoff value of the risk score,
    wherein the algorithm was developed by training the algorithm with multiple retrospective patient history data sets for contribution of the biomarkers and clinical parameters to breast-cancer recurrence.

10. The method as claimed in claim 9, wherein the breast cancer is stage I, II or IIIA invasive ductal carcinoma or invasive lobular carcinoma of the breast.

11. The method as claimed in claim 2, wherein the breast cancer is stage I, II or IIIA invasive ductal carcinoma or invasive lobular carcinoma of the breast.

12. The method as claimed in claim 3, wherein the breast cancer is stage I, II or IIIA invasive ductal carcinoma or invasive lobular carcinoma of the breast.

* * * * *